US012678309B2

(12) United States Patent
Arbefeuille et al.

(10) Patent No.: US 12,678,309 B2
(45) Date of Patent: Jul. 14, 2026

(54) AORTIC PROSTHESIS DELIVERY SYSTEM AND METHOD OF USE

(71) Applicant: Bolton Medical, Inc., Sunrise, FL (US)

(72) Inventors: Samuel Arbefeuille, Sunrise, FL (US);
Eduardo A. Garcia, Sunrise, FL (US);
Timothy Lostetter, Sunrise, FL (US);
Eitan Magen, Sunrise, FL (US); Bryan Vancheri, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 1233 days.

(21) Appl. No.: 17/522,251

(22) Filed: Nov. 9, 2021

(65) Prior Publication Data

US 2022/0160529 A1 May 26, 2022

Related U.S. Application Data

(60) Provisional application No. 63/210,381, filed on Jun. 14, 2021, provisional application No. 63/153,701, (Continued)

(51) Int. Cl.
*A61F 2/07* (2013.01)
*A61F 2/06* (2013.01)
(Continued)

(52) U.S. Cl.
CPC .............. *A61F 2/9662* (2020.05); *A61F 2/07* (2013.01); *A61F 2/954* (2013.01); (Continued)

(58) Field of Classification Search
CPC .......... A61F 2/9662; A61F 2/07; A61F 2/954; A61F 2002/065; A61F 2002/9665; A61F 2002/9511; A61F 2002/075
See application file for complete search history.

(56) References Cited

U.S. PATENT DOCUMENTS

| | | |
|---|---|---|
| 5,242,452 A | 9/1993 | Inoue |
| 5,507,769 A | 4/1996 | Marin et al. |

(Continued)

FOREIGN PATENT DOCUMENTS

| | | |
|---|---|---|
| AU | 2016256777 B1 | 4/2017 |
| CN | 102413794 A | 4/2012 |

(Continued)

OTHER PUBLICATIONS

International Search Report and Written Opinion for International Application No. PCT/US2021/058526 dated Mar. 18, 2022.

(Continued)

*Primary Examiner* — Jing Rui Ou
(74) *Attorney, Agent, or Firm* — Stephen J. Kenny; Emily H. Yasharpour; Foley Hoag LLP

(57) ABSTRACT

A stent graft for treating an arterial aneurysm includes loops fixed to struts of stents, wherein the struts define distal and proximal apices. The ends of a ligature can be linked by a wire in a stent graft delivery system that threads anchor loops longitudinally spanning ends of the ligature to maintain the stent in a radially constricted position during delivery to the aneurysm. A delivery system and method for implanting a stent graft prosthesis includes and employs a torque component at a distal end of the stent graft prosthesis, whereby following advancement of the stent graft to a surgical site in a constrained or partially constrained configuration, torque is applied to the torque component to rotationally align the stent graft about a longitudinal axis of the stent graft, followed by deployment of the stent graft in correct rotational alignment. A delivery system and method of its use includes an apex capture assembly, a leg clasp, and a leg stop for capturing a stent graft during orientation and stabilization at an implantation site of a surgical site.

12 Claims, 70 Drawing Sheets

Related U.S. Application Data filed on Feb. 25, 2021, provisional application No. 63/111,357, filed on Nov. 9, 2020.

(51) Int. Cl.

| | |
|---|---|
| *A61F 2/954* | (2013.01) |
| *A61F 2/966* | (2013.01) |
| *A61F 2/95* | (2013.01) |

(52) U.S. Cl.

CPC ... *A61F 2002/065* (2013.01); *A61F 2002/075* (2013.01); *A61F 2002/9511* (2013.01); *A61F 2002/9665* (2013.01)

(56) References Cited

U.S. PATENT DOCUMENTS

| | | | |
|---|---|---|---|
| 5,713,948 A | 2/1998 | Uflacker | |
| 5,873,906 A | 2/1999 | Lau et al. | |
| 6,280,464 B1 | 8/2001 | Hayashi | |
| 6,776,791 B1 | 8/2004 | Stallings et al. | |
| 7,435,253 B1 | 10/2008 | Hartley et al. | |
| 7,763,063 B2 | 7/2010 | Arbefeuille et al. | |
| 8,007,605 B2 | 8/2011 | Arbefeuille et al. | |
| 8,137,393 B2 | 3/2012 | Ishimaru et al. | |
| 8,172,895 B2 | 5/2012 | Anderson et al. | |
| 8,236,040 B2 | 8/2012 | Mayberry et al. | |
| 8,486,129 B2 | 7/2013 | Lautherjung | |
| 8,500,792 B2 | 8/2013 | Berra | |
| 8,926,693 B2 | 1/2015 | Duffy et al. | |
| 9,101,455 B2 | 8/2015 | Roeder et al. | |
| 9,101,506 B2 | 8/2015 | Arbefeuille et al. | |
| 9,226,814 B2 | 1/2016 | Jensen et al. | |
| 9,278,018 B2 | 3/2016 | Roeder | |
| 9,364,314 B2 | 6/2016 | Berra et al. | |
| 9,375,308 B2 | 6/2016 | Norris | |
| 9,439,751 B2 | 9/2016 | White et al. | |
| 9,592,112 B2 | 3/2017 | Arbefeuille et al. | |
| 9,827,123 B2 | 11/2017 | Arbefeuille et al. | |
| 9,861,503 B2 | 1/2018 | Barthold et al. | |
| 9,877,857 B2 | 1/2018 | Arbefeuille et al. | |
| 9,913,743 B2 | 3/2018 | Arbefeuille et al. | |
| 10,005,269 B2 | 6/2018 | Hall et al. | |
| 10,080,674 B2 | 9/2018 | Yuan et al. | |
| 10,292,850 B2 | 5/2019 | Vad et al. | |
| 10,299,951 B2 | 5/2019 | Arbefeuille et al. | |
| 10,390,930 B2 | 8/2019 | Arbefeuille et al. | |
| 10,478,320 B2 | 11/2019 | Shahriari | |
| 10,617,542 B2 | 4/2020 | Chakfe et al. | |
| 10,898,357 B2 | 1/2021 | Arbefeuille et al. | |
| 11,219,540 B2 | 1/2022 | Arbefeuille | |
| 11,291,572 B2 | 4/2022 | Garcia | |
| 11,376,145 B2 | 7/2022 | Arbefeuille et al. | |
| 11,730,584 B2 | 8/2023 | Arbefeuille | |
| 11,744,722 B2 | 9/2023 | Garcia | |
| 12,171,651 B2 | 12/2024 | Arbefeuille | |
| 2002/0038144 A1 | 3/2002 | Trout et al. | |
| 2002/0062133 A1 | 5/2002 | Gilson et al. | |
| 2002/0151956 A1 | 10/2002 | Chobotov et al. | |
| 2002/0177890 A1* | 11/2002 | Lenker | A61F 2/90 |
| | | | 623/1.12 |
| 2003/0233140 A1 | 12/2003 | Hartley et al. | |
| 2004/0073289 A1 | 4/2004 | Hartley | |
| 2005/0049674 A1 | 3/2005 | Berra et al. | |
| 2005/0119722 A1 | 6/2005 | Styrc et al. | |
| 2005/0154444 A1 | 7/2005 | Quadri | |
| 2006/0004433 A1 | 1/2006 | Greenberg et al. | |
| 2006/0015171 A1 | 1/2006 | Armstrong | |
| 2006/0020319 A1 | 1/2006 | Kim et al. | |
| 2006/0184226 A1 | 8/2006 | Austin | |
| 2007/0043425 A1 | 2/2007 | Hartley et al. | |
| 2007/0213805 A1 | 9/2007 | Schaeffer et al. | |
| 2007/0233223 A1 | 10/2007 | Styrc | |
| 2008/0082154 A1 | 4/2008 | Tseng et al. | |
| 2008/0132988 A1 | 6/2008 | Jordan | |
| 2008/0294234 A1 | 11/2008 | Hartley et al. | |
| 2009/0248135 A1 | 10/2009 | Bruszewski et al. | |
| 2009/0259291 A1* | 10/2009 | Kolbel | A61F 2/95 |
| | | | 623/1.13 |
| 2010/0114290 A1 | 5/2010 | Rasmussen et al. | |
| 2010/0234932 A1 | 9/2010 | Arbefeuille et al. | |
| 2010/0268319 A1 | 10/2010 | Bruszewski et al. | |
| 2011/0190862 A1 | 8/2011 | Bashiri et al. | |
| 2011/0264192 A1* | 10/2011 | Hartley | A61F 2/07 |
| | | | 623/1.13 |
| 2012/0172965 A1 | 7/2012 | Kratzberg et al. | |
| 2012/0323302 A1 | 12/2012 | Brinser | |
| 2013/0116773 A1 | 5/2013 | Roeder et al. | |
| 2013/0158648 A1 | 6/2013 | Hartley et al. | |
| 2013/0289713 A1 | 10/2013 | Pearson et al. | |
| 2014/0046429 A1 | 2/2014 | Cragg et al. | |
| 2014/0148888 A1* | 5/2014 | Barrand | A61F 2/07 |
| | | | 623/1.2 |
| 2014/0180378 A1 | 6/2014 | Roeder | |
| 2014/0277338 A1* | 9/2014 | Kolbel | A61F 2/07 |
| | | | 623/1.11 |
| 2014/0336745 A1 | 11/2014 | Barthold et al. | |
| 2015/0051691 A1 | 2/2015 | Zukowski et al. | |
| 2015/0105819 A1 | 4/2015 | Becking et al. | |
| 2015/0105849 A1 | 4/2015 | Cohen et al. | |
| 2015/0127015 A1 | 5/2015 | Bolduc et al. | |
| 2015/0202065 A1 | 7/2015 | Shalev et al. | |
| 2015/0265444 A1 | 9/2015 | Kitaoka | |
| 2016/0120667 A1 | 5/2016 | Bolduc et al. | |
| 2016/0250050 A1 | 9/2016 | Lim et al. | |
| 2016/0278910 A1 | 9/2016 | Kelly | |
| 2016/0302950 A1 | 10/2016 | Marmur et al. | |
| 2017/0281382 A1 | 10/2017 | Lostetter et al. | |
| 2019/0231514 A1 | 8/2019 | Arbefeuille | |
| 2019/0231568 A1 | 8/2019 | Garcia | |
| 2019/0269498 A1 | 9/2019 | Arbefeuille et al. | |
| 2019/0269537 A1 | 9/2019 | Arbefeuille | |
| 2019/0321207 A1 | 10/2019 | Arbefeuille et al. | |
| 2019/0350694 A1 | 11/2019 | Arbefeuille et al. | |
| 2021/0100669 A1 | 4/2021 | Arbefeuille et al. | |
| 2022/0160529 A1 | 5/2022 | Arbefeuille et al. | |
| 2022/0192851 A1 | 6/2022 | Garcia | |
| 2022/0313464 A1 | 10/2022 | Arbefeuille et al. | |
| 2023/0338133 A1 | 10/2023 | Arbefeuille | |
| 2024/0197503 A1 | 6/2024 | Garcia | |

FOREIGN PATENT DOCUMENTS

| | | |
|---|---|---|
| CN | 102711664 A | 10/2012 |
| CN | 104027187 A | 9/2014 |
| CN | 104114201 A | 10/2014 |
| CN | 105832447 A | 8/2016 |
| CN | 105943213 A | 9/2016 |
| CN | 106344208 A | 1/2017 |
| DE | 102012101103 B3 | 7/2013 |
| EP | 2471498 A1 | 7/2012 |
| EP | 2501334 A1 | 9/2012 |
| EP | 2735283 A1 | 5/2014 |
| EP | 2740440 A2 | 6/2014 |
| EP | 2745812 A1 | 6/2014 |
| EP | 3040054 A1 | 7/2016 |
| EP | 3146993 A1 | 3/2017 |
| EP | 3187155 A1 | 7/2017 |
| EP | 3272319 A1 | 1/2018 |
| EP | 3320881 A1 | 5/2018 |
| EP | 3395302 A1 | 10/2018 |
| EP | 3733124 A1 | 11/2020 |
| GB | 2464978 A | 5/2010 |
| JP | 2019-088890 A | 6/2019 |
| WO | WO-96/36297 A1 | 11/1996 |
| WO | WO-97/03624 A1 | 2/1997 |
| WO | WO-97/25002 A1 | 7/1997 |
| WO | WO-97/48350 A1 | 12/1997 |
| WO | WO-01/60285 A1 | 8/2001 |
| WO | WO-2002/083038 A2 | 10/2002 |
| WO | WO-2006/037086 A1 | 4/2006 |
| WO | WO-2007/115017 A1 | 10/2007 |
| WO | WO-2009/148594 A1 | 12/2009 |
| WO | WO-2010/105195 A2 | 9/2010 |

(56)  References Cited

FOREIGN PATENT DOCUMENTS

| | | | |
|---|---|---|---|
| WO | WO-2012/116368 | A2 | 8/2012 |
| WO | WO-2012/145823 | A1 | 11/2012 |
| WO | WO-2014/149022 | A1 | 9/2014 |
| WO | WO-2014/162306 | A2 | 10/2014 |
| WO | WO-2015/070792 | A1 | 5/2015 |
| WO | WO-2016/122862 | A1 | 8/2016 |
| WO | WO-2017/106156 | A1 | 6/2017 |
| WO | WO-2018/183563 | A1 | 10/2018 |
| WO | WO-2019/040326 | A1 | 2/2019 |

OTHER PUBLICATIONS

International Search Report and Written Opinion for International Application No. PCT/US18/19510 dated Jul. 11, 2018.
Extended European Search Report for EP Application No. 25162091.0 dated Oct. 6, 2025.

* cited by examiner

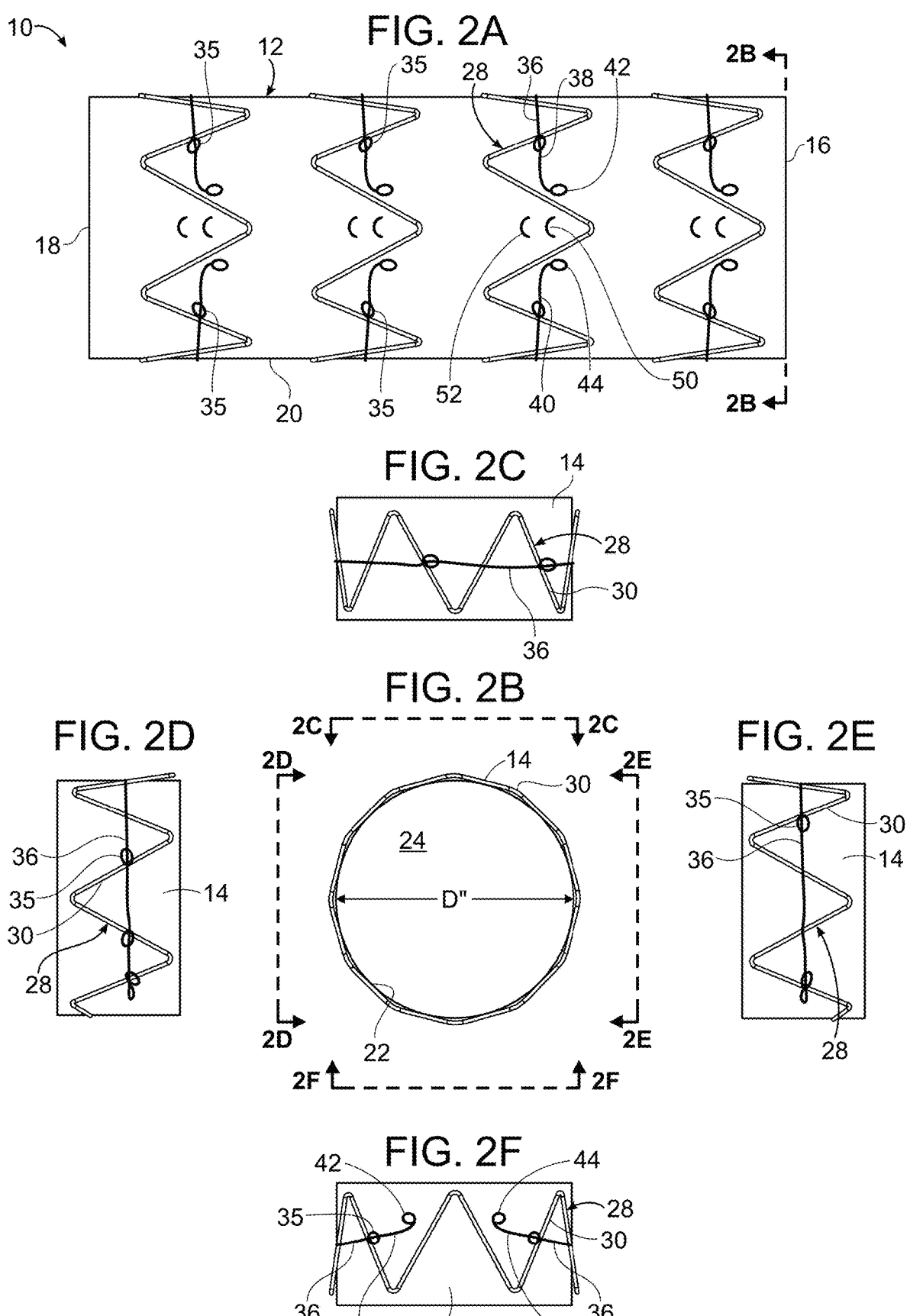

FIG. 3A
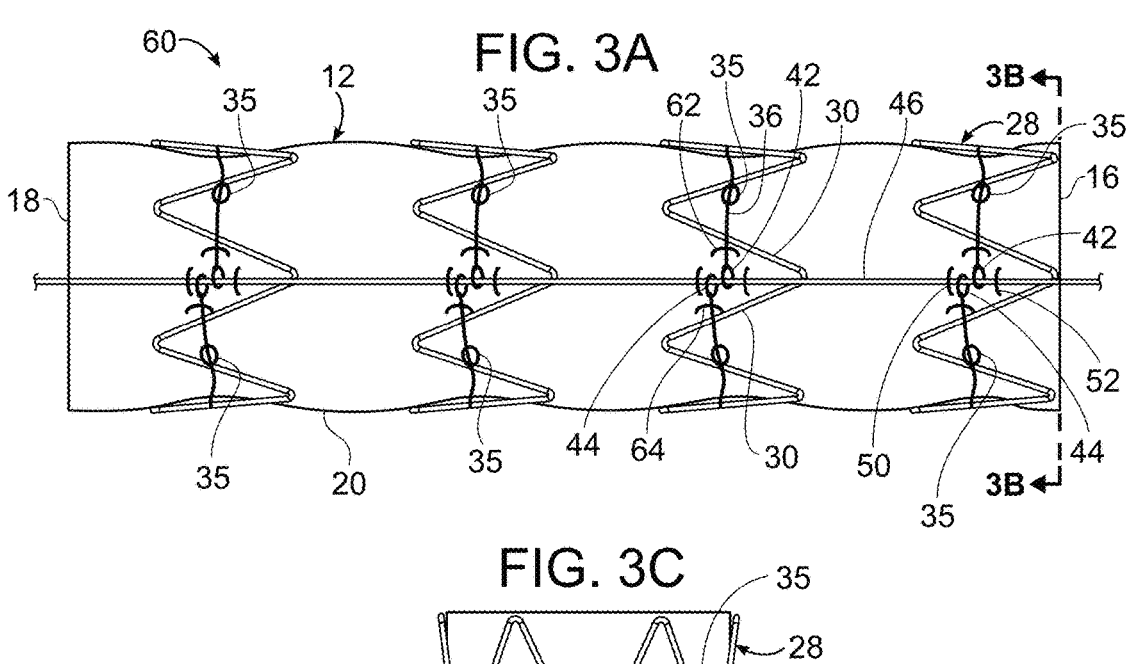
FIG. 3C
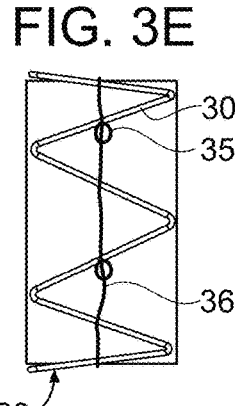
FIG. 3B
FIG. 3D
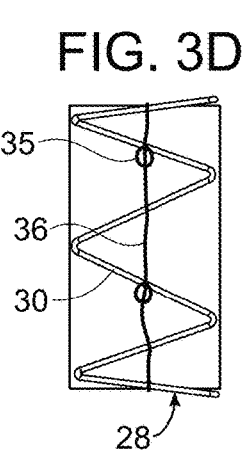
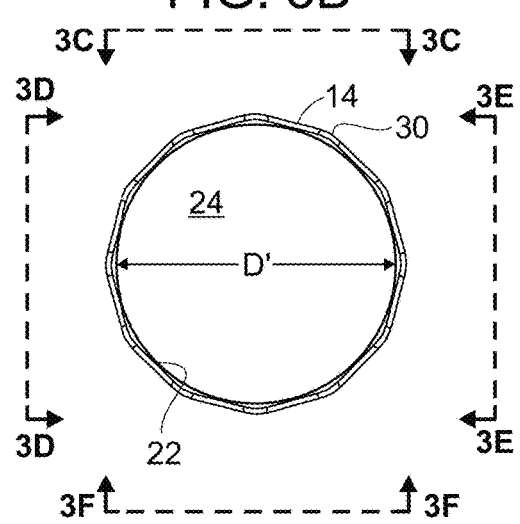
FIG. 3E
FIG. 3F
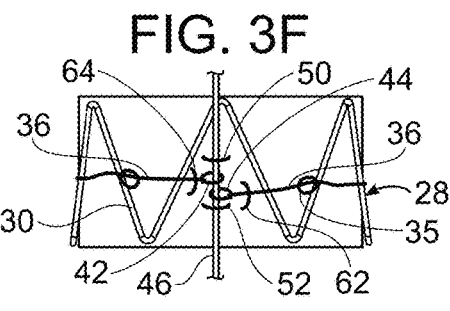

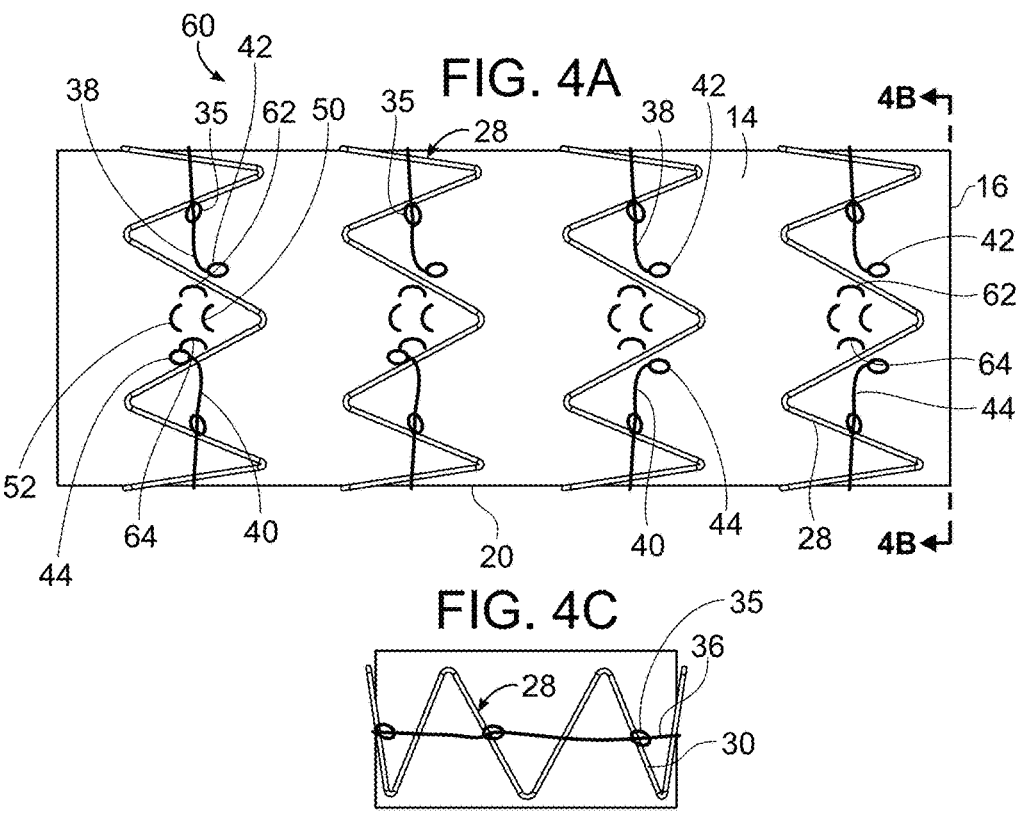
FIG. 4A
FIG. 4C
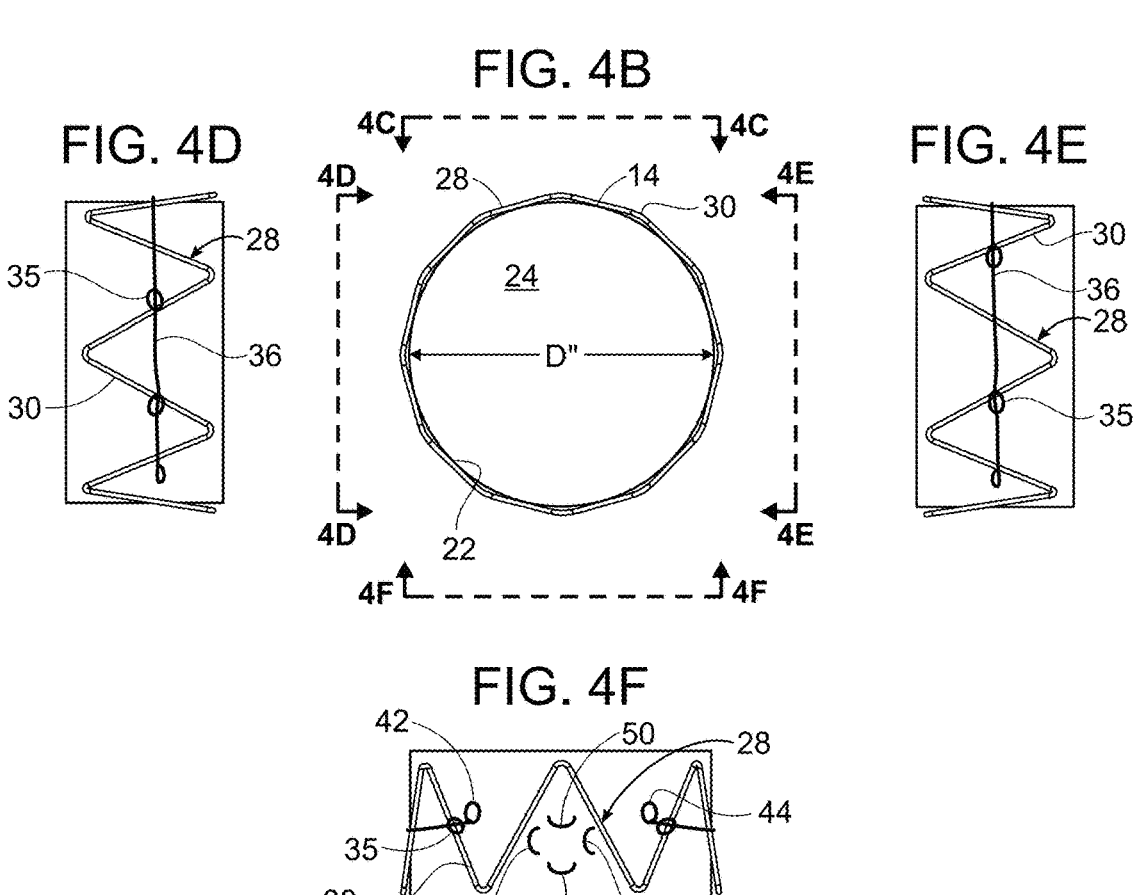
FIG. 4D
FIG. 4B
FIG. 4E
FIG. 4F

FIG. 5A
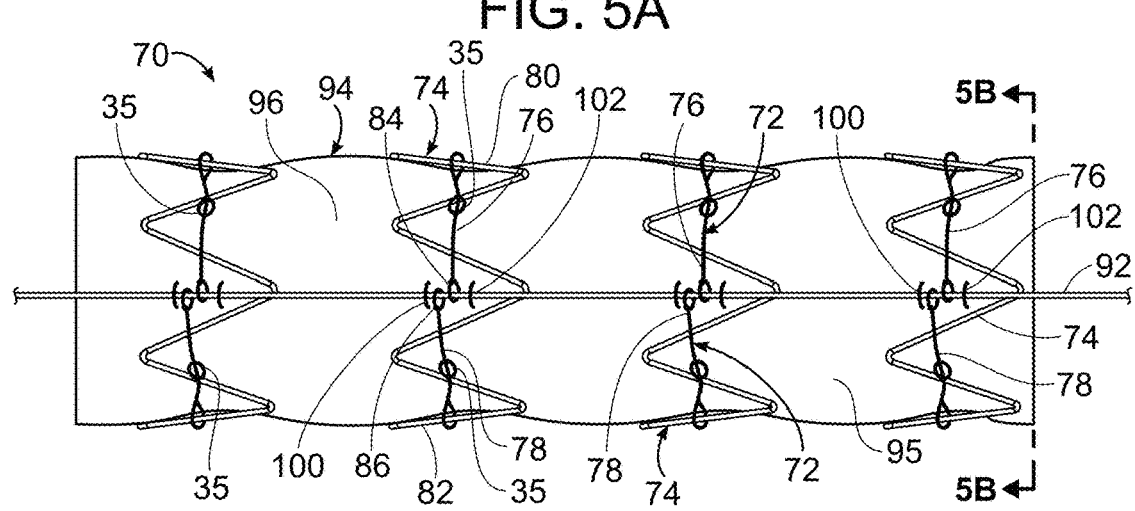
FIG. 5C
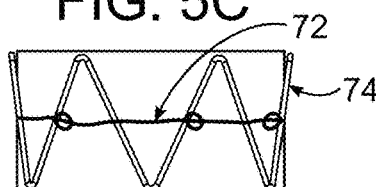
FIG. 5B
FIG. 5D
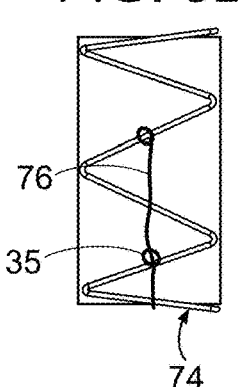
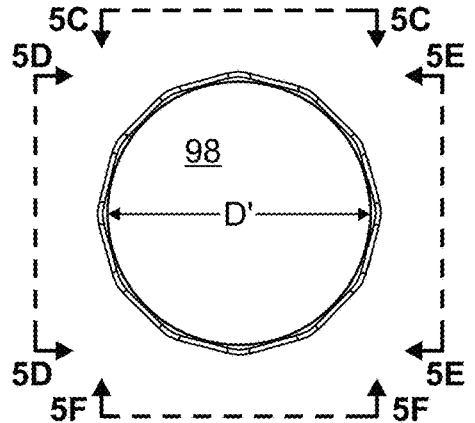
FIG. 5E
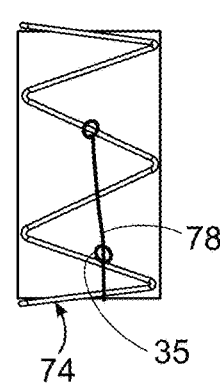
FIG. 5F
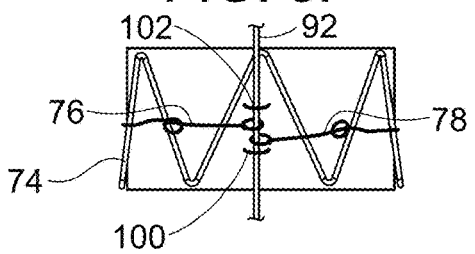

FIG. 6A
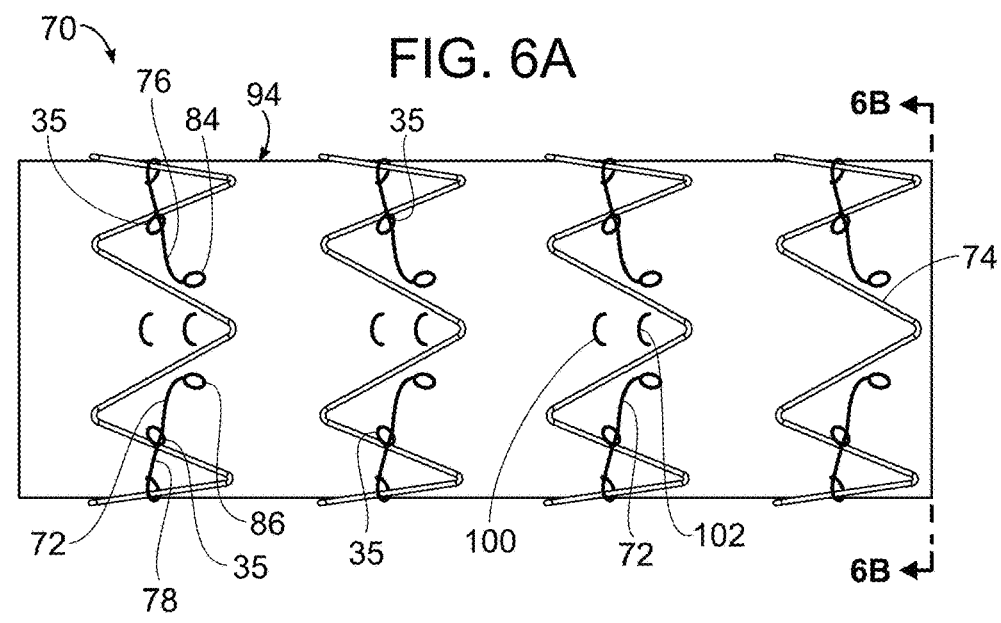
FIG. 6C
FIG. 6B
FIG. 6D
FIG. 6E
FIG. 6F
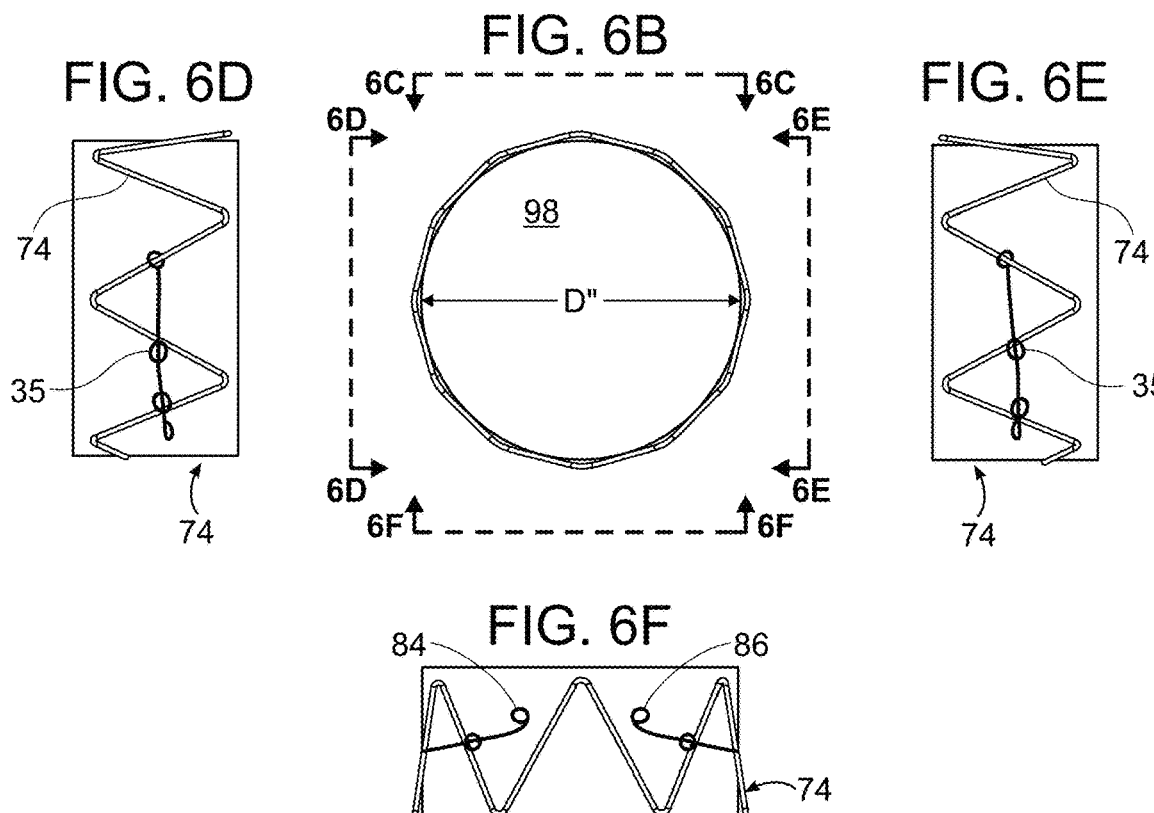

FIG. 7A
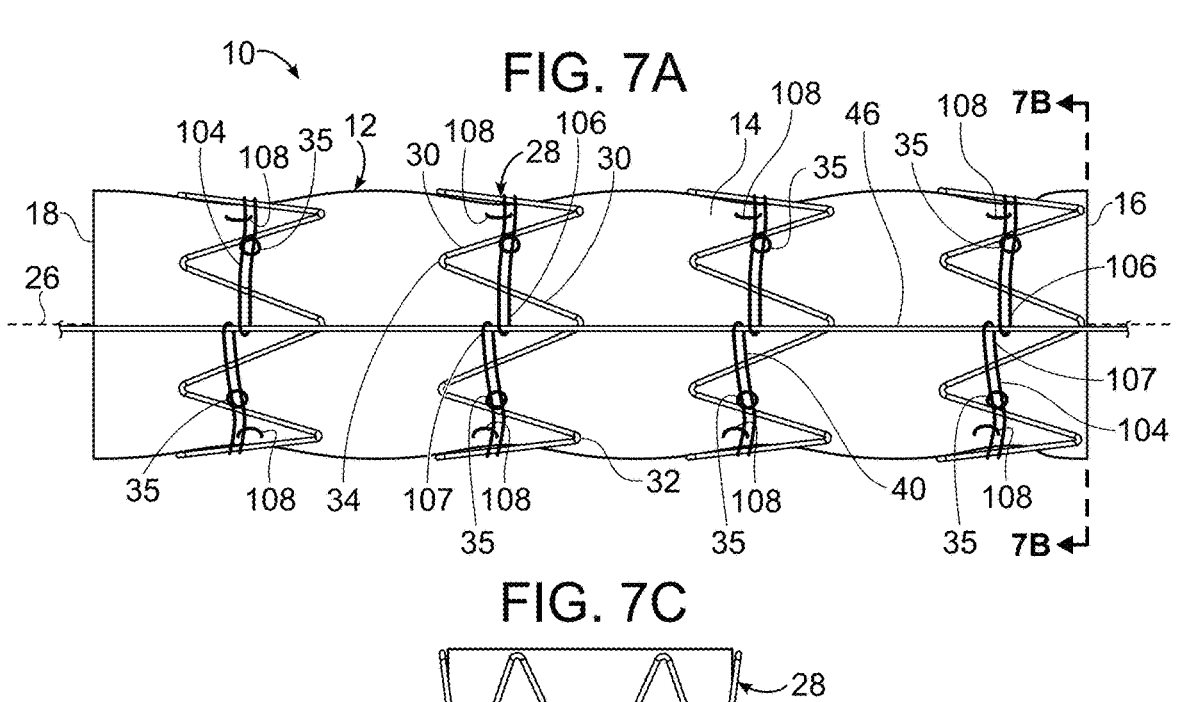
FIG. 7C
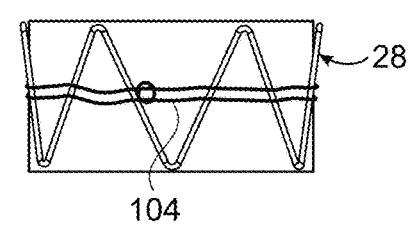
FIG. 7B
FIG. 7D
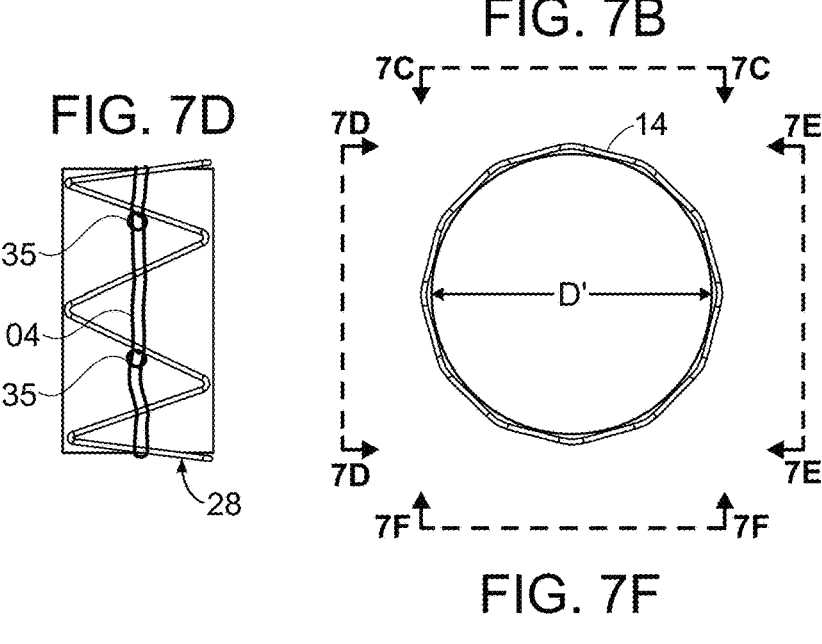
FIG. 7E
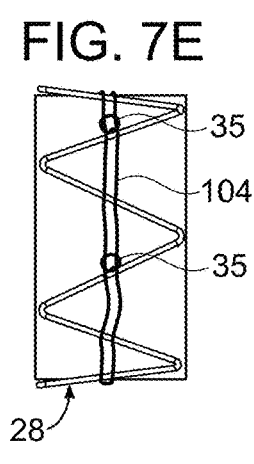
FIG. 7F
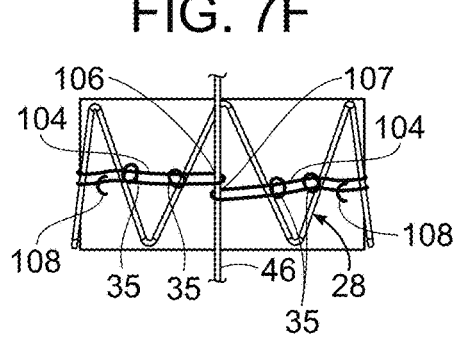

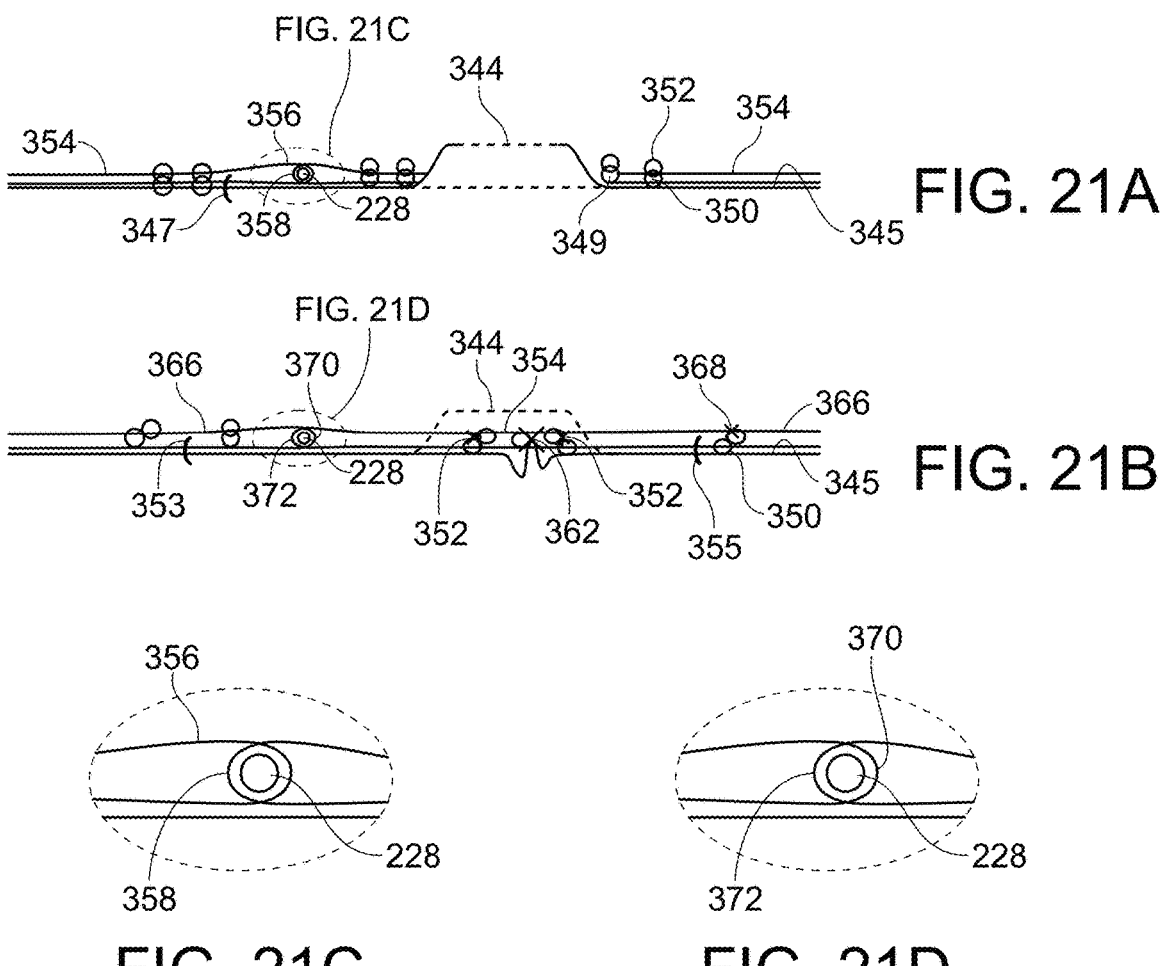
FIG. 21A
FIG. 21B
FIG. 21C
FIG. 21D
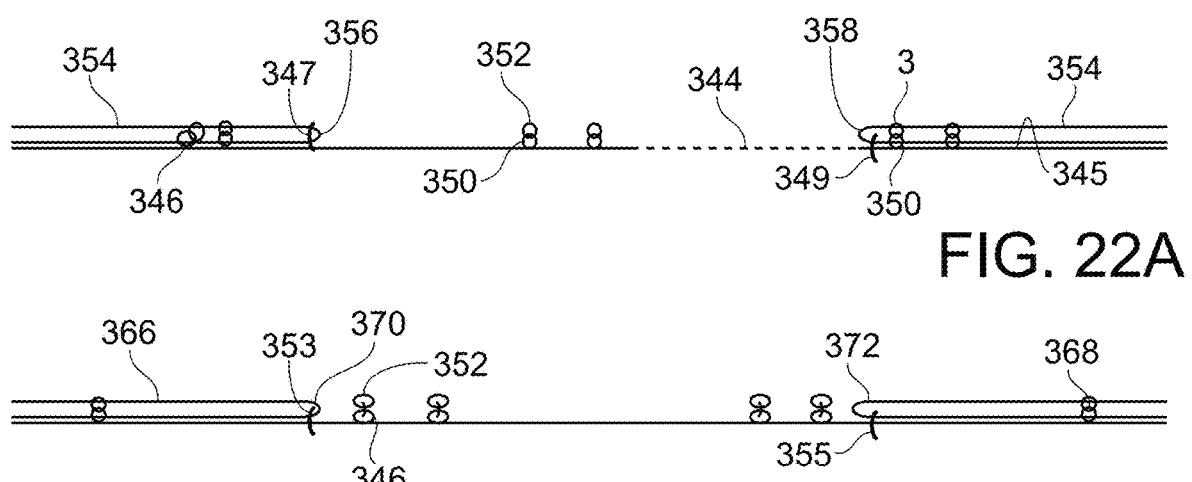
FIG. 22A
FIG. 22B

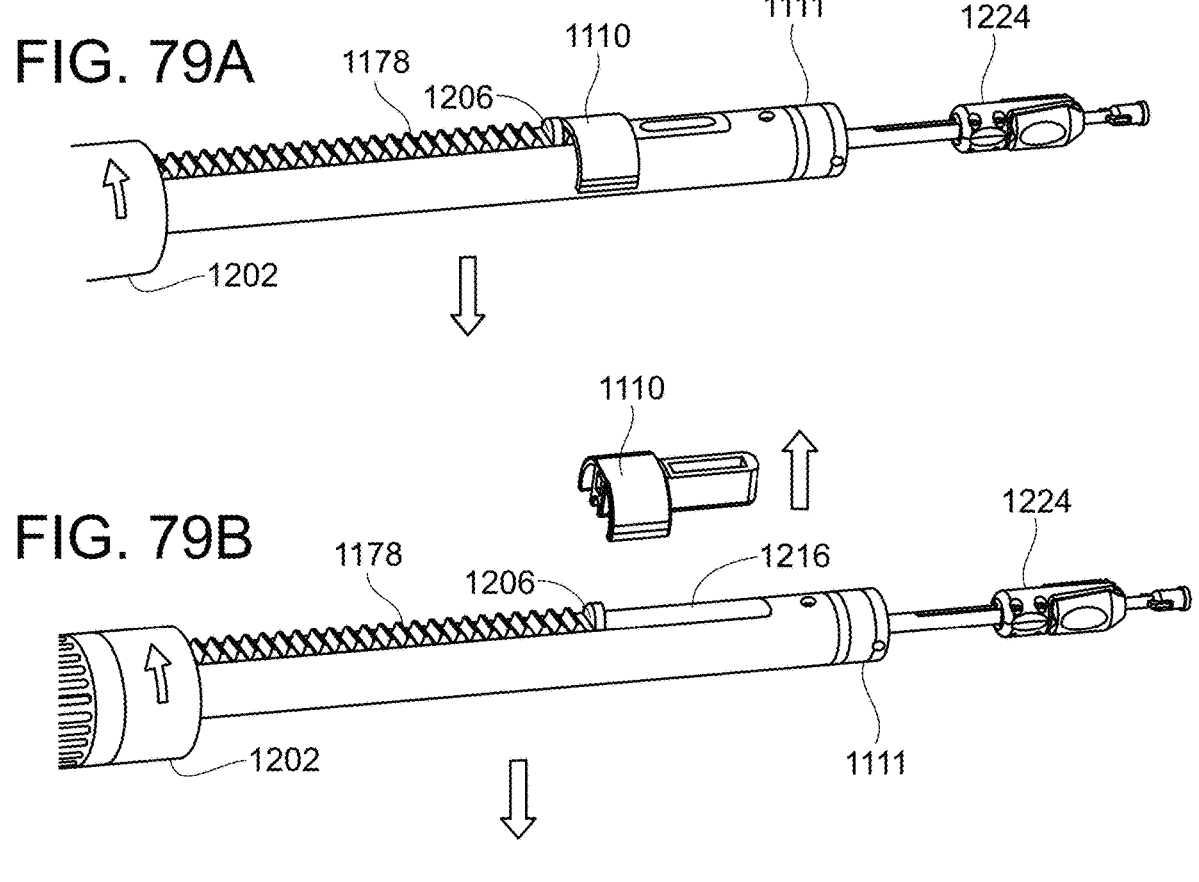
FIG. 79A
FIG. 79B
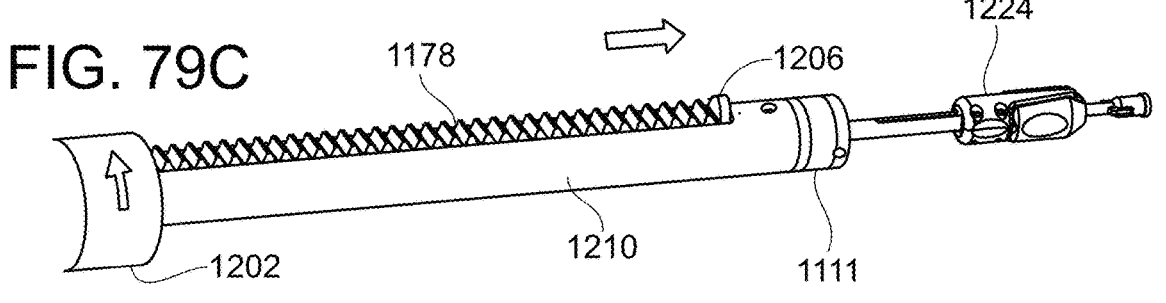
FIG. 79C

AORTIC PROSTHESIS DELIVERY SYSTEM AND METHOD OF USE

CROSS-REFERENCE TO RELATED APPLICATIONS

This application claims the benefit of the following U.S. Provisional Application Nos. 63/111,357, filed Nov. 9, 2020; 63/153,701, filed Feb. 25, 2021; and 63/210,381, filed Jun. 14, 2021, the entire contents of each are incorporated herein by reference.

BACKGROUND OF THE INVENTION

Arterial pathologies, including aortic aneurysms, can be treated by open surgical reconstruction, or alternatively, endovascular repair, which is a minimally invasive alternative to open surgical repair. Optimizing a successful outcome of endovascular repair, however, requires assessment of the patient's anatomy and, in the case of an arterial, or, more specifically, an aortic aneurysm, an appropriate stent spanning the proximal and distal ends of the aneurysm ensures essentially complete exclusion of the aneurysm sac by anchoring of the stent graft in the aorta to minimize endoleaks. Endoleaks and post-surgical enlargement of the aneurysm site often require additional repair to seal any expansion of the aneurysm sac and, generally, must be done without significantly compromising blood flow through the surgical site to surrounding viscera and associated structures.

Therefore, a need exists for new and improved endovascular repair devices and methods to treat arterial pathologies, such as aortic aneurysms.

SUMMARY OF THE INVENTION

The present invention relates to an aortic prosthesis system for use in treating and repairing aortic and other arterial vascular damage, such as vascular damage associated with aortic aneurysms, including aortic aneurysms in regions of the aorta having arterial branches that supply blood to vital organs and tissues, such as thoracic aortic aneurysms, abdominal aortic aneurysms, thoracoabdominal aortic aneurysms, juxtarenal aortic aneurysms and short-neck abdominal aortic aneurysms.

In one embodiment, the invention is an aortic prosthesis system that includes a luminal graft component having a proximal open end and a distal open end. A plurality of stents are distributed longitudinally along the luminal graft component, and at least one of the stents has struts that are joined to define proximal and distal apices. At least one loop is secured to at least one of the struts. At least one ligature extends through the loop and traverses at least a portion of the struts of at least one of the stents. The ligature includes ends that, when linked, at least partially radially constrict each corresponding stent. A pair of anchor loops at the luminal graft component longitudinally span the ends of each associated ligature when linked to radially constrict the corresponding stent.

In another embodiment, the invention is a stent graft delivery system that includes a stent graft. The stent graft includes a luminal graft component having a proximal open end and a distal open end, and defines a lumen. A plurality of stents are distributed longitudinally along the luminal graft component, and at least one of the stents has struts that are joined to define proximal and distal apices. At least one loop is secured to at least one of the struts. At least one ligature extends through the loop and traverses at least a portion of the struts. The ligature includes ends that, when linked, at least partially radially constrict the stent. A pair of anchor loops at the luminal graft component longitudinally span the ends of each associated ligature when linked to radially constrict the corresponding stent. A wire extends longitudinally along the luminal graft component, and through the anchor loops, linking the ligature ends, the ligature thereby radially constricting at least a portion of at least one of the stents of the stent graft, whereby retraction of the wire from the ends of the at least one ligature releases the ends of stent graft from constriction by the at least one ligature.

In still another embodiment, the invention is a method of implanting a stent graft at an arterial aneurysm of a subject. The method includes advancing a stent graft to an arterial aneurysm of the subject, wherein the stent graft includes at least one ligature extending about a periphery of the stent graft, the ligature extending through at least one loop secured to at least one strut of a radial stent of the stent graft and having ends that are linked by a wire extending parallel to a longitudinal axis of the stent graft and through anchor loops longitudinally spanning the linked ends to thereby maintain the stent graft in a radially constricted position. The wire is retracted from the at least one ligature and the anchor loops, consequently releasing the ends of the ligature from each other, whereby the stent graft radially expands from the radially constricted position to a radially expanded position, thereby implanting the stent graft at the arterial aneurysm of the subject.

In yet another embodiment, the invention is an aortic prosthesis system that includes a luminal graft component having a proximal open end and a distal open end. A plurality of stents is distributed longitudinally along the luminal graft component, at least one of the stents having struts that are joined to define proximal and distal apices. At least one loop is secured to at least one of the struts. At least one ligature extends through the loop, each ligature traversing the struts of at least one of the stents, wherein the ligature includes ends that, when linked, at least partially radially constrict each corresponding stent.

In another embodiment, the invention is an aortic prosthesis system that includes a luminal graft component having a proximal open end and a distal open end. A plurality of stents is distributed longitudinally along the luminal graft component, at least one of the stents having struts that are joined to define proximal and distal apices. At least one loop is secured to at least one of the struts. At least one ligature extends through the loop, each ligature traverses a plurality of the struts of the stent to which the loop is attached, whereby the ligature constrains the stent against outward radial expansion to thereby constrict the stent graft.

In still another embodiment, the invention is a delivery system for implanting a stent graft that includes a longitudinal body defining a longitudinal axis having a proximal handle and a distal handle, a guidewire catheter having a proximal end and a distal end, and extending from the distal handle of the longitudinal body, a nose cone fixed at the distal end of the guidewire catheter, the nose cone having a proximal end, and an inner keyed extrusion. The inner keyed extrusion includes a proximal end, a distal end, an internal surface defining a lumen through which the guidewire catheter extends, and an external surface that is non-circular in cross section along at least a portion of the length of the inner keyed extrusion. An apex capture device of this embodiment includes an apex capture device having a distal component at the proximal end of the nose cone, and a proximal component fixed to the distal end of the inner keyed extrusion, the distal component and the proximal component together defining openings that capture proximal apices of a stent at a proximal end of a stent graft prosthesis extending about the inner keyed extrusion in a first position, and that release the proximal apices in a second position of the apex capture device. A torque component of this embodiment includes an outer keyed extrusion fixed to and extending from the proximal handle, and about the inner keyed extrusion, the outer keyed extrusion defining an inner surface that is non-circular in cross-section and that is in interfering relation with axial rotation relative to the inner keyed extrusion, and at least two arms disposed radially about and extending distally from the outer keyed extrusion, each arm being movable from a constricted state to an expanded state, whereby the torque component exhibits radial expansion. A radial constraint that extends about the outer keyed extrusion, whereby a stent graft extending between the outer keyed extrusion and the radial constraint can be captured at a distal end of the stent graft, and whereby application of torque force to the torque component by rotation of the proximal handle about the longitudinal axis causes the stent graft to rotate about the longitudinal axis.

In yet another embodiment, a delivery system for implanting a stent graft includes a proximal handle, a guidewire catheter extending from the proximal handle, and having a proximal end at the proximal handle and a distal end, a nose cone fixed at the distal end of the guidewire catheter, and an inner keyed extrusion. The inner keyed extrusion has a proximal end, a distal end, an internal surface defining a lumen through which the guidewire catheter extends, and an external surface that is non-circular in cross section along at least a portion of the length of the inner keyed extrusion. A stent graft extends about the guidewire catheter includes, a luminal graft component having an outside surface, an inside surface, a proximal open end, a distal open end, and defining a lumen, and a plurality of stents extending longitudinally along the luminal wall. A radial constraint of this embodiment radially constrains the stent graft and extends about the guidewire catheter, wherein the release of the radial constraint allows radial expansion of the stent graft to the thereby at least partially deploy the stent graft. An apex capture device of this embodiment includes a distal component at the proximal end of the nose cone, and a proximal component fixed to the distal end of the inner keyed extrusion, the distal component and the proximal component together defining openings that capture proximal apices of a stent at a proximal end of a stent graft prosthesis extending about the inner keyed extrusion in a first position, and that release the proximal apices in a second position of the apex capture device. A torque component of this embodiment of the invention extends about the guidewire catheter, the torque component including an outer keyed extrusion extending distally from the proximal handle and about the inner keyed extrusion, the outer keyed extrusion defining an inner surface that is non-circular in cross-section and that is in interfering relation with axial rotation relative to the inner keyed extrusion, and at least two arms disposed radially about and extending distally from the outer keyed extrusion, each arm being moveable from a constricted state to an expanded state, whereby the torque component exhibits radial expansion, and whereby application of torque force to the torque component by rotation of the proximal handle about the longitudinal axis causes the stent graft to rotate about the longitudinal axis.

In another embodiment of the invention, a method of implanting a stent graft at an aneurysm site of a subject includes the step of directing a stent graft to an aneurysm site of the subject, the stent graft being held in a constricted position by a radial constraint, and extending circumferentially about an inner keyed extrusion that extends distally about a guidewire catheter and from a distal handle of a longitudinal body of a delivery device and is within the stent graft, the stent graft having a proximal end and a distal end, and wherein the distal end of the stent graft is rotationally fixed relative to a torque component, the torque component including an outer keyed extrusion extending about the inner keyed extrusion, the outer keyed extrusion defining an inner surface that is non-circular in cross-section and that is in interfering relation with axial rotation relative to the inner keyed extrusion, and at least two arms and extending distally and radially from the keyed extrusion, each arm being moveable from a constricted state to an expanded state, whereby the torque component exhibits radial expansion. The proximal handle of the longitudinal body is rotated to thereby rotate the outer keyed extrusion and rotationally align the stent graft within the aneurysm site. The outer keyed extrusion is rotated to rotate the outer keyed extrusion, whereby a proximal component of an apex capture device fixed to a distal end of the outer keyed extrusion separates from a distal component of the apex capture device fixed to a distal end of the guidewire catheter, thereby releasing a stent at a proximal end of the stent graft that is captured by the apex capture device. The radial constraint is retracted, thereby releasing the stent graft at the aneurysm site. The guidewire catheter and the torque component are retracted from the subject, thereby implanting the stent graft at the aneurysm site of the subject.

In yet another embodiment of the invention, a method of implanting a stent graft at an aneurysm site of a subject includes the steps of advancing a stent graft that is maintained in a constricted state by a radial constraint to an aneurysm site, rotationally aligning the stent graft by rotation of the stent graft with at least partial assistance of a torque component at a distal end of the stent graft and that is keyed to an apex capture device that captures a stent at a proximal end of the stent graft, retracting an inner keyed extrusion having a proximal component of the apex capture device secured to a distal end of the apex capture device, thereby releasing the stent at the proximal end of the stent graft, and removing the radial constraint from the stent graft, thereby implanting the stent graft at the aneurysm site.

In still another embodiment, the invention is a delivery system for implanting a stent graft that includes, a proximal handle, a guidewire catheter extending from the proximal handle, and having a proximal end at the proximal handle and a distal end, and a nose cone fixed at the distal end of the guidewire catheter. An inner keyed extrusion of this embodiment includes a proximal end, a distal end, an internal surface defining a lumen through which the guidewire catheter extends, and an external surface that is non-circular in cross section along at least a portion of the length of the inner keyed extrusion. A stent graft of this embodiment extends about the guidewire catheter, the stent graft including, a luminal graft component having an outside surface, an inside surface, a proximal open end, a distal open end, and defining a lumen, and a plurality of stents extending longitudinally along the luminal graft component. An apex capture device of this embodiment includes a distal component at the proximal end of the nose cone, and a proximal component fixed to the distal end of the inner keyed extrusion, the distal component and the proximal component together defining openings that capture proximal apices of a stent at a proximal end of a stent graft prosthesis extending about the inner keyed extrusion in a first position, and that release the proximal apices in a second position of the apex capture device. A radial constraint at the stent graft includes at least one ligature traversing at least a portion of the struts of the stents of the stent graft, the ligature including ends that, when linked, at least partially radially constrict the stents. A wire extends longitudinally along the luminal graft component and links the ligature ends, thereby radially constricting at least a portion of the stents of the stent graft, whereby retraction of the wire from the ends of the at least one ligature releases the radial constriction by the at least one ligature. A torque component of this embodiment extends about the guidewire catheter and includes an outer keyed extrusion fixed to and extending from the proximal handle, and about the inner keyed extrusion. The outer keyed extrusion defines an inner surface that is non-circular in cross-section and is in interfering relation with axial rotation relative to the inner keyed extrusion. At least two arms are disposed radially about and extending distally from the outer keyed extrusion, each arm being moveable from a con-stricted state to an expanded state, whereby the torque component exhibits radial expansion, and whereby applica-tion of torque force to the torque component by rotation of the proximal handle and the outer keyed extrusion about the longitudinal axis causes the stent graft to rotate about the longitudinal axis.

In yet another embodiment of the invention, a delivery system for implanting a stent graft includes a proximal handle, a guidewire catheter extending from the proximal handle and having a proximal end at the proximal handle and a distal end, a nose cone fixed at the distal end of the guidewire catheter, the nose cone having a proximal end and a distal end. An inner keyed extrusion of this embodiment includes a proximal end, a distal end, an internal surface defining a lumen through which the guidewire catheter extends, and an external surface that is non-circular in cross section along at least a portion of the length of the inner keyed extrusion. A stent graft of this embodiment extends about the guidewire catheter and includes a luminal graft component having an outside surface, an inside surface, a proximal open end, a distal open end, and defining a lumen. A plurality of stents extends longitudinally along the luminal graft component, and a bare stent is at the proximal open end of the luminal graft component. The bare stent includes struts defining proximal and distal apices, wherein the bare stent is fixed to the luminal graft component at the distal apices of the bare stent. A radial constraint of this embodi-ment at the stent graft includes at least one ligature travers-ing at least a portion of the struts of the stents of the stent graft, the ligature including ends that, when linked, at least partially radially constrict the stents. A wire of this embodi-ment extends longitudinally along the luminal graft compo-nent and linking the ligature ends, thereby radially constrict-ing at least a portion of the stents of the stent graft, whereby retraction of the wire from the ends of the at least one ligature releases the radial constriction by the at least one ligature. An apex capture device of this embodiment at the distal end of the guidewire catheter, the releasably captures the proximal apices of the bare stent, and includes a distal component at the proximal end of the nose cone, and a proximal component fixed to the distal end of the inner keyed extrusion. The distal component and the proximal component together define openings that capture proximal apices of a stent at a proximal end of the stent graft prosthesis extending about the inner keyed extrusion in a first position, and release the proximal apices in a second position of the apex capture device. A torque component of this embodiment of the invention extends about the guidewire catheter and includes an outer keyed extrusion extending distally from the proximal handle about the inner keyed extrusion, the outer keyed extrusion defining an inner surface that is non-circular in cross-section and this in interfering relation with axial rotation relative to the inner keyed extrusion, and at least two arms disposed radially about and extending distally from the outer keyed extrusion, each arm being moveable from a constricted state to an expanded state, whereby the torque component exhibits radial expansion, and whereby application of torque force to the torque component by rotation of the proximal handle and the outer keyed extrusion about the longitudinal axis causes the stent graft to rotate about the longitudinal axis.

In still another embodiment, the invention is method of implanting a stent graft at an aneurysm of a subject that includes the step of directing a stent graft to an aneurysm of the subject, the stent graft including a luminal graft com-ponent and a plurality of radial stents distributed longitudi-nally along the luminal graft component, at least one of the stents having struts that are joined to define proximal and distal apices, the stent graft being held in a constrained position by a radial constraint, the radial constraint including at least one ligature traversing at least a portion of the struts of the stents of the stent graft, the ligature including ends that, when linked, at least partially radially constrict the stents, the radial constraint also including a wire extending longitudinally along the luminal graft component and link-ing the ligature ends and thereby radially constricting at least a portion of the stents of the stent graft, whereby retraction of the wire from the ends of the at least one ligature releases the radial constriction by the at least one ligature; and extending circumferentially about a guidewire catheter that extends distally from a distal handle of a longitudinal body of a delivery device and is within the stent graft, the stent graft having a proximal end and a distal end, and wherein the distal end of the stent graft is rotationally fixed relative to a torque component fixed to a outer keyed extrusion that extends proximally from a proximal handle and circumfer-entially about an inner keyed extrusion that extends bout a guidewire catheter and within the stent graft, the guidewire catheter and the inner keyed extrusions each including one component of a two-component apex capture device at their distal ends, and wherein the inner keyed extrusion includes a non-circular cross-section and the outer keyed extrusion includes a non-circular cross-section that is in interfering relation with rotation relative to the inner keyed extrusion. A proximal handle of the longitudinal body is rotated in this method to thereby rotate the outer keyed extrusion the apex capture device to rotationally align the stent graft within the aneurysm site. The outer keyed extrusion is retracted, thereby separating the two components of the apex capture device and releasing a stent at a proximal end of the stent graft. The torque component is retracted, thereby releasing the stent graft at the aneurysm site The radial constraint and the guidewire catheter are then retracted from the subject, thereby implanting the stent graft at the aneurysm site of the subject.

In yet another embodiment, the invention is a delivery system for implanting a stent graft that includes a longitu-dinal body defining a longitudinal axis and having a proxi-mal handle and a distal handle, a guidewire catheter having a proximal end and a distal end, and extending from the distal handle of the longitudinal body, and an inner keyed extrusion. The inner keyed extrusion includes a proximal end, a distal end, an internal surface defining a lumen through which the guidewire catheter extends, and an external surface that is non-circular in cross section along at least a portion of the length of the inner keyed extrusion. A stent graft extends about the guidewire catheter and includes a luminal graft component having an outside surface, an inside surface, a proximal surface, a proximal open end, a distal open end, and defining a lumen. A plurality of stents extend longitudinally along the luminal graft component and include struts that join at their opposite ends to define apices. A radial constraint of this embodiment is at a stent graft and includes at least one loop fixed to at least a portion of the struts of the stents, and at least one ligature traversing at least one of the stents and through the loops fixed to the struts of the stents. An apex capture device of this embodiment is at the distal end of the guidewire catheter and releasably captures the proximal apices of the bare stent. The apex capture device includes a distal component at the proximal end of the nose cone, and a proximal component fixed to the distal end of the inner keyed extrusion, the distal component and the proximal component together defining openings that capture proximal apices of a stent at a proximal end of the stent graft prosthesis extending about the inner keyed extrusion in a first position, and that release the proximal apices in a second position of the apex capture device. A torque component, includes an outer keyed extrusion extending distally from the proximal handle about the inner keyed extrusion, the outer keyed extrusion defining an inner surface that is non-circular in cross-section and that is in interfering relation with axial rotation relative to the inner keyed extrusion, and at least two arms disposed radially about and extending distally from the outer keyed extrusion, each arm being moveable from a constricted state to an expanded state, whereby the torque component exhibits radial expansion, and whereby application of torque force to the torque component by rotation of the proximal handle outer keyed extrusion about the longitudinal axis causes the stent graft to rotate about the longitudinal axis.

In another embodiment, the invention is a stent graft delivery system that includes: a handle; an internal lead screw assembly; a lead screw nut; a support member fixed to the handle body and extending through the internal lead screw assembly; a slider about the support member and releasably fixed to the internal lead screw assembly; an introducer sheath extending about a portion of the support member and distally from the slider, and fixed to the slider; a leg clasp fixed to the support tube and extending distally from the support tube; and a removable leg stop in a slot of the handle and proximal to internal lead screw assembly. The handle includes a distal grip and a handle body extending proximally from one end of the distal grip. The handle defines a conduit and a slot along a portion of the length of the distal grip and the handle body, the handle body defining a longitudinal axis. The internal lead screw assembly is within the handle body, and is movable along a major axis of the conduit. The internal lead screw assembly also includes a threaded portion that extends through the slot and defines an opening essentially coaxial with the longitudinal axis of the handle. The lead screw nut extends about the handle body and is threadably engaged with the threaded portion of the internal lead screw assembly, whereby rotation of the lead screw nut while abutting the distal grip causes movement of the internal lead screw assembly relative to the handle and wherein the lead screw nut simultaneously is slidable along the handle body while engaged with the internal lead screw assembly, thereby providing at least two mechanisms for causing movement of the internal lead screw relative to the handle. The support member includes a support tube extending through the handle body, and a hypo-tube extending about a circumference of the support tube. The slider includes a hemostasis valve. The introducer sheath is fixed to the slider, whereby relative movement of the handle body and the lead screw assembly causes movement of the introducer sheath relative to the support member. The leg clasp includes: a barrel portion fixed to the support tube; a spool portion extending distally from the barrel portion along the longitudinal axis, the spool portion having a diameter less than that of the barrel portion; and a rim portion at an end of the spool portion, the rim portion having a diameter greater than that of the spool portion and less than that of the barrel portion. The removable leg stop includes a leg stop body having a longitudinal axis and within the slot of the handle body proximal to the internal lead screw assembly, and flexible wings extending radially from the longitudinal axis of the leg stop body. The wings extend at least partially around the handle body, whereby the leg stop body is held in place in the slot of the handle body, the leg stop body being removable from the slot by distending the flexible wings from around the handle body.

This invention has many advantages. For example, loops attached to struts of stents according to the invention provide improved control by the physician during implantation. More specifically, the loops through which a constraining ligature pass, by being fixed to struts of stents of a stent graft being implanted enable the physician to better rotate or reposition the stent graft after it has been partially deployed to align a fenestration in the stent graft with a branch vessel. Also, the physician can partially retract the wire radially constricting stents of the stent graft, thereby providing greater control over delivery systems that are only able to position the stent graft before deployment begins. Further, the physician can rotate the stent graft after it has been partially deployed, such as by only partially removing the radial constraint. Further, the torque component enables torque to be transmitted to the distal end of a stent graft during delivery, thereby providing greater control over delivery systems that are only able to apply torque to a proximal end of a stent graft. As a consequence, a stent graft can be deployed at a surgical site with more accuracy, less risk of injury to the vasculature of the subject, and without significant risk of distorting the intended shape of the stent graft when implanted at the surgical site.

As a consequence, a stent graft can be deployed at a surgical site with more accuracy, less risk of injury to the vasculature of the subject, and without significant risk of distorting the intended shape of the stent graft when implanted at the surgical site.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments. The same number present in different figures represents the same item.

FIG. 2A is a side view of the stent graft shown in FIGS. 1A-1F, following retraction of the wire linking ligatures holding the stent graft in a radially constricted position.

FIG. 2B is an end view of the proximal end of the stent graft in an unconstricted position, as shown in FIG. 2A, taken along line 2B-2B, and having an expanded diameter D".

FIG. 2C is a side view of the proximal end of the stent graft shown in FIG. 2B, taken along line 2C-2C.

FIG. 2D is a side view of the proximal end of the stent graft shown in cross-section in 2B, taken along line 2D-2D.

FIG. 2E is a side view of the proximal end of the stent graft shown in FIG. 2A and shown in cross-section in FIG. 2B, taken along line 2E-2E.

FIG. 2F is a side view of the proximal end of the stent graft shown in FIG. 2B taken along line 2F-2F.

FIG. 3A is another embodiment of an aortic prosthesis delivery system of the invention, wherein a stent graft is held in a radially constricted position by a ligature that extends through loops that are secured to struts of a stent of the aortic prosthesis delivery system, wherein the stent graft is held in a radially constricted position by a wire stabilized by anchor loops, and wherein the ligatures are also stabilized by ligature loops distributed laterally on either side of the wire.

FIG. 3B is an end view of the stent graft delivery system shown in FIG. 3A, taken along line 3B-3B, showing the stent graft as having a constricted diameter D'.

FIG. 3C is a side view of the proximal end of stent graft shown in FIG. 3B, taken along line 3C-3C.

FIG. 3D is a side view of the proximal end of the stent graft shown in FIG. 3B, taken along line 3D-3D.

FIG. 3E is a side view of the proximal end of the stent graft shown in FIG. 3B, taken along line 3E-3E.

FIG. 3F is a side view of the proximal end of the stent graft shown in FIG. 3B, taken along line 3F-3F.

FIG. 4A is a side view of the stent graft of the aortic prosthesis delivery system shown in FIGS. 3A-3F, following retraction of the wire component of the aortic prosthesis delivery system from end loops of the ligatures and from the anchor loops, thereby causing stent graft to expand in diameter to an expanded position.

FIG. 4B is an end view of the stent graft as shown in FIG. 4A, taken along lines 4B-4B, having an expanded diameter D".

FIG. 4C is a side view of the proximal end of the stent graft shown in FIG. 4B, taken along line 4C-4C.

FIG. 4D is a side view of the proximal end of the stent graft shown in FIG. 4B, taken along line 4D-4D.

FIG. 4E is a side view of the proximal end of the stent graft shown in FIG. 4B, taken along line 4E-4E FIG. 4F is a side view of the proximal end of the stent graft shown in FIG. 4B, taken along line 4F-4F.

FIG. 5A is a side view of another embodiment of the aortic prosthesis delivery system of the invention, wherein ligatures extend through loops fixed to struts of stents of the stent graft but do not completely encompass the stent graft when the prosthesis is in a radially constricted position.

FIG. 5B is an end view of the aortic prosthesis delivery system shown in FIG. 5A, taken along line 5B-5B, showing the stent graft having a constricted diameter D'.

FIG. 5C is a side view of the proximal end of the stent graft shown in FIG. 5B, taken along line 5C-5C.

FIG. 5D is a side view of the proximal end of the stent graft shown in FIG. 5B, taken along line 5D-5D.

FIG. 5E is a side view of the proximal end of the stent graft shown in FIG. 5B, taken along line 5E-5E.

FIG. 5F is a side view of the proximal end of the stent graft shown in FIG. 9B, taken along line 5F-5F.

FIG. 6A is a side view of the stent graft of the aortic prosthesis delivery system shown in FIGS. 5A-5F, following retraction of the wire linking ends of the ligature to hold the stent graft in a radially constricted position, wherein retraction of the wire from the anchor loops causes the stent graft to radially expand to an expanded diameter.

FIG. 6B is an end view of the proximal end of the stent graft shown in FIG. 6A, taken along line 6B-6B, showing the diameter of the radially expanded stent graft as D".

FIG. 6C is a side view of the proximal end of the stent graft shown in FIG. 6B, taken along line 6C-6C.

FIG. 6D is a side view of the proximal end of the stent graft shown in FIG. 6B, taken along line 6D-6D.

FIG. 6E is a side view of the proximal end of the stent graft shown in FIG. 6 taken along line 6E-6E.

FIG. 6F is a side view of the proximal end of the stent graft shown in FIG. 6B, taken along line 6F-6F.

FIG. 7A is a side view of yet another embodiment of an aortic prosthesis delivery system of the invention, wherein ligatures radially constricting the stent graft are circular and extend about the periphery of the stent graft and through loops fixed to struts of the stents of the stent graft, and wherein diametrically opposed points of the ligatures are linked by a wire that is stabilized by anchor loops.

FIG. 7B is an end view of the aortic prosthesis delivery system of FIG. 7A, taken along line 7B-7B, and having diameter D'.

FIG. 7C is a side view of the proximal end of the stent graft shown in FIG. 7B taken along line 7C-7C.

FIG. 7D is a side view of the proximal end of the stent graft shown in FIG. 7B taken along line 7D-7D.

FIG. 7E is a side view of the proximal end of the stent graft shown in FIG. 7B taken along line 7E-7E.

FIG. 7F is a side view of the proximal end of the stent graft shown in FIG. 7B taken along line 7F-7F.

FIGS. 21A and 21B are views taken along lines AA and BB, respectively, of FIG. 21, showing that the periphery of the fenestration is raised from an external surface of the stent graft.

FIG. 21C is a detail of FIG. 21A.

FIG. 21D is detail of FIG. 21B.

FIGS. 22A and 22B are profiles of the detail of FIG. 22 taken along lines AA and BB, respectively, of FIG. 22.

FIG. 58 is a cross-section of the embodiment of FIGS. 54, 55, 56, and 57, following complete retraction of the wire from the ligatures holding the stent graft in the second intermediate radially-expanded position, thereby causing the stent graft to be in a fully radially-expanded position, although still captured at proximal and distal ends of the stent graft by the delivery device.

FIG. 59 is a cross-section of the embodiment of FIGS. 54, 55, 56, 57, and 58, following actuation of an apex capture component of the delivery device of the invention.

FIG. 60 is a cross-section of the embodiment of FIGS. 54, 55, 56, 57, 58, and 59, following retraction of a torque component of the delivery device of the invention, thereby fully releasing and deploying the stent graft from the delivery device.

FIG. 61 is a cross-section of the embodiment of FIGS. 54, 55, 56, 57, 58, 59, and 60, during removal of the delivery device from the deployed stent graft.

FIG. 62 is a side view of another embodiment of the invention including fenestrated bifurcated stent graft in combination with a delivery system.

FIG. 63 is a perspective view of one embodiment of a leg clasp of the invention and suitable for use with the invention.

FIG. 64 is a cross-sectional view of the leg clasp of FIG. 63 while clasping a leg of a bifurcated stent graft according to one embodiment of the invention.

FIG. 65 is a perspective view of a combination of an introducer sheath, a leg clasp, a push rod (or support tube), and an outer control tube of the invention, with a wire extending through an opening in the push rod.

FIG. 66 is a perspective view of an apex capture device of a delivery device of the invention.

FIG. 67 is a side view of an example of a bifurcated stent graft that is suitable for implantation by the delivery device of the invention, following implantation.

FIG. 68 is a perspective view of an apex capture device suitable for use as a component of a delivery device of the invention, wherein a proximal apex capture portion has been partially retracted from a distal apex capture portion of the apex capture device, thereby releasing proximal apices and barbs of a bare stent of the bifurcated stent graft shown in FIG. 67.

FIG. 69 is a perspective view of the apex capture device shown in FIG. 68 prior to retraction of the proximal apex capture component to expose the proximal apices and barbs of the proximal bare stent of the bifurcated stent graft shown in FIG. 67.

Figure 68:
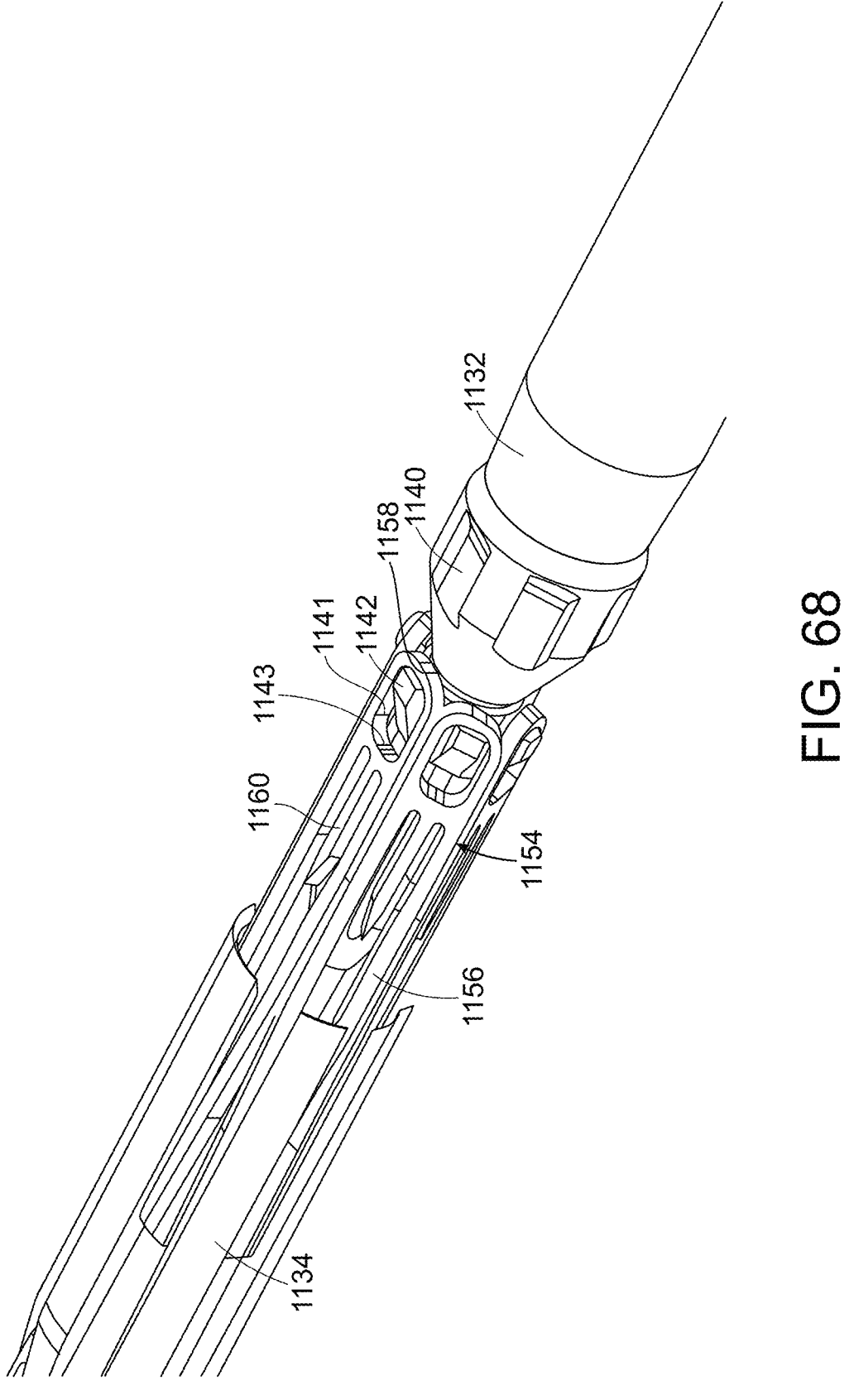
Figure 70:
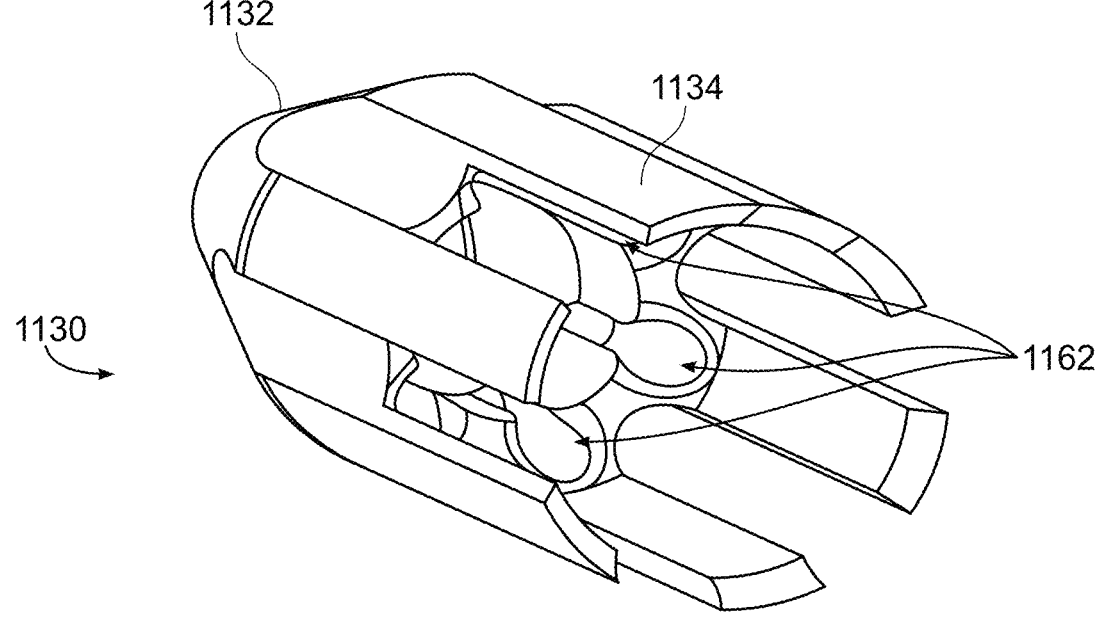

FIG. 70 is a perspective view of a proximal apex capture portion of the apex capture device shown in FIG. 68.

Figure 71:
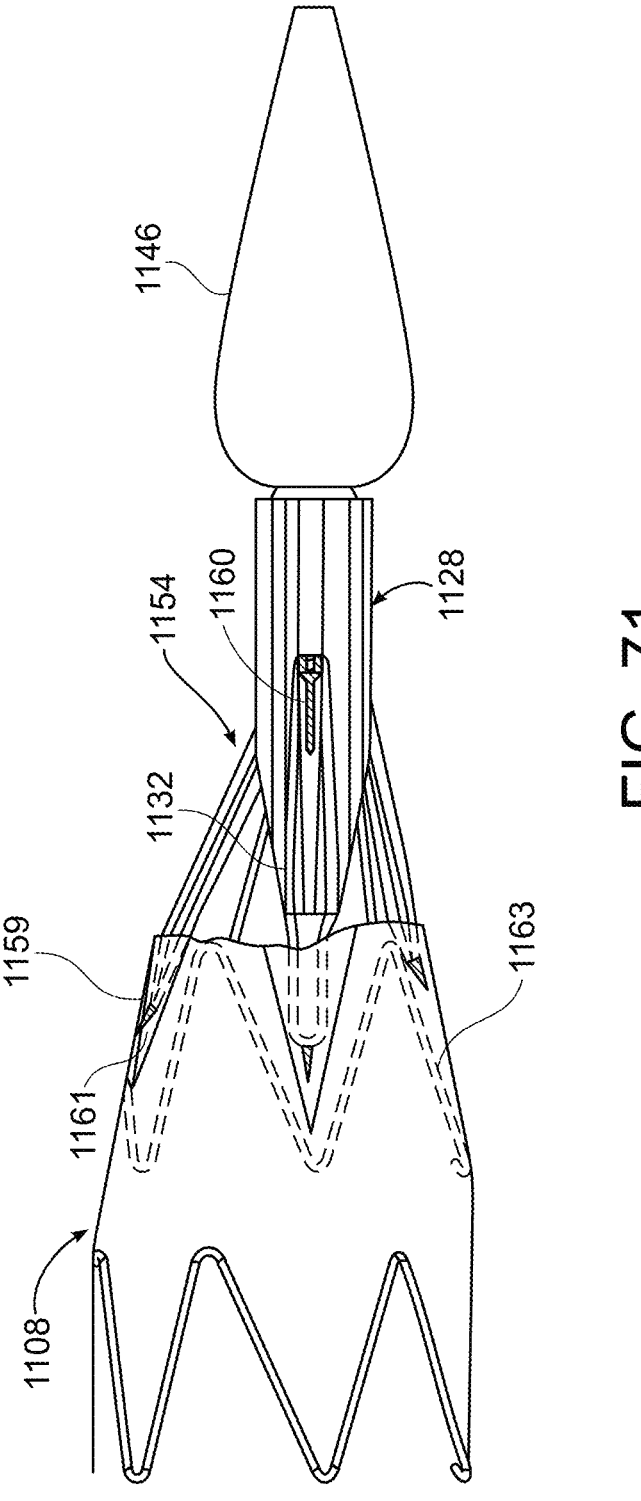

FIG. 71 is a side view of a distal end of a delivery device of the invention while holding in a captured state a proximal end of a stent graft suitable delivery by the delivery device of the invention.

Figures 72, 72A, 72B:
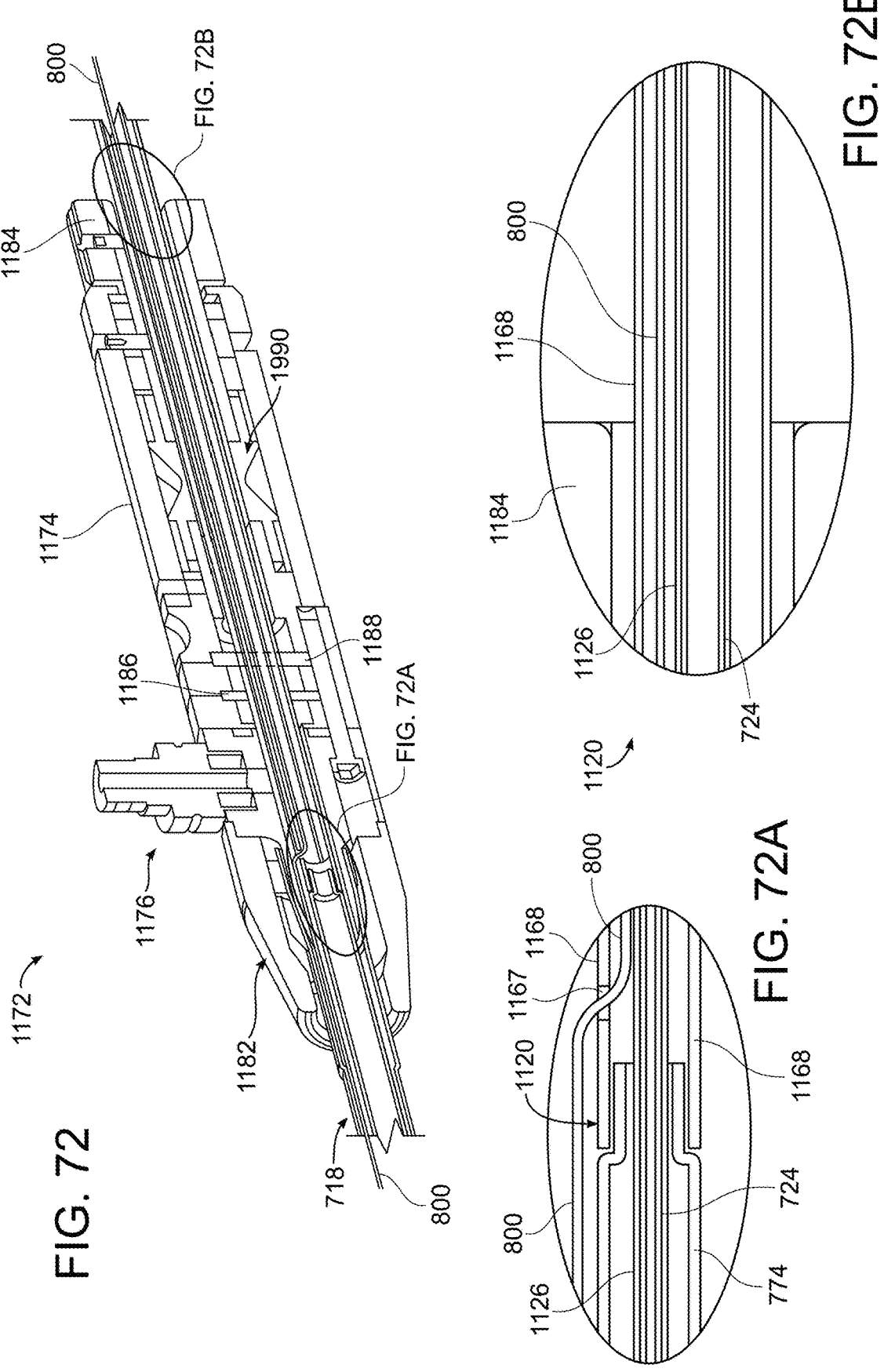

FIG. 72 is a perspective view of a slider suitable for use with the delivery device of the invention, wherein other components of the delivery device extend through the slider prior to release of a bifurcated stent graft at a surgical site.

FIG. 72A is a detail of the distal end of the slider and, specifically, the transition of a wire from running along an outside surface of a pushrod component of the support member to an inside surface of the hypo-tube component of the support member.

FIG. 72B is a detail of the representation of FIG. 72 showing the hypo-tube of the support member extending proximally from the slider.

Figure 73:
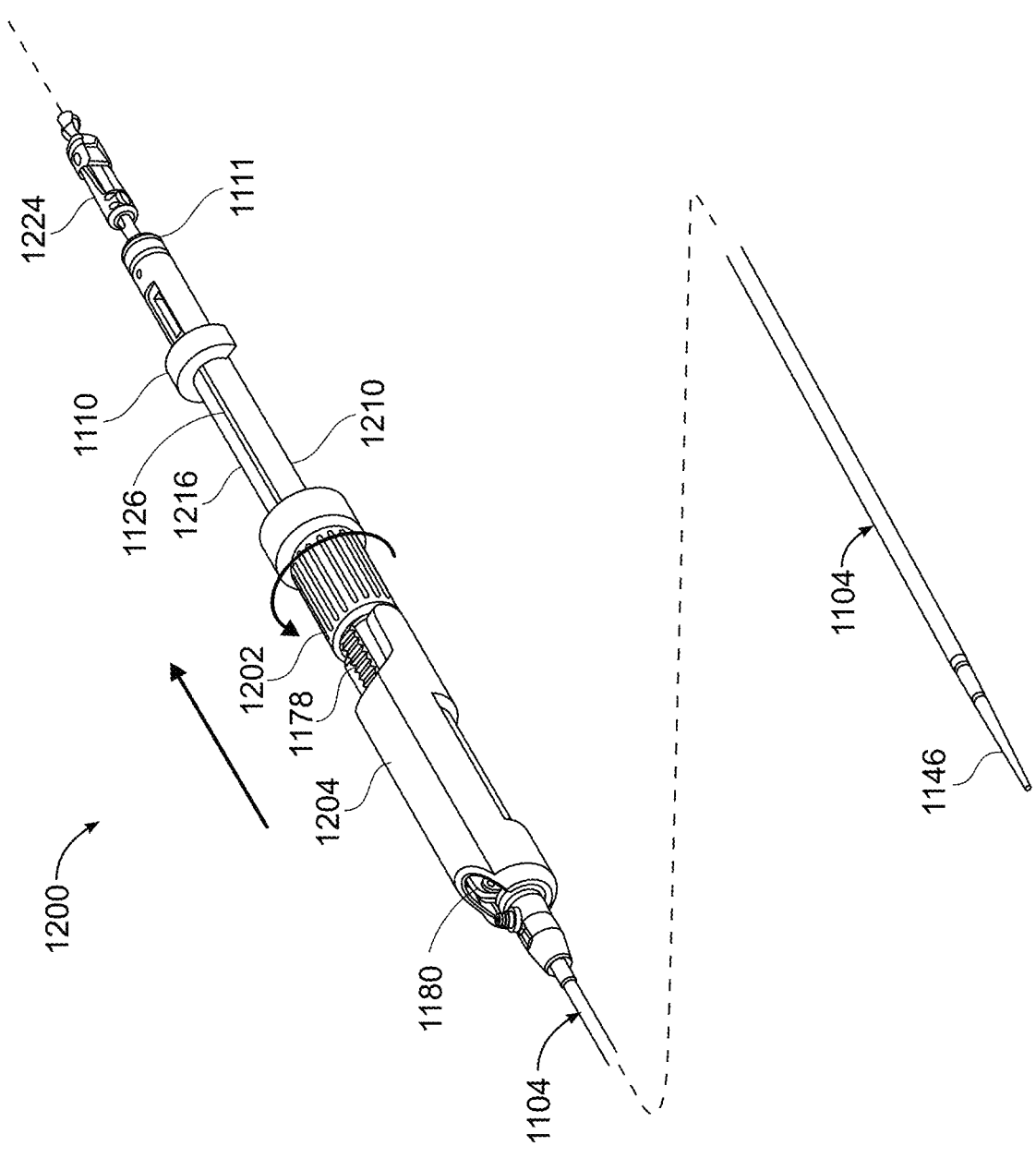

FIG. 73 is a perspective view of one embodiment of the invention, showing the delivery device in a position prior to deployment of a stent graft, such as a bifurcated stent graft.

Figure 74:
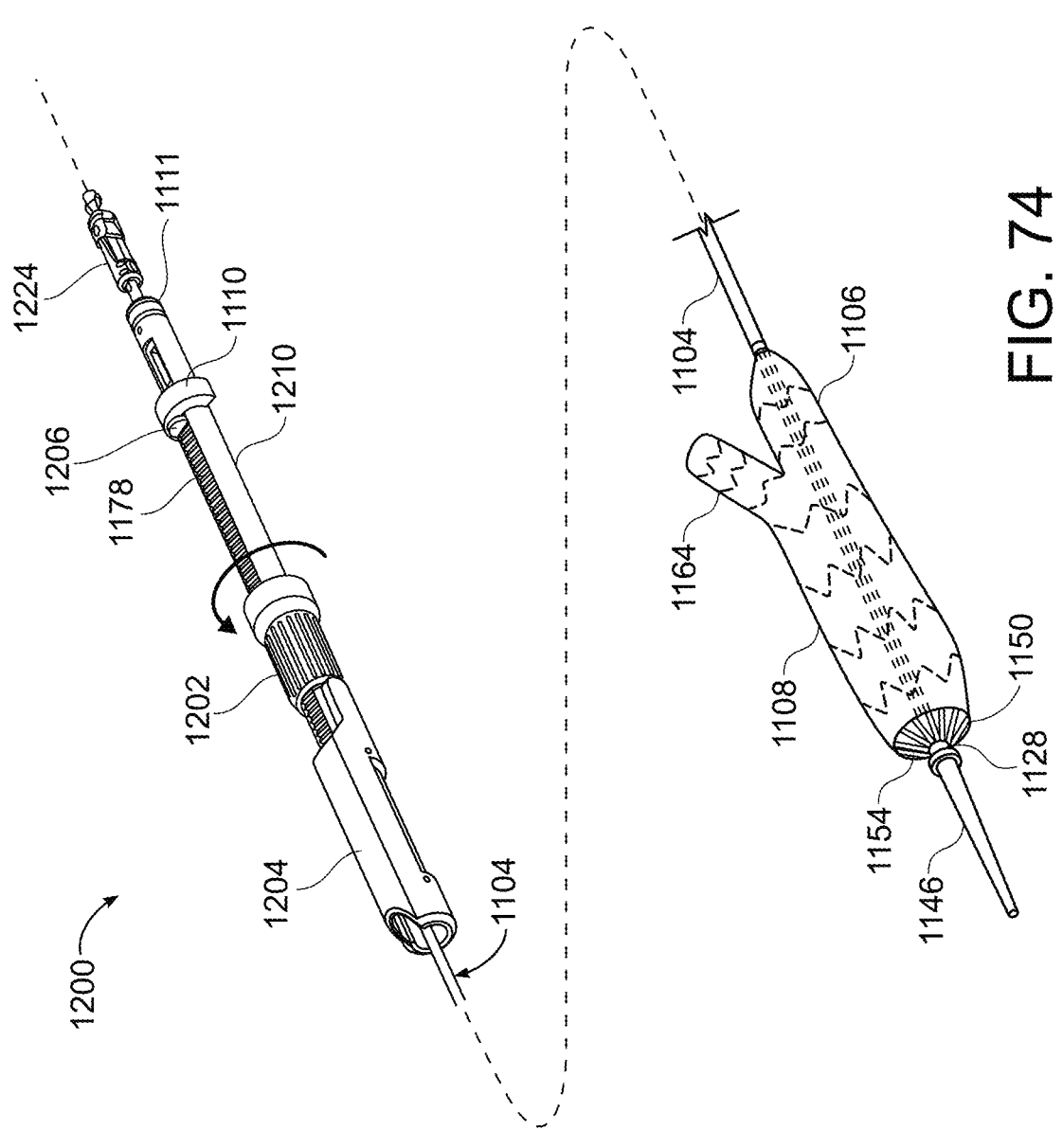

FIG. 74 is a perspective view of the embodiment of the invention shown in FIG. 73, following retraction of an introducer sheath of the delivery device from all of the stent graft except one leg, which is held in place between a leg clasp and the introducer sheath.

Figure 75:
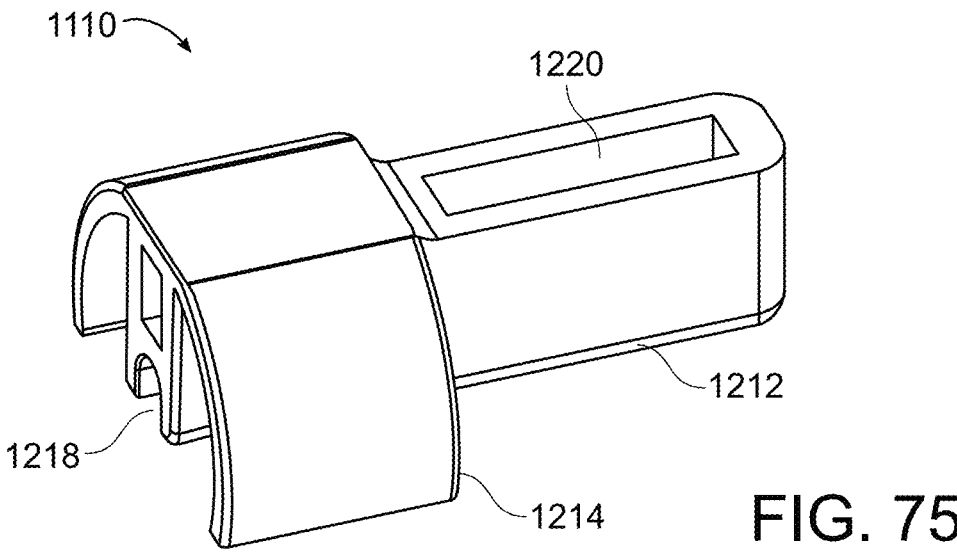

FIG. 75 is one perspective view of an embodiment of a leg stop component of the delivery device of the invention.

Figure 76:
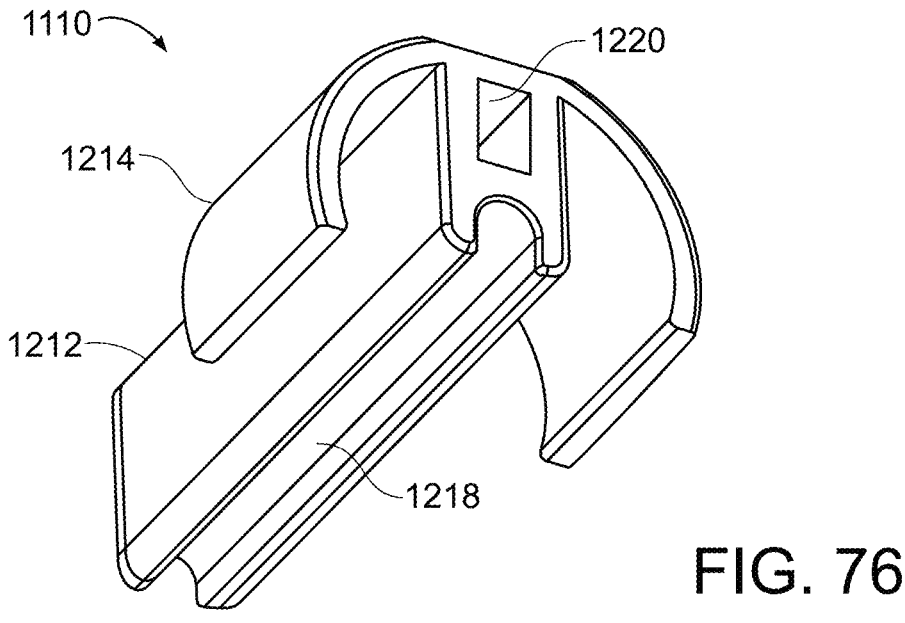

FIG. 76 is another perspective view of the leg clasp shown in FIG. 75.

Figures 77A, 77B, 77C:
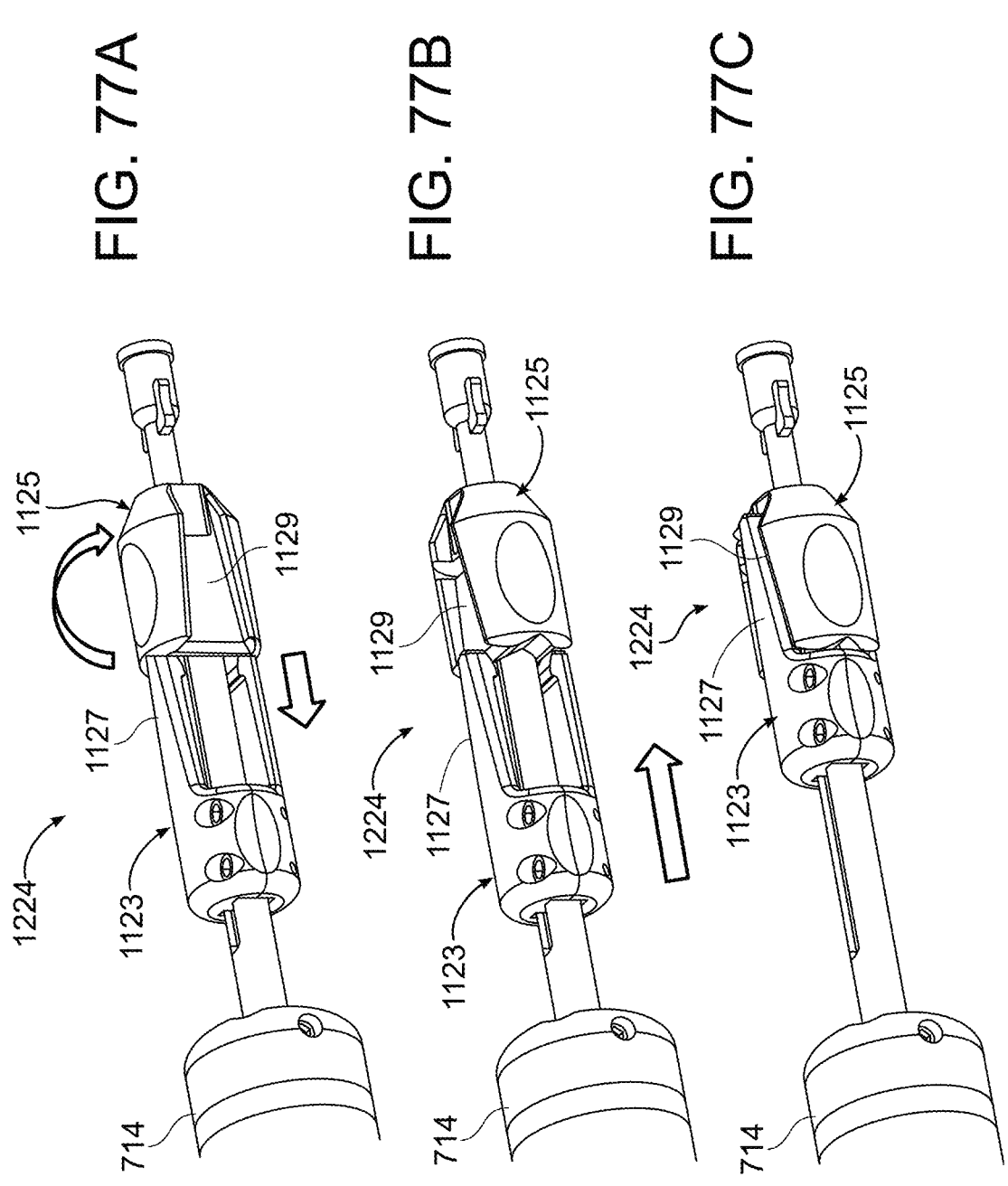

FIG. 77A is a perspective view of a clasp for releasing a bare stent of a stent graft by use of a delivery device of the invention, wherein the clasp is in a position that captures the bare stent.

FIG. 77B is a perspective view of the clasp of FIG. 77A, following reorientation of the clasp to allow release of the bare stent.

FIG. 77C is a perspective view of the clasp of FIGS. 77A and 77B, following actuation and consequent release of the bare stent of the stent graft delivered by the delivery system of the invention.

Figure 78:
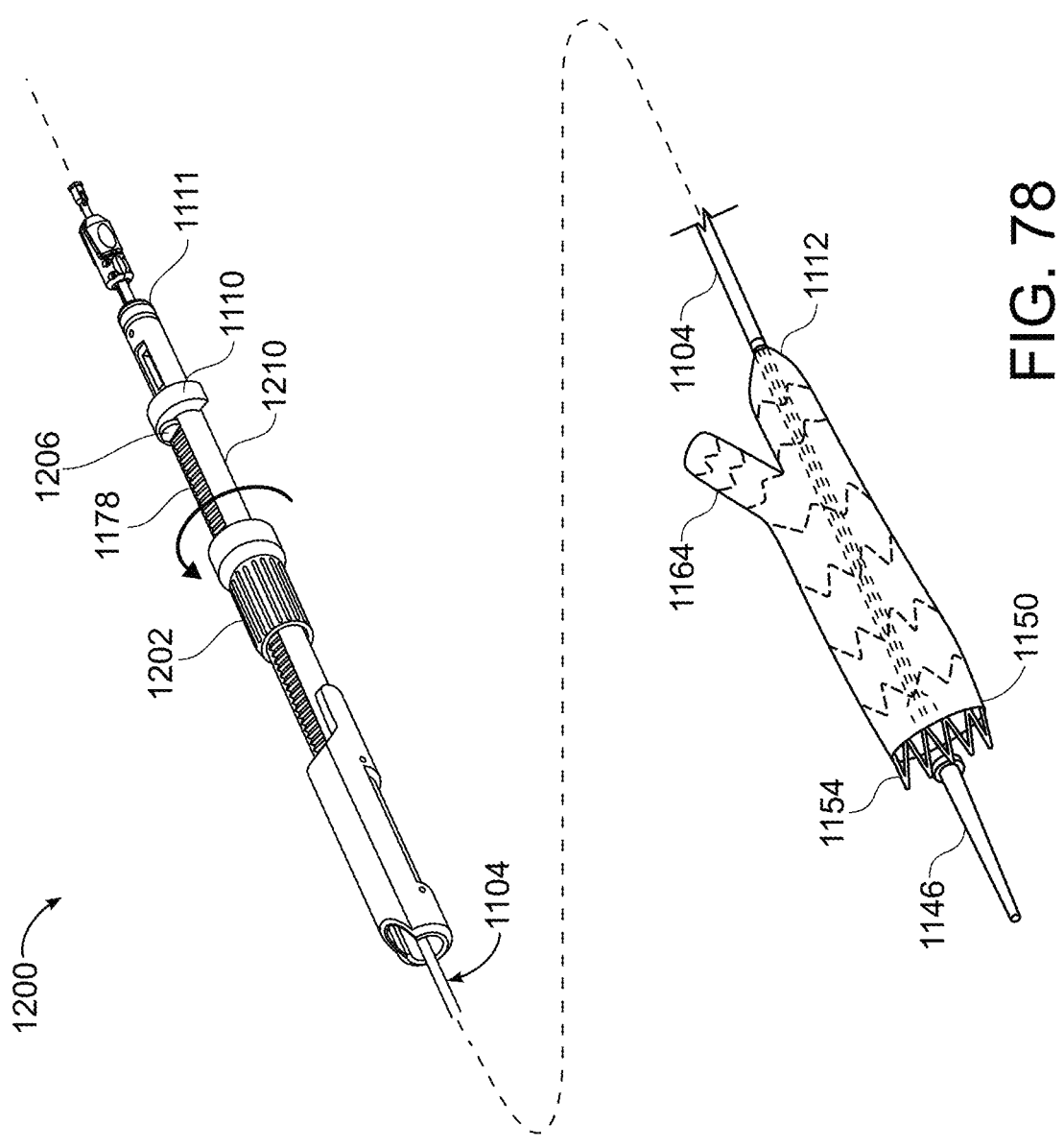

FIG. 78 is a perspective view of the delivery device of FIGS. 73 and 74 upon release of the bare stent from the apex capture device by actuation of the clasp shown in FIGS. 77A through 77B.

FIG. 79A is a detail in perspective of the delivery device of FIGS. 73, 74, and 78, while a leg of a bifurcated stent is still being held by a leg clasp component of the delivery device of the invention, following partial retraction of the introducer sheath from the stent graft, and after actuation of the clasp to release the bare stent of the stent graft.

FIG. 79B is a perspective detail of FIG. 79A following removal of the leg stop component of the delivery device of the invention.

FIG. 79C is a perspective detail of FIGS. 79A and 79B following complete retraction of the introducer sheath from the stent graft, thereby completing release and implantation of the stent graft.

Figure 80:
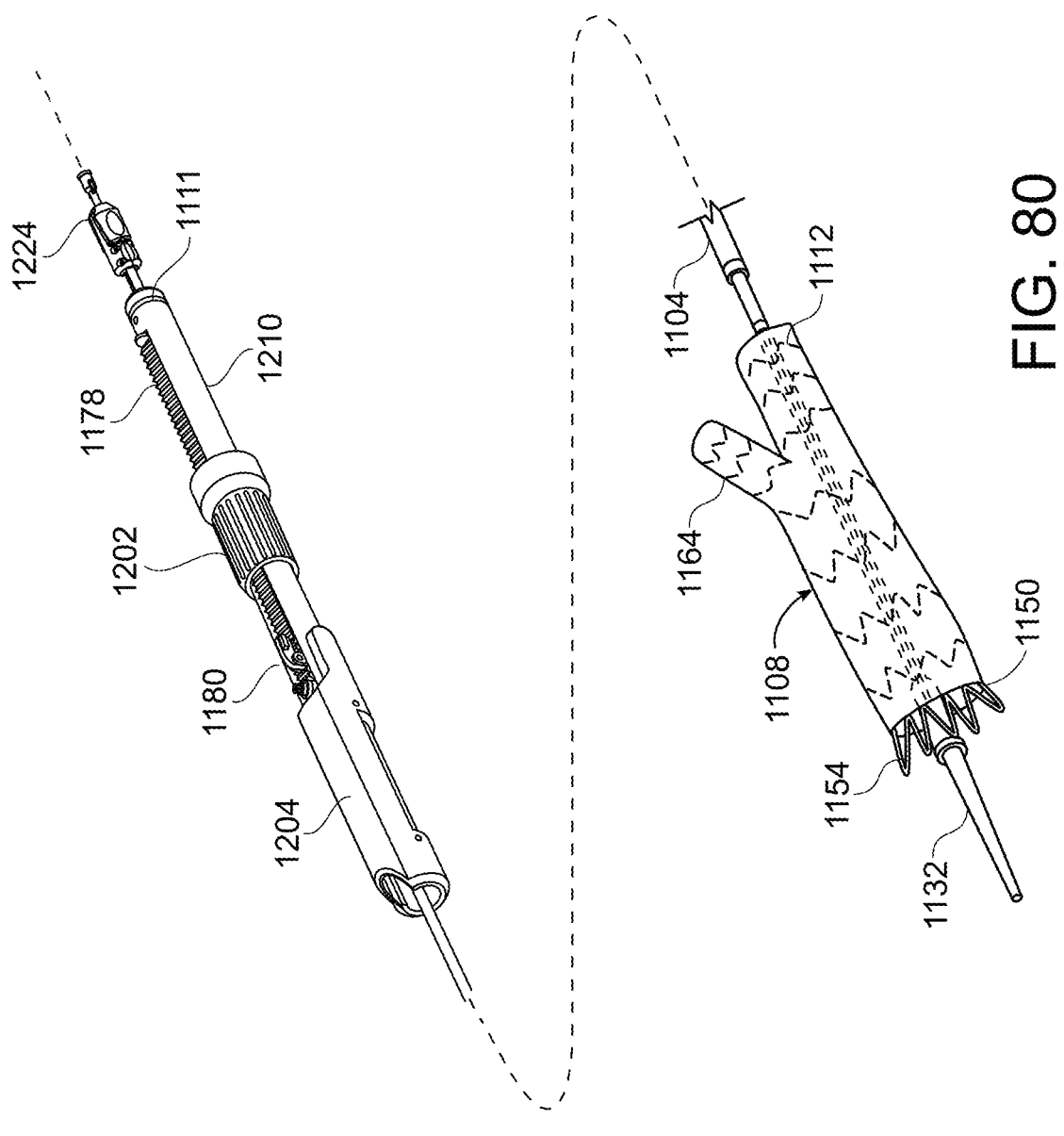

FIG. 80 is a perspective view of the delivery device of the invention shown in FIGS. 73, 74, and 78, following release of the leg of the bifurcated stent graft by the method of the invention.

Figures 81A, 81B, 81C:
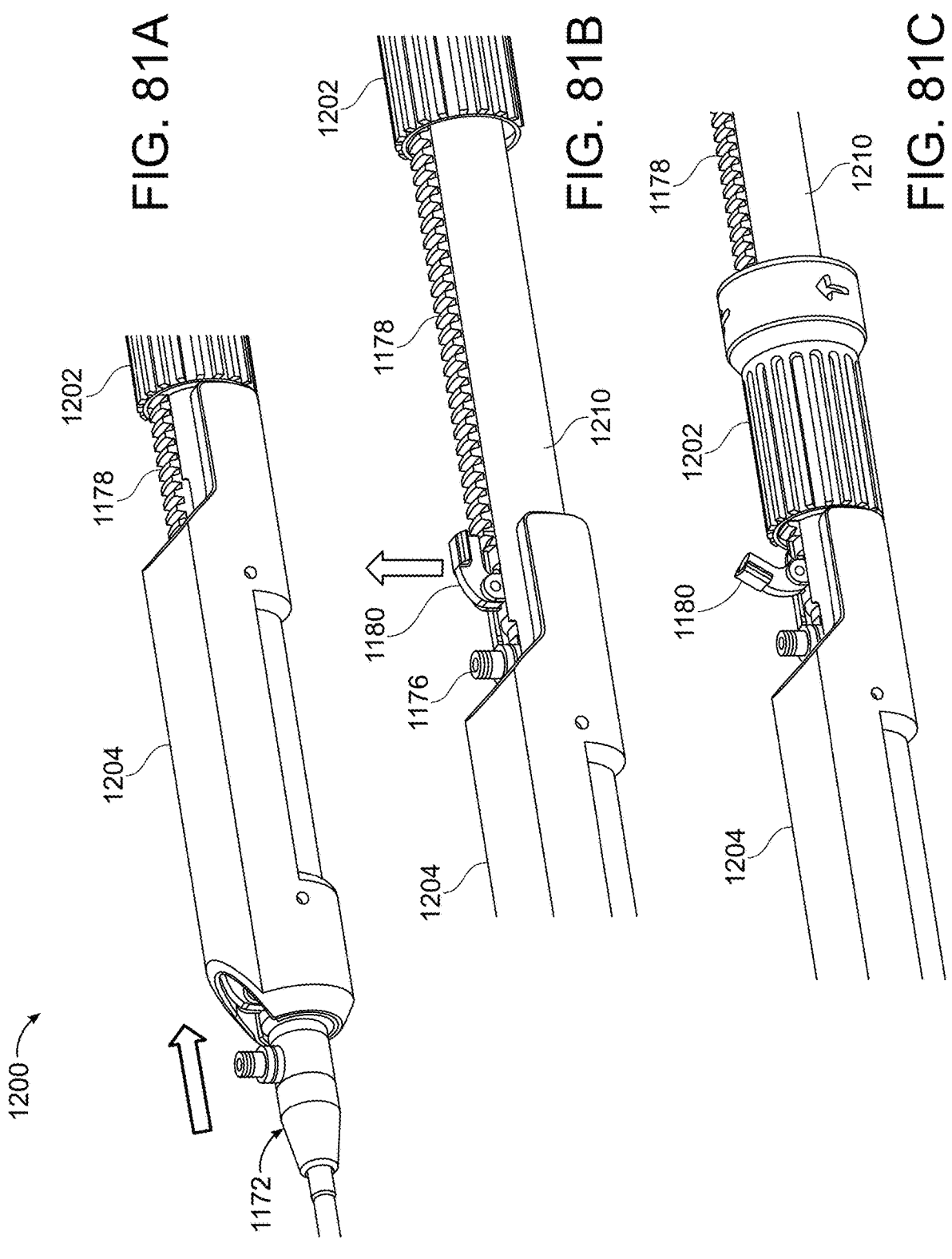

FIG. 81A is a detail of the delivery device prior to retraction of the introducer sheath of the delivery device from the stent graft.

FIG. 81B is a detail of the delivery device following retraction of the introducer sheath from the stent graft and release of the stent graft from the delivery device, but before actuation of a release lever to thereby enable separation of the slider from the remainder of the delivery device, whereby the slider can be left after the remainder of the delivery device is removed from the subject, and whereby the slider can be employed for additional procedural steps, such as attachment of extensions to a leg of a bifurcated stent graft previously implanted, or implantation of at least one branch to the implanted stent graft.

FIG. 81C is a detail of the representation in FIGS. 81A and 81B, following actuation of the release lever.

Figures 82A, 82B:
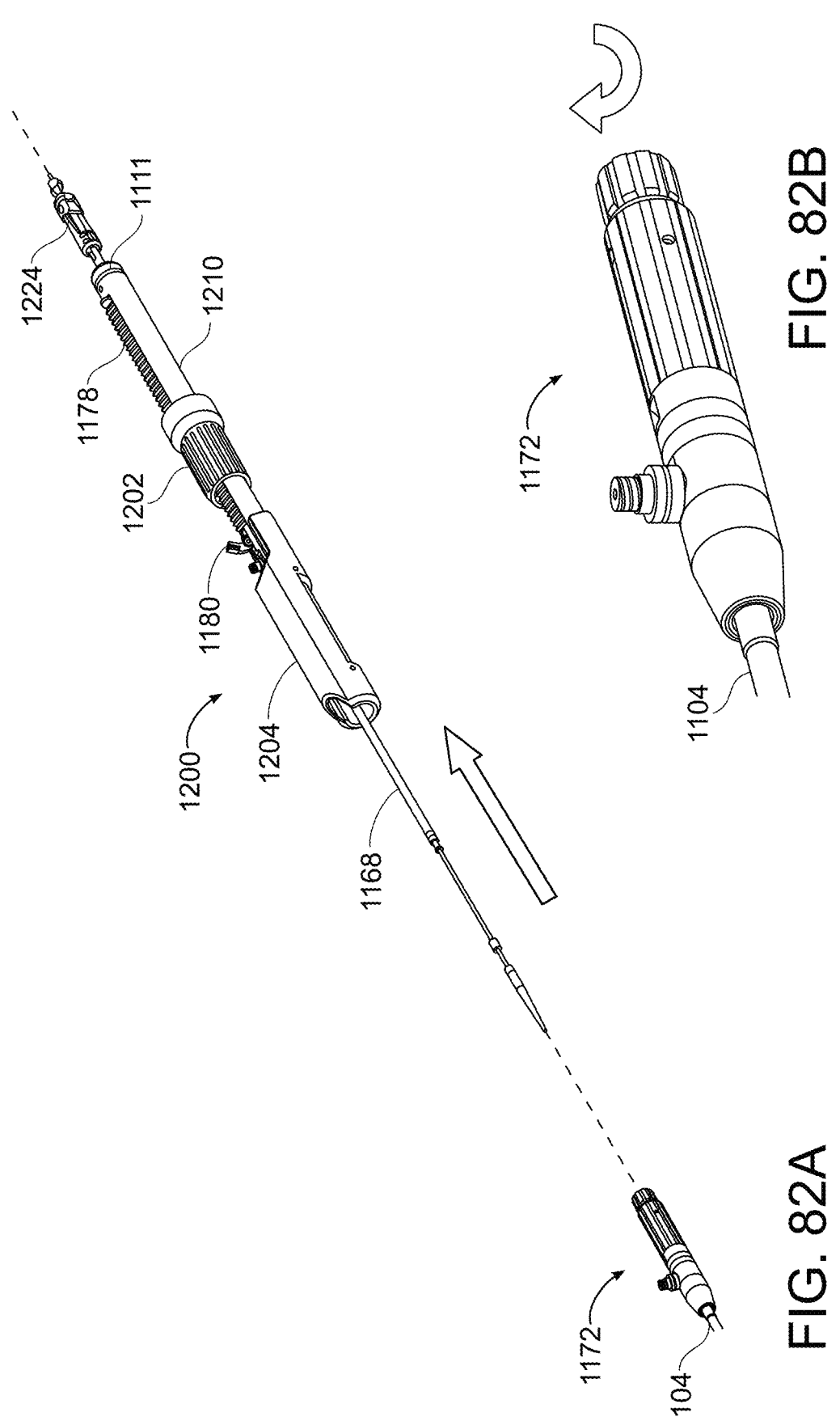

FIG. 82A is a perspective view of the delivery device of FIGS. 73, 74, and 78 following separation of the slider from the remainder of the delivery device.

FIG. 82B is a detail of FIG. 82A, showing just the slider of the delivery device of FIG. 82A.

Figure 83:
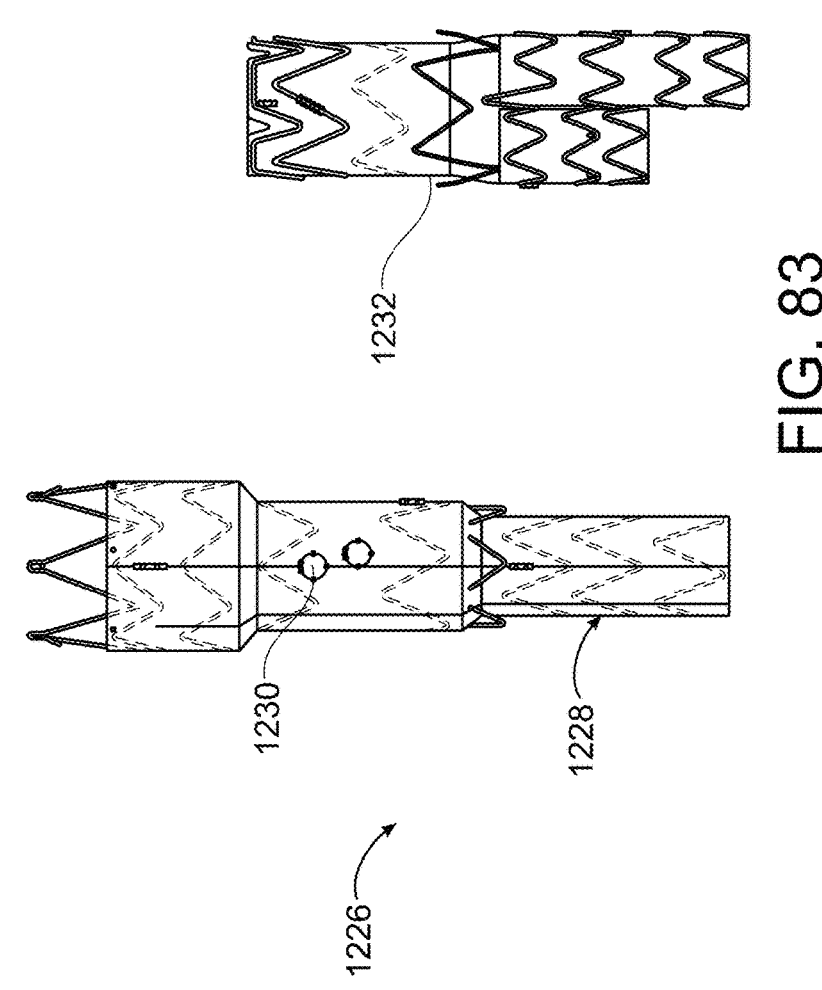

FIG. 83 is an exploded view of one embodiment of a fenestrated stent graft suitable for implantation by the delivery device of the invention.

Figure 84:
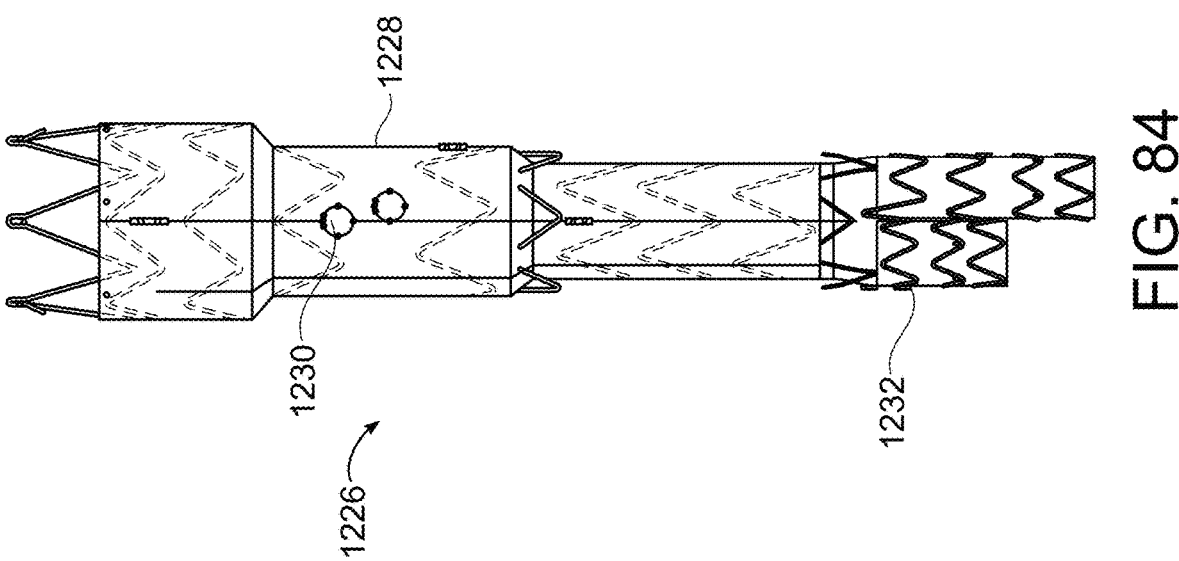

FIG. 84 is a side view of the representation of the fenestrated stent graft shown in FIG. 83.

DETAILED DESCRIPTION OF THE INVENTION

A description of example embodiments follows.

The invention generally is directed to an aortic prosthesis, such as a stent graft, and a delivery system that includes an aortic prosthesis, such as a stent graft, a ligature, and a plurality of wires extending through the lumen of the stent graft and on each lateral side of a fenestration in the stent graft. The invention also is directed to a method of use of the stent graft and delivery system of the invention. The stent graft delivery system and method of its use treat aortic vascular damage, such as vascular damage associated with an aortic aneurysm, including in regions of the aorta having arterial branches that supply blood to vital organs and tissues, such as thoracic aortic aneurysms, abdominal aortic aneurysms, thoracoabdominal aortic aneurysms, including juxtarenal aortic aneurysms and short-neck abdominal aortic aneurysms.

When reference is made herein to an aortic prosthesis, such as a "stent graft" or "vascular prosthesis" or other prostheses to be delivered or implanted in a patient, the word "proximal" means that portion of the prosthesis or component of the prosthesis that is relatively close to the heart of the patient and "distal" means that portion of the prosthesis or component of the prosthesis that is relatively far from the heart of the patient.

When, however, reference is made to a delivery system or a component of a delivery system employed to deliver, or implant, a prosthesis, the word, "proximal," as employed herein, means closer to the clinician using the delivery system. When reference is made to a delivery system or a component of a delivery system, "distal," as that term is employed herein, means further away from the clinician using the delivery system.

For clarity, the word "proximate" means "close to," as opposed to the meanings ascribed to "proximal" or "distal" described above with respect to either the prosthesis or a delivery system.

One embodiment of a stent graft delivery system of the invention is shown in FIG. 1A through 1F. As shown therein, stent graft delivery system 10 includes stent graft 12 of the invention. Stent graft 12 includes luminal graft component 14 having proximal open end 16, distal open end 18, and outside surface 20. Inside surface 22 defines lumen 24 about longitudinal axis 26. Luminal graft component 14 is fabricated of a suitable material, such as is known in the art. Examples of suitable materials include expanded polytetrafluoroethylene (ePTFE) and polyethylene terephthalate (PET), such as woven polyester.

Stents 28 of stent graft 12 are distributed radially about luminal graft component 14 and longitudinally along luminal graft component 14. Stents 28 include struts 30 that are joined at either end to define proximal apices 32 and distal apices 34. Stents 28 are fabricated of a suitable material, such as is known in the art. In one embodiment, stents 28 are fabricated of a material that causes stents 28 to radially self-expand upon release from radial constraint. Examples of suitable materials of radial self-expanding stents include a shape memory alloy, such as Nitinol. Examples of stents not formed of a shape memory alloy include those formed of stainless steel. In embodiments of the invention that do not employ a shape memory alloy, or are otherwise not radially self-expanding, a balloon catheter, for example, can be employed to radially expand stents that have been released from radial constriction, as is known in the art. Stents 28 can also include a radiopaque component, as is known in the art, such as at least one radiopacifier selected from the group consisting of barium sulfate, bismuth, tungsten, platinum-iridium and tantalum-tungsten.

Figures 1A, 1B, 1C, 1D, 1E, 1F:
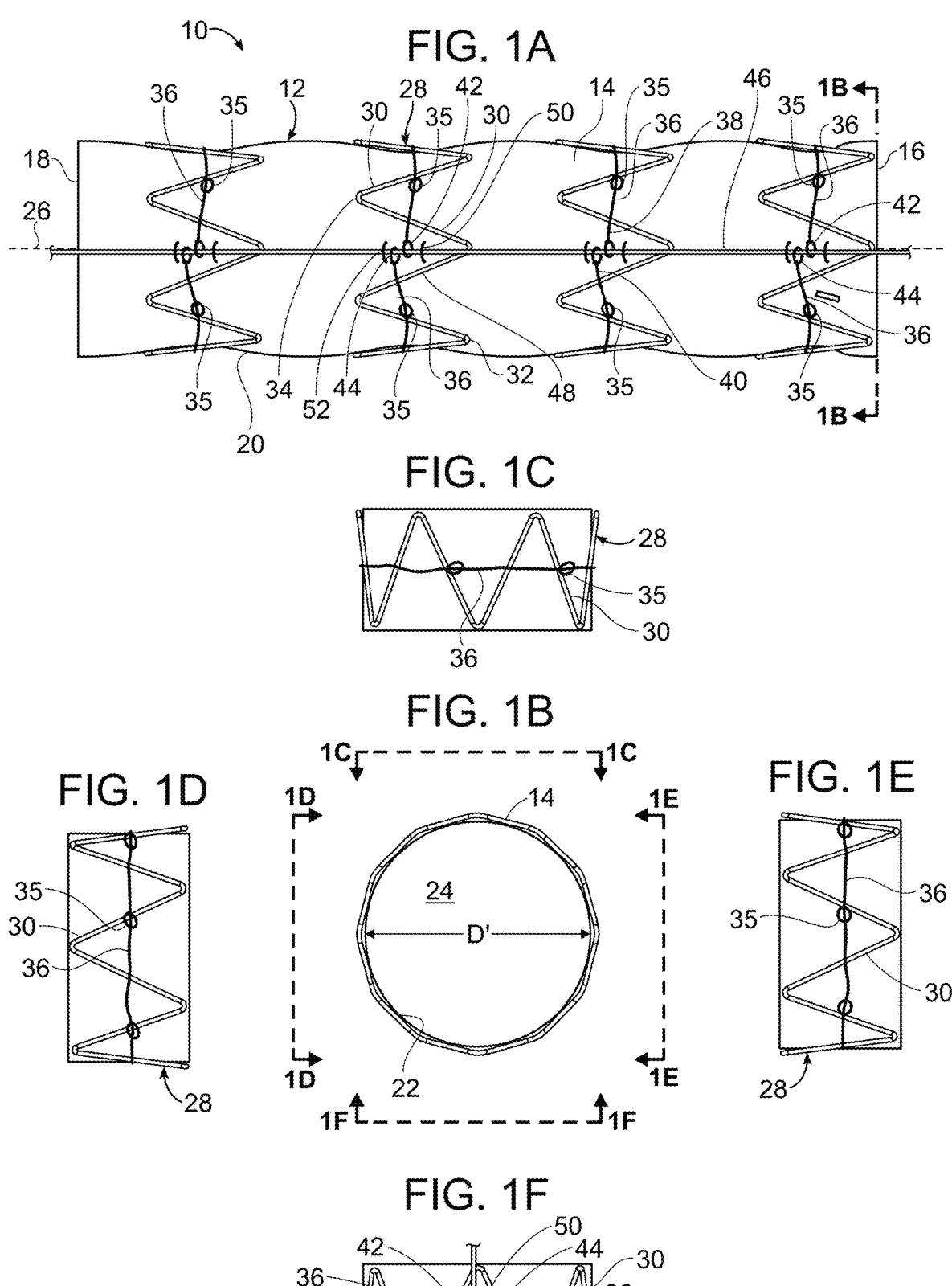
FIG. 1A is a side view of one embodiment of an aortic prosthesis delivery system of the invention, wherein a stent graft is held in a radially constricted position by a ligature that extends through loops that are secured to struts of a stent of the aortic prosthesis delivery system, and a wire maintaining the stent graft in a radially constricted position is stabilized by anchor loops.
FIG. 1B is an end view of the aortic prosthesis delivery system of FIG. 1A, taken along line 1B-1B, and having diameter D'.
FIG. 1C is a side view of the proximal end of the stent graft of FIG. 1B taken along line 1C-1C.
FIG. 1D is a side view of the proximal end of the stent graft of FIG. 1B taken along line 1D-1D.
FIG. 1E is a side view of the proximal end of the stent graft of FIG. 1B taken along line 1E-1E.
FIG. 1F is a side view of the proximal end of the stent graft of FIG. 1B taken along line 1F-1F.

Loops 35 are fixed to struts 30 by suitable means, such as thread or suture material, such as polyester or nylon. Ligatures 36, such as single-stranded ligatures as opposed to, for example collapsed hoops, described infra, extend about luminal graft component 14 and include ends 38,40. Ligatures 36 are formed of a suitable material, such as is known in the art. Examples of suitable materials of ligatures 36 include polyester and nylon, or a shape-memory alloy, such as Nitinol. As shown in FIG. 1A, ends of ligatures 36 include ligature loops 42,44. Ligature loops 42,44 are linked, such as by wire 46, as shown in FIG. 1A, to constrict the diameter of stent graft 12. Ligatures 36 extend through loops 35 and traverse struts 30 of stents 28. On either immediate lateral side of wire 46, ligatures 36 traverse struts 30 by passing over a radially outwardly-facing portion 48 of struts 30.

Likewise, anchor loops 50,52 are formed of a suitable material, such as a material suitable for fabrication of ligatures 36. Anchor loops 50,52 are distributed longitudinally on wire 46 on either side of the portion of ligature loops 42,44 of ligatures 36 and, consequently, span ligature loops 42,44 to stabilize wire 46, at least in part, from lateral migration of wire 46 about the periphery of stent graft 12, and to keep ends 38,40 of ligatures 36 in close proximity to stent graft 12. It is to be understood that, in certain other embodiments, anchor loops 50,52 are not present, such as in embodiments where ligatures 36 are stabilized at stent graft 12 by, for example, being threaded between luminal graft component 14 and struts 30, thereby substantially preventing lateral migration of wire 46 when wire 46 is linking ends 38,40 of ligatures 36.

Returning to FIG. 1A, wire 46 extends through loops 42,44 of ligatures 36, thereby linking ends 38,40 of ligatures 36 and maintaining stent graft 12 in a radially constricted position. It is to be understood that, when stents 28 are formed of a shape-memory metal alloy, such as Nitinol, then ligatures 36 hold stents 28 in a radially-constricted position, wherein radially self-expanding stents 28 exert a radially outward force against ligatures 36. It is also to be understood that, in alternative embodiments, ligatures 36 can traverse struts 30 between struts 30 and luminal graft component 14, or about radially outwardly-facing portion 48 of struts 30, in different arrangements than that shown in FIG. 1A. Further, it is to be understood that ligatures 36 can pass through the fabric of luminal graft component 14 into lumen 24 in various embodiments, such as in an embodiment wherein wire 46 extends through lumen 24 and against the inside surface of luminal graft component 14, as opposed to outside surface 20 of luminal graft component 14. Also, alternatively, in certain embodiments (not shown), stents 28 can be secured to luminal graft component 14 at inside surface 22 of luminal graft component 14, in which case wire 46 would, in one possible embodiment, extend within lumen 24, and ligatures 36 would traverse struts 30 between struts 30 and the inside surface of luminal graft component 14. Other arrangements between wire 46, ligatures 36 and stents 28 are also possible.

FIG. 1B is an end view of stent graft 12, shown in FIG. 1A, taken along line 1B-1B. As can be seen in FIG. 1B, constricted open stent graft 12 has an inside diameter of D'. FIG. 1C is a side view of the stent and luminal graft component at proximal open end 16 of stent graft 12 shown in FIG. 1A, as viewed from line 1C-1C of FIG. 1B. Likewise, FIGS. 1D, 1E, and 1F, show side views of the most proximal stent of stent graft 12, shown in the end view of FIG. 1B, taken along lines 1D-1D, 1E-1E and 1F-1F, respectively. Collectively, FIGS. 1A-1F show ligature 36 extending about the perimeter of stent graft 12, where ligatures 36 pass over an outwardly-facing portion 48 of struts 30.

FIG. 2A is a side view of stent graft 12 shown in FIG. 1A, but following retraction of wire 46 from anchor loops 50,52 and loops 42,44 of ligatures 36, thereby allowing radial expansion of stents 28 from the constricted position, shown in FIGS. 1A-1F, to an expanded position, shown in FIG. 2A. Radial expansion of stents 28, such as by expansion of radially self-expanding stents 28 fabricated of, for example, Nitinol, causes ends 38,40 and, specifically, loops 42,44 of ligatures 36 to separate from each other and from anchor loops 50,52 longitudinally spanning wire loops 42,44 where wire 46 had previously linked loops 42,44 between anchor loops 50,52. FIG. 2B is an end view of stent graft 12 of FIG. 2A, taken along line 2B-2B, showing an expanded internal diameter D" following release of stent graft 12 from the radially constricted position represented in FIGS. 1A-1F. FIGS. 2C, 2D, 2E and 2F show side views of the most proximal stent and the luminal graft component at proximal open end 16 represented in FIG. 2B, taken along lines 2C-2C, 2D-2D, 2E-2E, and 2F-2F respectively.

FIG. 3A is a side view of another embodiment of the stent graft delivery system of the invention. As shown therein, stent graft delivery system 60 additionally supports ligatures 36 by ligature sutures 62,64 at stent graft 12 between each loop 42,44 and struts 30 they traverse on either side of wire

46. The arrangement of ligature sutures 62,64 between loops 42,44 and respective struts 30 traversed by ligatures 36 stabilizes linkage of loops 42,44 by wire 46. It is to be understood that, in still another embodiment, ligature sutures 62,64 can be employed in the alternative to anchor loops 50,52 to thereby stabilize loops 42,44 when linked by wire 46. FIG. 3B is an end view of proximal open end 16 of stent graft 12 shown in FIG. 3A, taken along line 3B-3B, and showing inside diameter D' of most radially constricted stent graft 12. FIGS. 3C, 3D, 3E and 3F, show side views of the most proximal stent 28 and luminal graft component at proximal open end 16 shown in cross-section in FIG. 3B, taken along lines 3C-3C, 3D-3D, 3E-3E, and 3F-3F, respectively.

FIG. 4A is a side view of stent graft delivery system 60 shown in FIG. 3A, following retraction and withdrawal of wire 46 (not shown) from anchor loops 50,52 and linkage of loops 42,44. As can be seen therein, radial expansion of stents 28 from a radially constricted position to a radially-expanded position causes loops 42,44 to laterally separate from each other and, as shown in FIG. 4A, to retract from the ligature sutures 62,64, respectively. FIG. 4B is an end view of the stent graft in a radially expanded position, as shown in FIG. 4A, taken along line 4B-4B, showing the expanded inside diameter D" following radial expansion of stent 28 at that section. FIGS. 4C, 4D, 4E, and 4F, show side views of the most proximal stent 28 and luminal graft component 14 at the most proximal stent 28 shown in cross-section in FIG. 4B, taken along lines 4C-4C, 4D-4D, 4E-4E, and 4F-4F, respectively.

FIG. 5A is a side view of yet another embodiment of a stent graft delivery system of the invention. As shown in FIG. 5A, stent graft delivery system 70 includes ligatures 72 at each stent 74 of stent graft 94. Stent graft 94 includes stents 74 and luminal graft component 96. Luminal graft component defines lumen 98. Ligatures 72 include two component parts 76,78, each of which is secured at separate struts 80,82 of respective stent 74. Ligatures 72 include loops 84,86 at each end that are aligned by wire 92, which passes through them, thereby maintaining stent graft 94 in a constricted position. Ligature parts 76,78 are stabilized by anchor loops 100,102 longitudinally spanning loops 84,86 when wire 92 is threaded through loops 84,86, thereby radially constricting stents 74. Although not shown, it is to be understood, that ligature sutures can, optionally, also be employed, as described with respect to FIGS. 1A and 3A. FIG. 5B is an end view of the stent graft delivery system 70 shown in FIG. 5A, taken along line 5B-5B, showing an internal diameter D' of stent graft 94 in a radially constricted position. FIGS. 5C, 5D, 5E, 5F, show side views of the most proximal stent 74 and the portion of the luminal graft component at the most proximal stent 74, shown in FIG. 5B taken along lines 5C-5C, 5D-5D, 5E-5E and 5F-5F, respectively.

FIG. 6A is a side view of stent graft 94 shown in FIG. 5A, following retraction of wire 92 (not shown) from anchor loops 100,102 and loops 84,86 of ligatures 72, thereby allowing stent graft 94 to radially expand from the radially constricted position, shown in FIGS. 5A-5F, to a radially expanded position, shown in FIG. 6A. As can be seen in FIG. 6A, loops 84,86 laterally separate from each other, and from anchor loops 100,102 upon radial expansion of stent graft 94 from the radially constricted state to the expanded state. FIG. 6B is an end view of stent graft 94 shown in FIG. 6B, taken along line 6B-6B, showing a radially expanded internal diameter D" of stent graft 94. FIGS. 6C, 6D, 6E, and 6F, show side views of the most proximal stent 74 and the portion of luminal graft component 96 most proximate to the most proximal stent 74, shown in FIG. 6B, taken along lines 6C-6C, 6D-6D, 6E-6E, and 6F-6F, respectively.

In another embodiment, the ligatures are in the form of collapsed hoops 104 that extend about the periphery of stent graft 12 to form distally opposed ends 106, 107 of collapsed hoops 104 that are linked by wire 46. Wire 46 is stabilized by anchor loops 108 at the stent graft as shown in FIGS. 7A, 7F.

Figures 8A, 8B:
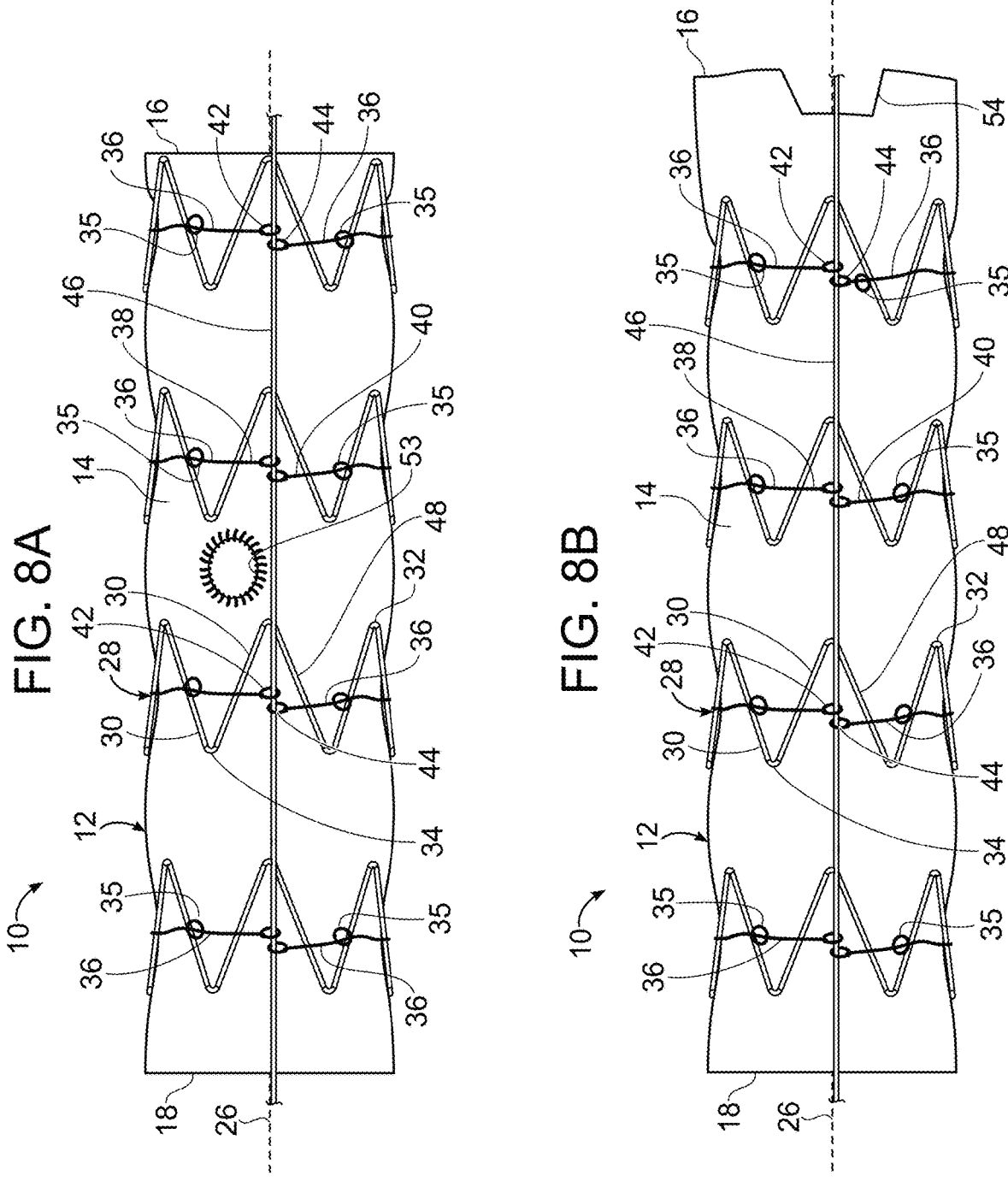
FIG. 8A is a side view of another embodiment of an aortic prosthesis delivery system of the invention, wherein a stent graft includes a fenestration and a ligature extends through loops fixed to struts of stents of the stent graft.
FIG. 8B is a side view of yet another embodiment of an aortic prosthesis delivery system of the invention, wherein the proximal open end includes a scalloped edge and a ligature extends through loops fixed to struts of stents of the stent graft.
Figures 8C, 8D:
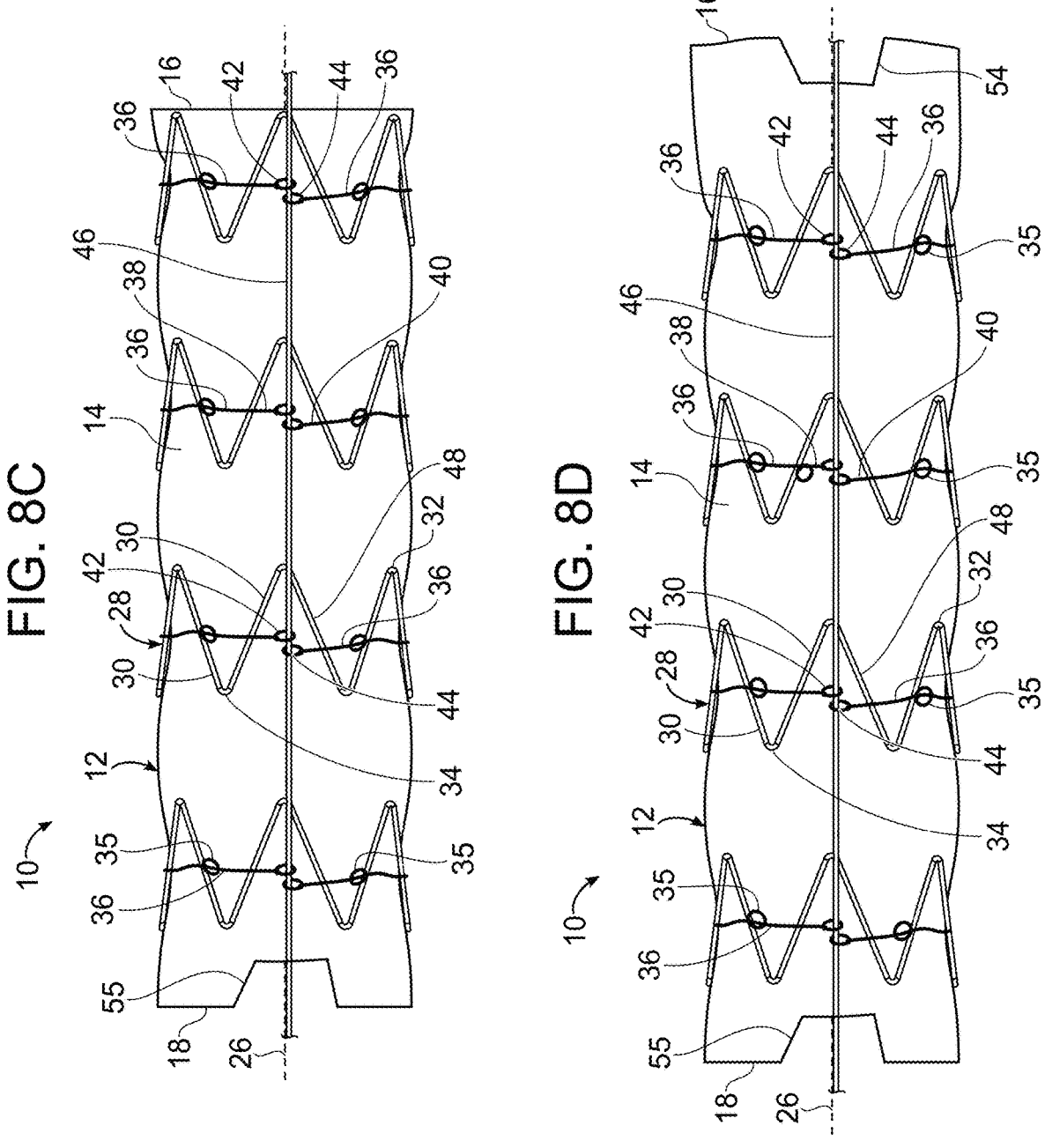
FIG. 8C is a side view of a further embodiment of an aortic prosthesis delivery system of the invention, wherein the distal open end includes a scalloped edge and a ligature extends through loops fixed to struts of stents of the stent graft.
FIG. 8D is a side view of a further embodiment of an aortic prosthesis delivery system of the invention, wherein both the proximal and distal open ends include a scalloped edge and a ligature extends through loops fixed to struts of stents of the stent graft.

As shown in FIGS. 8A through 8D, stent graft 10 of FIGS. 1A through 1F can include at least one proximal fenestration 53 (FIG. 8A) and, optionally, a scalloped proximal open end 54 (FIG. 8B), a scalloped distal open end 55 (FIG. 8C) and scalloped proximal and distal open ends 54,55, respectively (FIG. 8D). Although not shown, stent graft 10 can include at least one fenestration in combination with at least one of a scalloped proximal open end and a scalloped distal open end. In additional embodiments, the stent grafts of the invention can include a bare stent at at least one of the proximal open end and distal open end that, optionally, can include barbs at respective proximal or distal apices (not shown).

Figures 9, 10A, 10B, 10C, 10D, 10E:
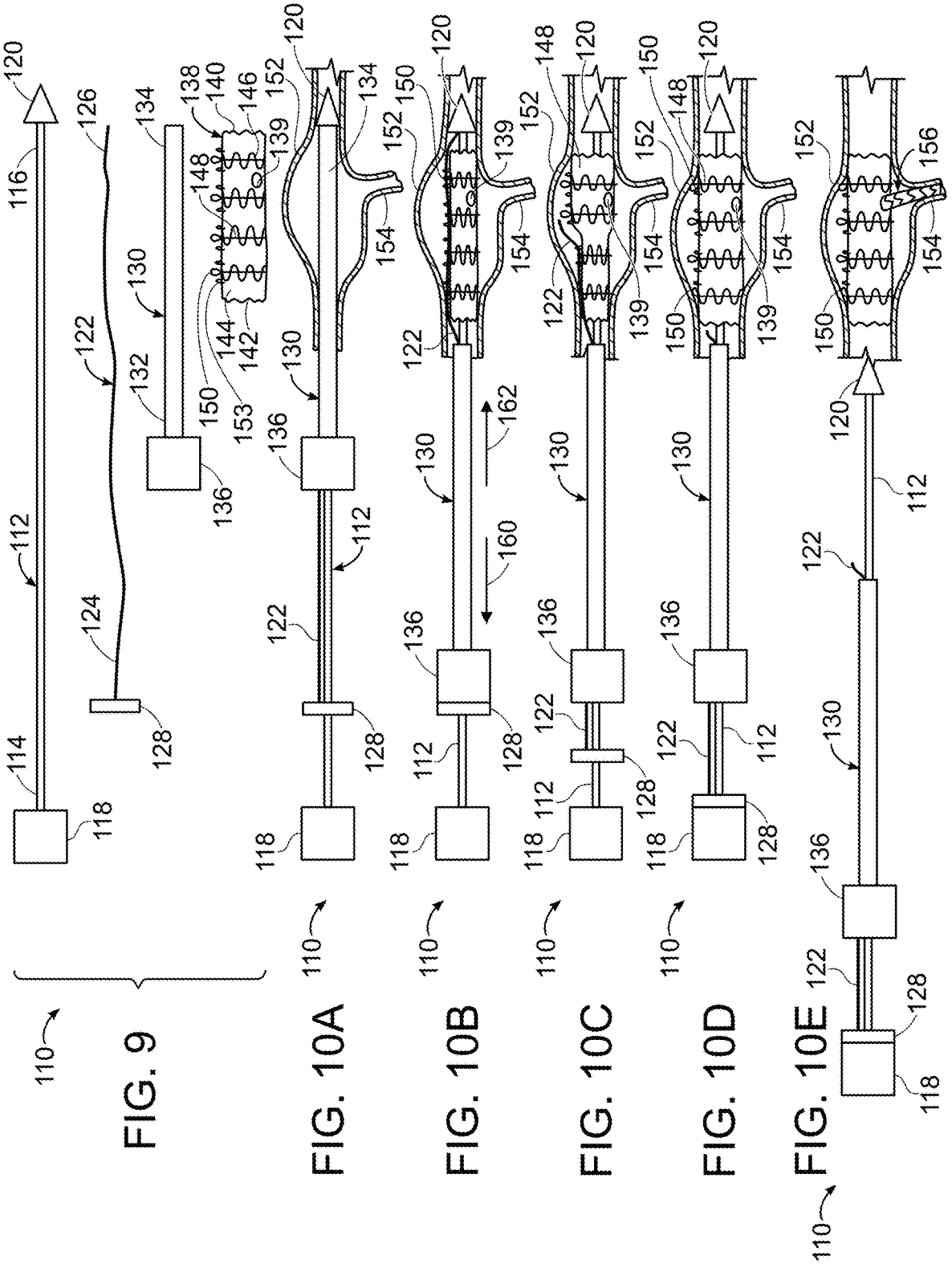
FIG. 9 is an exploded side view of one embodiment of an aortic prosthesis delivery system of the invention.
FIG. 10A is a side view of the aortic prosthesis delivery system shown in FIG. 9, but in assembled form and, wherein the introducer sheath, containing a stent graft of the aortic prosthesis delivery system of the invention, has been delivered to an arterial aneurysm of a patient.
FIG. 10B is a side view of the aortic prosthesis delivery system of FIG. 10A, following proximal retraction of the introducer sheath along the stent graft delivery device, to thereby expose the stent graft, which is held in a radially constricted position by a wire of the stent graft delivery system.
FIG. 10C is a side view of the aortic prosthesis delivery system shown in FIGS. 10A and 10B, following partial retraction of the wire from ligatures that, when linked by the wire, holds the stent graft in a partially radially constricted position, while the remainder of the stent graft is in a radially expanded position.
FIG. 10D is a side view of the aortic prosthesis delivery system shown in FIGS. 10A-10C, following full retraction of the wire from the stent graft, whereby the stent graft is in a radially expanded position along its entire length.
FIG. 10E is a side view of the aortic prosthesis delivery system shown in FIGS. 10A through 10D, following retraction of the remainder of the stent graft delivery system not implanted at the aneurysm, and following separate implantation of a branch stent graft through a fenestration of the stent graft and into a branch blood vessel, whereby implantation of the stent graft and the branch stent graft at the aneurysm of the patient is complete.

FIG. 9 is an exploded side view of another embodiment of the stent graft delivery system of the invention. As shown therein, stent graft delivery system 110 includes guidewire catheter 112 having proximal end 114 and distal end 116. Proximal handle 118 is fixed to proximal end 114 of guidewire catheter 112. Nose cone 120 is fixed to distal end 116 of guidewire catheter 112. Wire 122 includes proximal end 124 and distal end 126. Wire 122 can be fabricated of a suitable material, such as is known in the art, including, for example, Nitinol or some other shape-memory alloy. Wire 122 is sufficiently flexible not to injure the patient during advancement to an aortic aneurysm of a patient. Wire handle 128 is fixed at proximal end 124 of wire 122. Introducer sheath 130 includes proximal end 132 and distal end 134, and distal handle 136 is fixed to proximal end 132 of introducer sheath 130. Stent graft 138 includes proximal end 140, distal end 142, luminal graft component 144, stents 146 distributed along luminal graft component 144, and ligatures 148, arranged and configured as discussed above.

FIG. 10A is an assembled side view of stent graft delivery system 110 shown in FIG. 9, wherein stent graft 138 has been loaded within distal end 134 of introducer sheath 130, and radially constricted, at least in part, by wire 122 threaded through loops 150 at ends of ligatures 148, as discussed above. In an embodiment, stent graft 138 includes fenestration 139. In a method of the invention, stent graft delivery system 110 is advanced to arterial aneurysm 152 of a patient. In one embodiment, shown in FIG. 10A, introducer sheath 130 is advanced to aneurysm site 152 to thereby place stent graft 138 at arterial aneurysm 152. As can be seen in FIG. 10B, distal handle 136 is retracted in a proximal direction indicated by arrow 160 toward proximal handle 118, thereby retracting introducer sheath 130 from stent graft 138 at aneurysm 152. As can be seen in FIG. 10B, despite retraction of introducer sheath 130, stent graft 138 is maintained in a radially constricted position by wire 122 extending through ligature loops 150 of ligatures 148 traversing struts of stents 146 distributed longitudinally along stent graft 138. It is to be understood, however, that in alternative embodiments, stent graft delivery system 110 can be advanced within an artery to a position distal to arterial aneurysm 152, wherein stent graft 138 is directed to arterial aneurysm 152 by advancement of proximal handle 118 and wire handle 128 in a distal direction indicated by arrow 162 toward distal handle 136 to thereby direct radially constricted stent graft 118 from introducer sheath 130 to arterial aneurysm 152.

Following direction of stent graft to a position that spans aneurysm 152, and at least partial rotational and axial alignment of stent graft at aneurysm 152, wire 122 is partially retracted from loops 150 of ligatures. Proximal retraction of wire handle 128 toward proximal handle 118, in the direction indicated by arrow 160, as can be seen in FIG. 10C. Continued retraction of wire 122 withdraws wire 122 from all of suture loops 150 of ligatures 148, thereby enabling stent graft 138 to fully expand from its radially constricted state, shown in FIG. 10B, to a radially expanded state, shown in FIG. 10D. In an embodiment, stent graft 138 is positioned so that fenestration 139 is properly aligned with arterial branch 154 for subsequent placement of branch prosthesis 156 through fenestration 139 to arterial branch 154. Thereafter, stent graft 138 is fully implanted within aneurysm, and the remainder of stent graft delivery device 110 is retracted from stent graft 138 and the patient, as shown in FIG. 10E, thereby completing treatment of aneurysm site 152 of the patient by the method of the invention.

Figure 11:
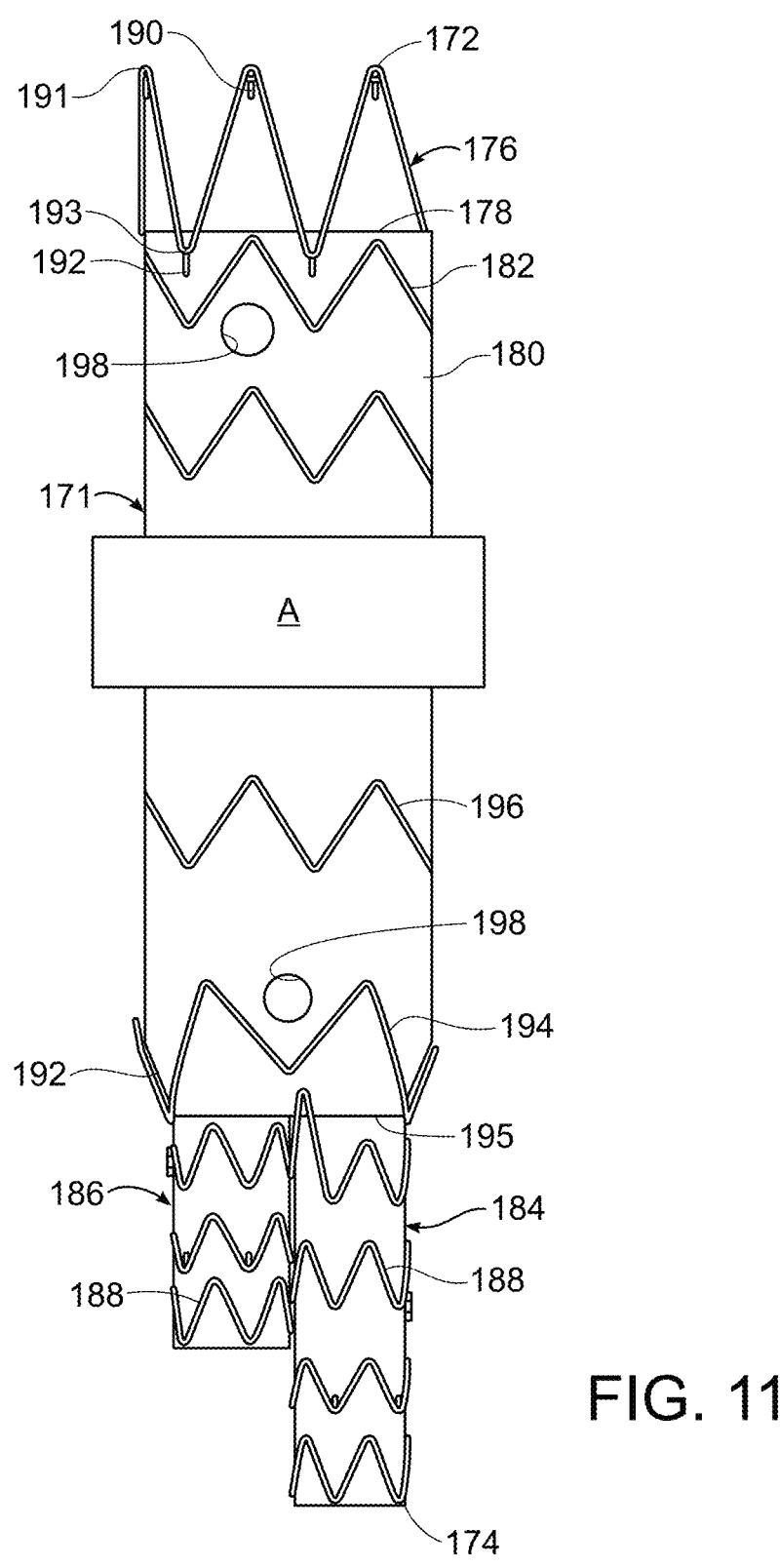
FIG. 11 is a side view of one embodiment of an aortic prosthesis of the invention, wherein a box symbolizes specific embodiments of the invention set forth in FIGS. 12 through 24.

FIG. 11 is a side view of one embodiment 170 of an aortic prosthetic delivery system of the invention. As can be seen in FIG. 11, bifurcated stent graft 171 includes open proximal end 172 and open distal end 174. It is to be understood, however, that the stent graft need not be bifurcated, but, rather, for example, a single luminal conduit. Bare stent 176 extends proximally from proximal end 178 of tubular graft component 180 of bifurcated stent graft 171, and is nested with proximal stent 182. Leg 184 and leg 186 extend distally from tubular graft component 180. Stents 188 support both leg 184 and leg 186. Tubular graft component 180 tapers at distal end 195 of tubular graft component 180 in transition to leg 184 and leg 186. Transition segment 192 of tubular graft component 180 is supported by transitional stent 194. All of bare stent 176, proximal stent 182, transitional stent 194 and stents 188 supporting leg 184 and leg 186 include struts that meet at either end to form proximal and distal apices. Barbs 190,192 extend distally from proximal apices 191 and distal apices 193, respectively, of bare stent 176. Generally, distal apices 193 of bare stent are sewn to an external surface of tubular graft component 180, while proximal stent 182 typically is sewn to an inside surface of tubular graft component 180. Transitional stent 194 is typically sewn to the outside surface, but alternatively, can be on the inside surface of tubular graft component 180. Stents 196 are distributed longitudinally along the length and on the outside surface of tubular graft component 180. Tubular graft component 180 can define fenestrations 198. At least one fenestration 198 can be located anywhere along tubular graft component 180, and can be nested between struts of stents, as shown. Fenestration 198 can define, alternatively, 2, 3, 4, or 5 fenestrations, for example. Box A represents alternative embodiments of stents located between proximal stent 182 and transitional stent 194, as those embodiments are shown in FIGS. 12 through 24 below that, accordingly, constitute embodiments of the aortic prosthetic delivery system of the invention.

Figure 12:
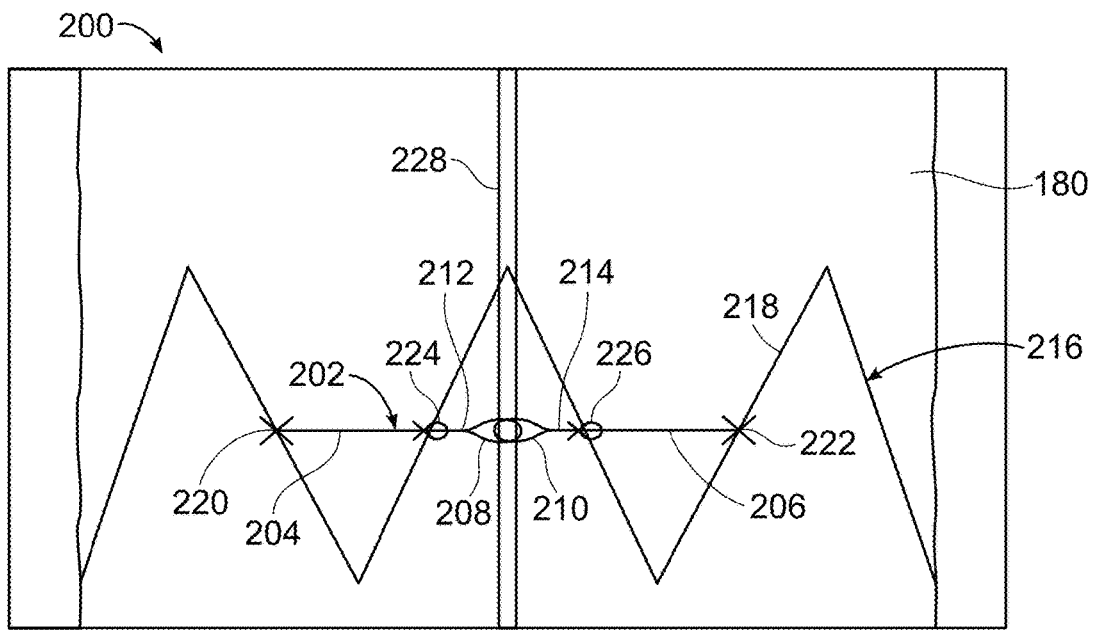
FIG. 12 is a detail of one embodiment of an aortic prosthetic delivery system of the invention wherein the ligature includes two component parts.

FIG. 12 is a detail of one embodiment 200 of an aortic prosthetic delivery system generally represented by "A" of FIG. 11 of the invention wherein ligature 202 includes two component parts 204, 206. Component parts include ligature loops 208, 210 at respective ends 212, 214 and are fixed to stent 216 at struts 218 at opposite respective ends, 220, 222. Ligature component parts 204, 206 extend through loops 224, 226 that are fixed to at least one strut 218 at at least one point between the respective ends 212, 220 and 214, 222 of respective ligature component parts 204, 206. Loops 224, 226 are fixed to struts 218 by suitable means, such as by tying loops 224, 226 to struts 218, such as by use of square knots. When a stent graft, such as that shown in FIG. 1A, of which FIG. 12 is a detail of one embodiment, is constrained by ligature 202, wire 228 extends through ligature loops 208, 210 to link ligature component parts 204, 206 and thereby radially constrain stent 216 and the stent graft.

Figure 13:
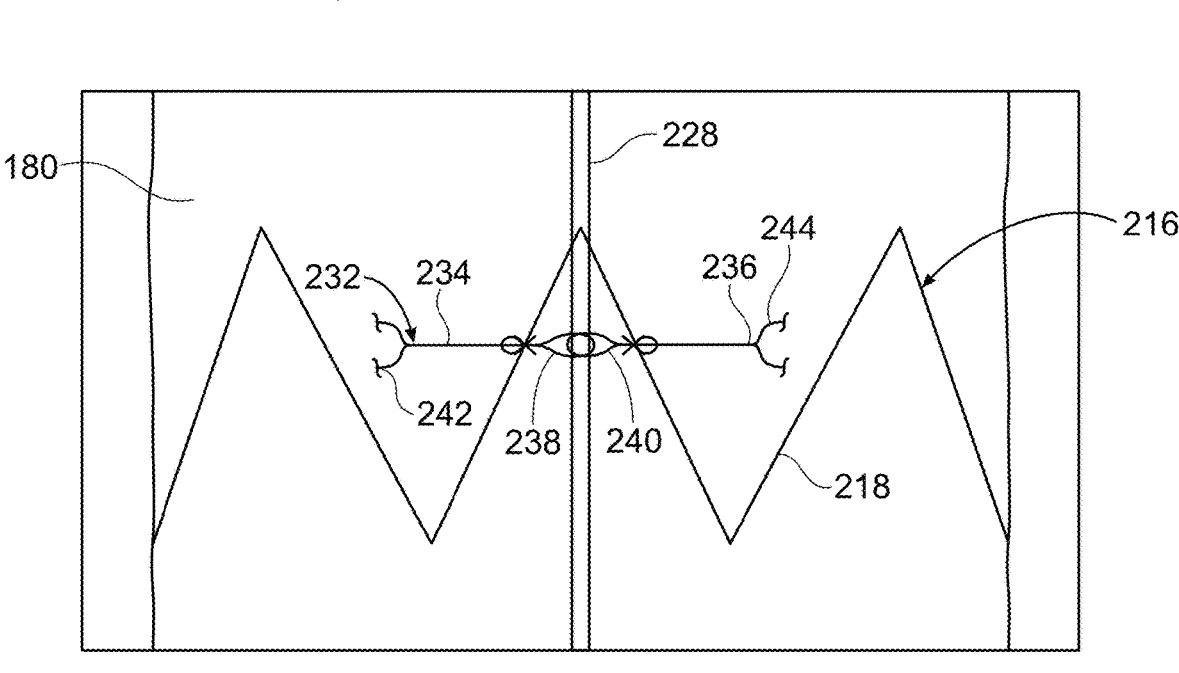
FIG. 13 is a detail of another embodiment of an aortic prosthesis system of the invention wherein ends of respective ligature loops are fixed to struts, second ligature loops extend about struts and through a graft component of the stent graft.

FIG. 13 is a detail of another embodiment 230 of an aortic prosthesis system of the invention. In this embodiment, ligature 232 includes component parts 234, 236 having respective ligature loops 238, 240 linked by wire 228. Second ligature loops 242, 244 extend through and are anchored to graft component 180 of a stent graft.

Figure 14:
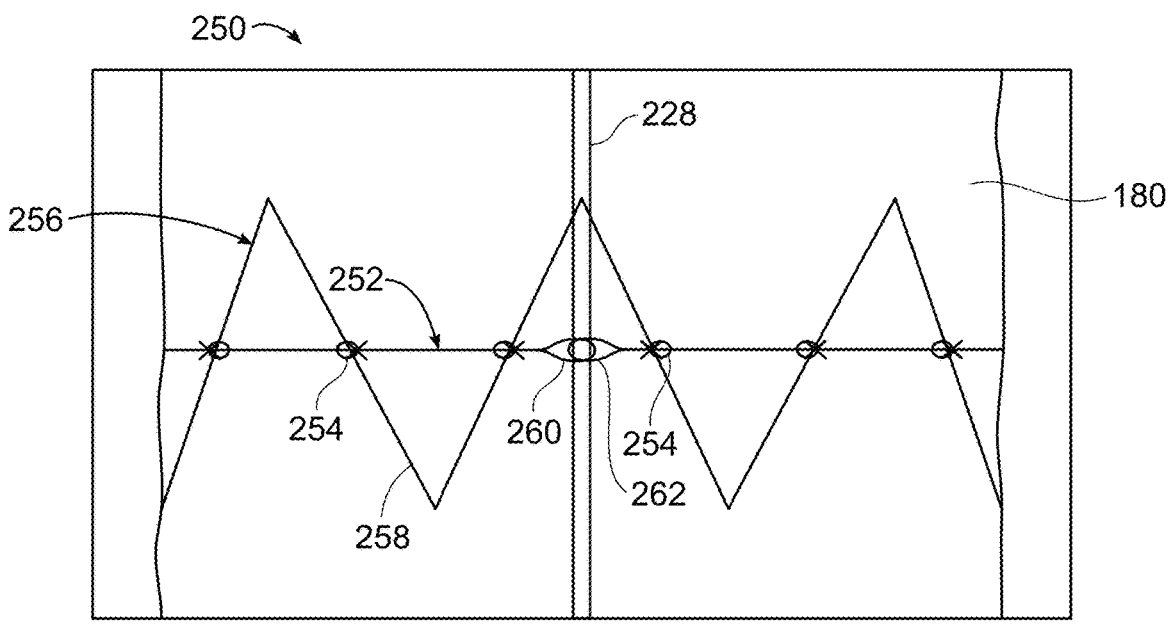
FIG. 14 is a detail of another embodiment of an aortic prosthesis system of the invention wherein loops are fixed to struts and maintain longitudinal position of a ligature along the length of stent graft and along the length of struts, and wherein the ligature extends through the loops and about the stent graft.

FIG. 14 is a detail of another embodiment 250 of an aortic prosthesis system of the invention. In this embodiment 250, ligature 252 extends through loops 254 that are fixed to stent 256 at struts 258 and maintain longitudinal position of ligature along the length of the stent graft of which FIG. 13 is a detail, and along the longitudinal distance of struts 258. Ligature 252 extends through loops 254 and around the stent graft. While, as shown in FIG. 14, loops can be on each strut of stent, in an alternative embodiment, not shown, loops can be on only one strut, for example, or some portion of struts 258 of stent 256, such as every other strut 258. Ligature loops 260, 262 of ligature are linked by wire 228 to thereby radially constrain stent 256 and the stent graft. Removal of wire 228 from ligature loops 260, 262 releases stent 256 and the stent graft from radial constraint.

Figure 15:
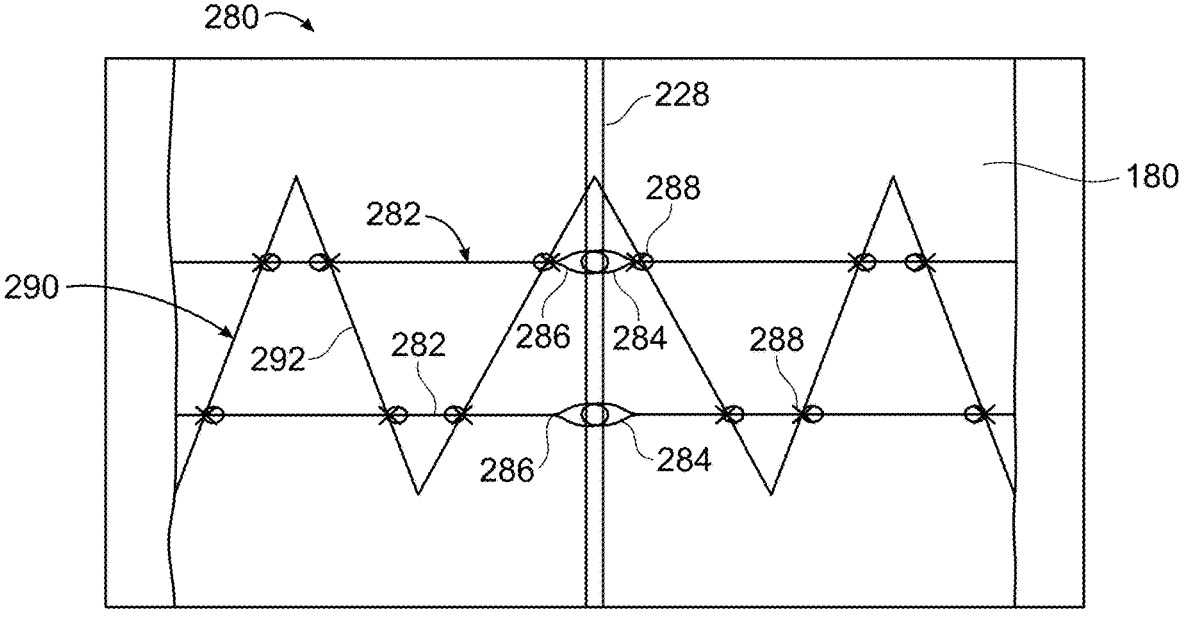
FIG. 15 is a detail of yet another embodiment of another aortic prosthesis system of the invention, wherein a plurality of ligatures circumscribe a stent graft.

FIG. 15 is a detail of yet another embodiment of another aortic prosthesis system of the invention, wherein a plurality of ligatures circumscribe stent graft. In aortic prosthesis system 280, like the embodiment of FIG. 14, ligatures 282 include ligature loops 284, 286 are linked by wire 228, thereby radially constraining the stent graft of aortic prosthesis system 280. Loops 288 are fixed to stent 290 at struts 292 and maintain the longitudinal positions of ligatures 282 along the longitudinal distance of the stent graft and along the length of struts 292. Ligatures 282 extend through loops 288. While, as shown in FIG. 15, loops 288 are on each strut 292 of stent 290, in an alternative embodiment, not shown, loops 288 associated with each ligature 282 can be on only one strut 292, for example, or some portion of struts 292 of stent 290, such as alternate struts 292 of stent 290.

Figure 16:
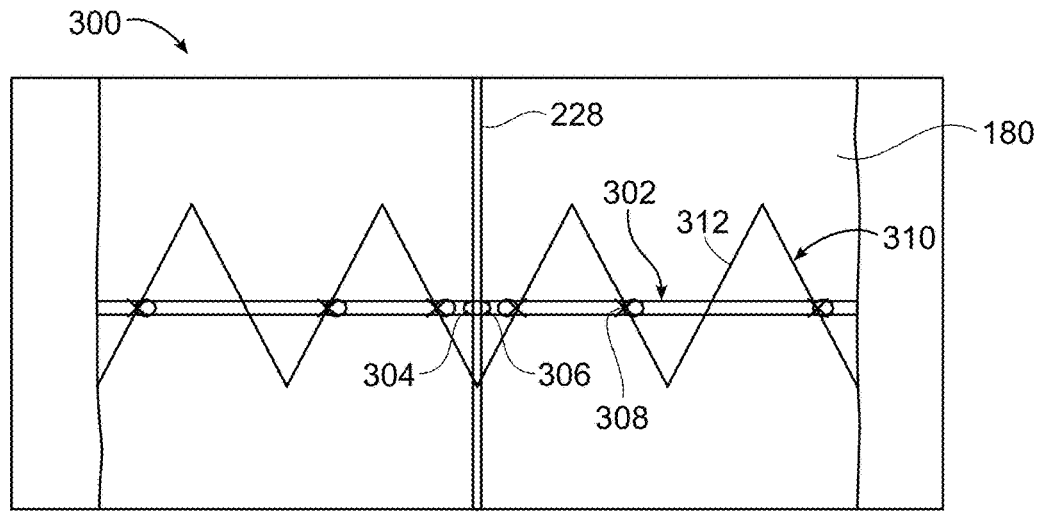
FIG. 16 is a detail of an embodiment of the aortic prosthesis system of the invention wherein the ligature is a collapsed hoop, such as that shown in FIGS. 7A-7F, and is collapsed, just as in FIGS. 7A-7F, to form two ends that are linked by a wire.

FIG. 16 is a detail of an embodiment, aortic prosthesis system 300, of the invention wherein ligature 302 is a collapsed hoop, such as that shown in FIGS. 7A-7F, and just as in FIGS. 7A-7F, forms two ends 304, 306 that are linked by wire 228. The hoop, in its collapsed form, extends through loops 308, and linkage of ends 304, 306 by wire 228 radially constrains the stent graft until wire 228 is removed, such as by longitudinal retraction from ends 304, 306 of ligature 302 so that they are no longer linked. While, as shown in FIG. 16, loops 308 can be on stent 310 at struts 312, in an alternative embodiment, not shown, loops 308 associated with each ligature 302 can be on only one strut 312, for example, or some portion of struts 312 of stent 310.

Figure 17:
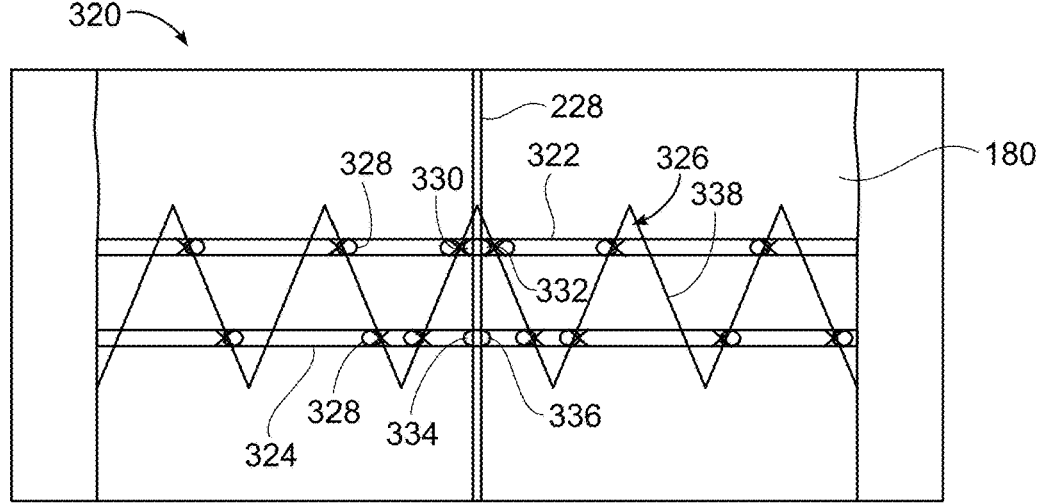
FIG. 17 is a detail of an embodiment of the aortic prosthesis system of the invention wherein a plurality of ligatures form collapsed hoops that circumscribe a stent graft at different longitudinal positions of a stent.

FIG. 17 is a detail of an embodiment of the aortic prosthesis system 320 of the invention wherein a plurality of ligatures 322, 324 form collapsed hoops that circumscribe the stent graft of the aortic prosthesis system 320 at different longitudinal positions of stent 326 along the stent graft. In the instance of FIG. 17, two ligatures 322, 324 circumscribe stent graft. Ligatures 322, 324 extend through loops 328, and linkage of ends 330, 332, and 334, 336 of ligatures 322, 324, respectively, by wire 228 radially constrains the stent graft until wire 228 is removed, such as by longitudinal retraction of wire 228 from ends 330, 332, and 334, 336 of ligatures 322, 324, respectively, so that they are no longer linked. While, as shown in FIG. 17, loops 328 can be on each strut 338 of stent 326, in an alternative embodiment, not shown, loops associated with each ligature can be on only one strut, for example, or some portion of struts of the stent, such as at every other strut.

Figure 18:
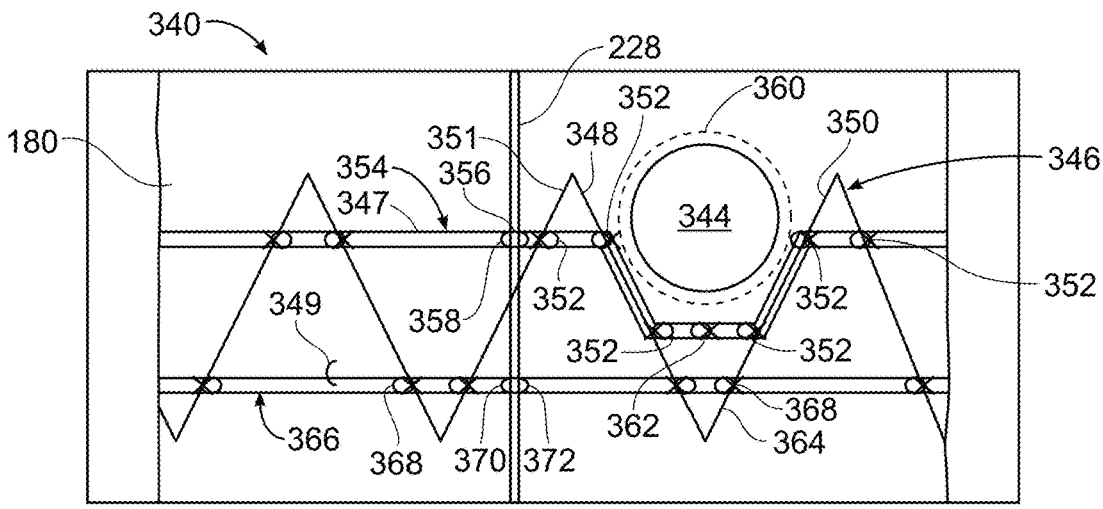
FIG. 18 is a detail of an embodiment of the aortic prosthesis system of the invention wherein a graft component of a stent graft defines a fenestration and wherein the fenestration is nested between struts at a proximal end of a stent of the stent graft.

FIG. 18 is a detail of an embodiment, aortic prosthesis system 340, of the invention wherein graft component 180 of the stent graft defines fenestration 344 and wherein fenestration 344 is nested at stent 346 between struts 348, 350 at proximal end 351 of stent 346 of the stent graft. In this embodiment, loops 352 are fixed to struts 350 at positions that prevent first ligature 354 from traversing fenestration 344, thereby leaving fenestration 344 open for positioning at a branch blood vessel, for example, and subsequent cannulation. In this embodiment, first ligature 354 is a collapsed hoop that extends through loops 352, and ends 356, 358 of first ligature 354 are linked by wire 228 to thereby constrain stent 346 and the stent graft of which stent 346 is a component. Wire 228 is radially spaced from fenestration 344 to avoid obstruction of fenestration 344 during subsequent cannulation with, for example, a branch stent or stent graft, neither of which are shown. Fenestration 344 is shown in an open position in FIG. 18, and can be maintained in an open position, despite radial constraint by ligature 354, by a suitable support, such as, for example, a circular support 360 extending about a perimeter of fenestration 344. Circular support 360 can be fabricated of a suitable material, such as Nitinol, and can be fixed to the perimeter of fenestration by suitable means, such as a suture thread, as described above. Preferably, circular support 360 is deformable, or at least partially deformable during constraint by ligature 354. In this instance, circular support 360 can be formed of a suitable material, such as Nitinol. Further, loop 362 is fixed to graft material 342 of the stent graft between loops 352 fixed to struts 350 toward the distal end of stent 346. Loop 362 prevents collapse of fenestration 344 within the outer perimeter of stent graft, as described with respect to FIGS. 21 and 22, below. Although not necessarily present, second ligature 366 extends through loops 368 at a longitudinal distance from and distal to first ligature 354. Second ligature 366 also radially constrains stent graft when ends 370, 372 of second ligature 366 are linked by wire 228. In alternative embodiments, not shown, collapsed hoops can be partially or completely replaced by single-stranded ligatures, as discussed in embodiments described above, where the ligature partially or completely circumscribes stent graft and ligature loops of the ligatures are linked by wire. In another embodiment, fenestration 344 can be nested between struts 448,350 at distal end 364 of stent 346 of the stent graft. In this embodiment, the positions of collapsed hoops (or ligatures) are reversed from those shown in FIG. 18.

Figure 19:
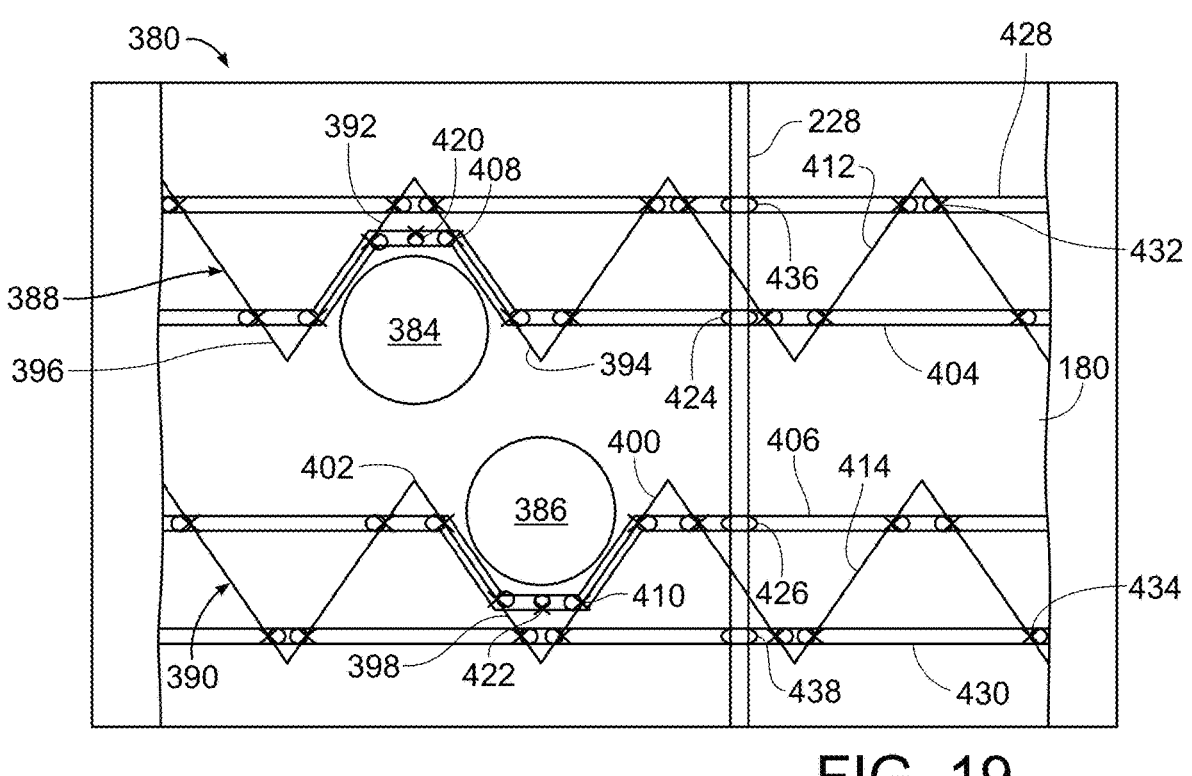
FIG. 19 is a detail of another embodiment of the aortic prosthesis system of the invention, wherein graft material of a stent graft component of the aortic prosthesis system includes two fenestrations, and wherein each fenestration is nested between struts of different stents of the stent graft, but are in close proximity to each other.

FIG. 19 is a detail of another embodiment, aortic prosthesis system 380, of the invention, wherein graft material 180 of the stent graft component of aortic prosthesis system 380 includes two fenestrations 384,386, and wherein each fenestration is nested between respective struts of different stents 388,390 of the stent graft, but are in close proximity to each other. In this embodiment, first fenestration 384 is nested between struts 392,394 at distal end 396 of first, relatively proximal stent 388 of the stent graft, and second fenestration 386 is nested between struts 398,400 at proximal end 402 of second, relatively distal stent 390 of the stent graft. While fenestrations 384,386 shown in FIG. 19 are radially offset from each other, it is to be understood that fenestrations 384,386 can be arranged so that fenestrations

384,386 are aligned with each other along a longitudinal length of the stent graft, in which case the proximal and distal apices of the respective stents might also be aligned to avoid interference for the struts with passage through, or cannulation of fenestrations 384,386. Ligatures 404, 406 extend through loops 408,410 fixed to struts 412,414 of respective stents 388,390, and pass around respective fenestrations 384,386. Loops 420,422 at graft material 382 between loops 408,410 support graft material 180 to prevent collapse of fenestrations 384,386 to within the stent graft, as also described in FIG. 18. Ligatures 404,406 have respective ends 424,426 that are linked by wire 228. Ligatures 428,430 extend about the opposite ends of each of stents 388,390 through respective loops 432, 434 and are linked at ends 436, 438, respectively. Linking of ends 424, 426, 436, and 438 by wire 228 radially constrains stents 388,390, which can be released by withdrawal of wire 228 from ends 424, 426, 436, and 438. Also as with FIG. 18, it is also to be understood that each stent can also be constrained by a second collapsed hoop or ligature extending through a different set of loops fixed to struts than the set of loops through which first collapsed hoop or ligature extends. The second ligature can have a different length and can have ends linked by a different wire, so that radial expansion of the stent graft can take place in stages, by removing a first wire from the first ligature ends, and then removing a second wire from the second ligature ends. It is also to be understood that the collapsed hoops or ligatures can be configured so that each includes component parts, whereby each component part extends only partially about the stent graft.

Figure 20:
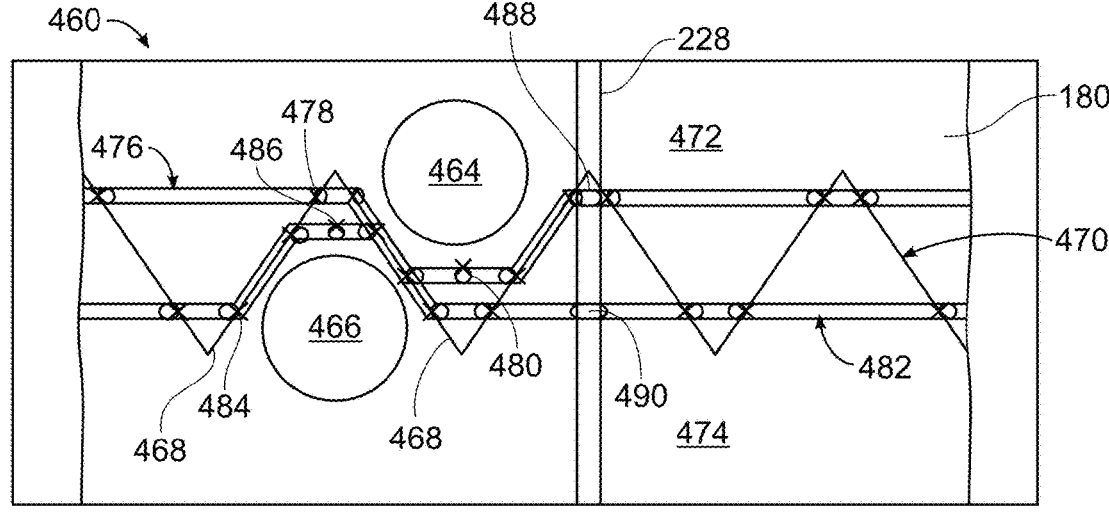
FIG. 20 is a detail of still another embodiment of the aortic prosthesis system of the invention, wherein the graft material of a stent graft component of the aortic prosthesis system includes two fenestrations, each of which is nested between struts of a single stent.

FIG. 20 is a detail of still another embodiment, aortic prosthesis system 460, of the invention, wherein graft material 180 of the stent graft component of aortic prosthesis system 460 defines two fenestrations 464, 466, each of which is nested between struts 468 of stent 470. As shown in FIG. 20, first fenestration 464 is nested between struts 468 on proximal side 472 of stent 470, and second fenestration 466 is nested between struts 468 on distal side 474 of stent 470. First ligature 476 is a collapsed hoop that extends through loops 478 fixed to struts 468 and through loop 480 fixed to graft material 180 at distal end of first fenestration 464, and second ligature 482 is a collapsed hoop that extends through loops 484 fixed to struts 468 and through loop 486 that is fixed to graft material 180 at the proximal end of second fenestration 466. Wire 228, radially spaced from first fenestration 464 and second fenestration 466, links ends 488, 490 of respective first ligature 476 and second ligature 482 to thereby radially constrain the stent graft. As in the embodiments discussed above, the collapsed loops of the ligatures of this embodiment can be substituted with single-stranded ligatures that at least partially surround the stent graft and are linked at respective ends to radially constrain the stent graft.

Figure 21:
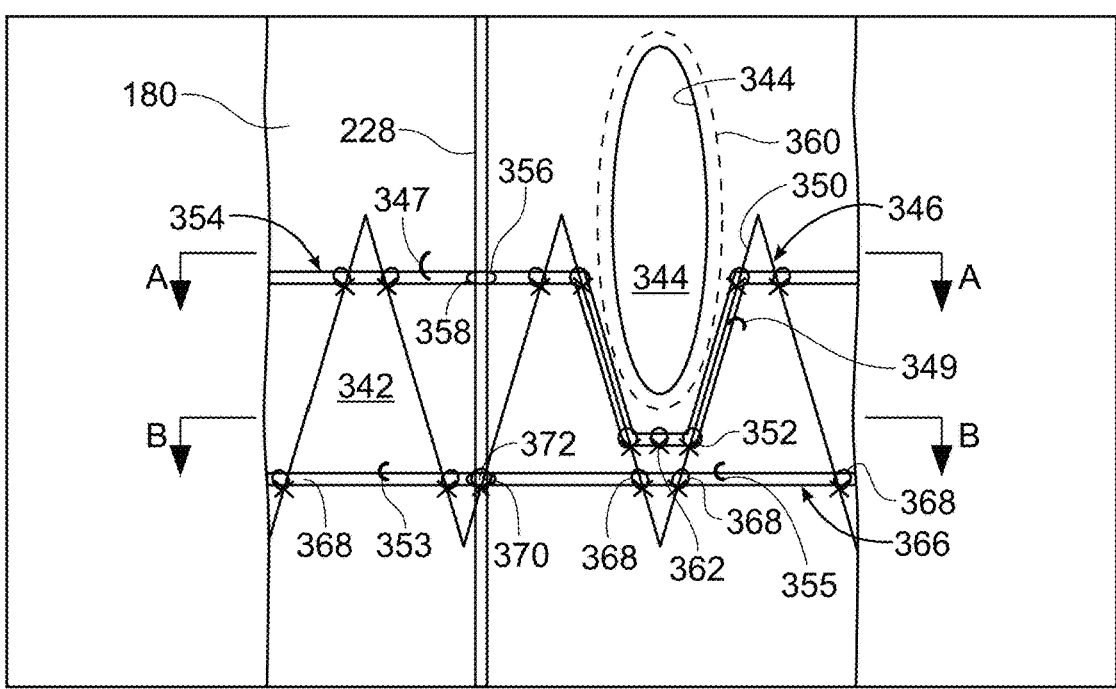
FIG. 21 is an embodiment of the invention shown in FIG. 18, wherein the fenestration at least partially collapses when the stent graft is radially constrained by a collapsed hoop.

FIG. 21 is an embodiment of the invention shown in FIG. 18, wherein fenestration 344 at least partially collapses when the stent graft is radially constrained by ligatures 354, 366. As can be seen in FIG. 21, fenestration 344 radially narrows by virtue of radial constraint causes by linking ends 356, 358 of ligature 354 and ends 370, 372 of ligature 366 by wire 228. In addition, as shown in FIGS. 21A and 21B, taken along lines AA and BB, respectively, of FIG. 21, the periphery of fenestration 344 is raised from external surface 345 of the stent graft. This raised profile is causes, at least in part, by loop 362 fixed to graft material 342 between loops 352 fixed to struts 350 and at distal end 347 of fenestration 344. Loop 362 supports graft material 342 while fenestration 344 is in a collapsed position, thereby preventing graft material 342 that defines fenestration 344 from becoming recessed within the stent graft when the stent graft is radially constrained by ligatures 354, 366. A raised profile of graft material 342 defining fenestration 344 assists cannulation of fenestration 344 during implantation, for example, of a branch stent or stent graft. FIG. 21C is a detail of FIG. 21A, showing suture ends 356, 358 linked by wire 228. FIG. 21D is a detail of FIG. 21B, showing suture ends 370, 372 linked by wire 228.

Figure 22:
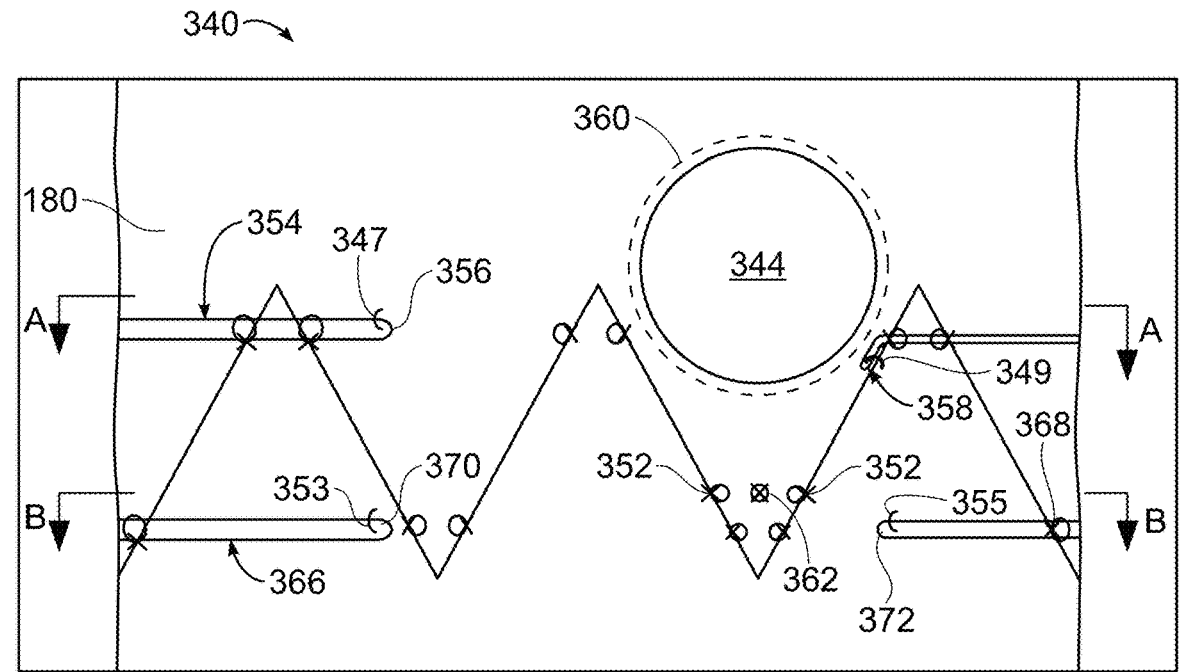
FIG. 22 is the embodiment of FIG. 20 upon removal of the wire linking the ends of collapsed hoops, thereby relieving the stent graft from the radially constrained position shown in FIG. 20.

FIG. 22 is the embodiment of FIG. 21 upon removal of wire 228 linking ends 356, 358 of first ligature 354 and ends 370, 372 of second ligature 366, thereby relieving the stent graft from the radially constrained position shown in FIG. 21. As can be seen, fenestration 344 assumes a relaxed position upon release of the stent graft from its radially constrained position. Anchor stitches 347,349 hold ends 356,358 of first ligature 354 and anchor stiches 353,355 hold ends 370,372 of second ligature 366 so that first ligature 354 and second ligature 366 stay secured to the stent graft following release of first ligature 354 and second ligature 366 by retention of wire 228. FIGS. 22A and 22B are profiles of the detail of FIG. 22 taken along lines AA and BB of FIG. 22. As can be seen from FIGS. 22A and 22B, graft material surrounding fenestration is no longer raised, as it is in FIG. 20A, nor is it gathered at loop, as it is in FIG. 21B.

Figure 23:
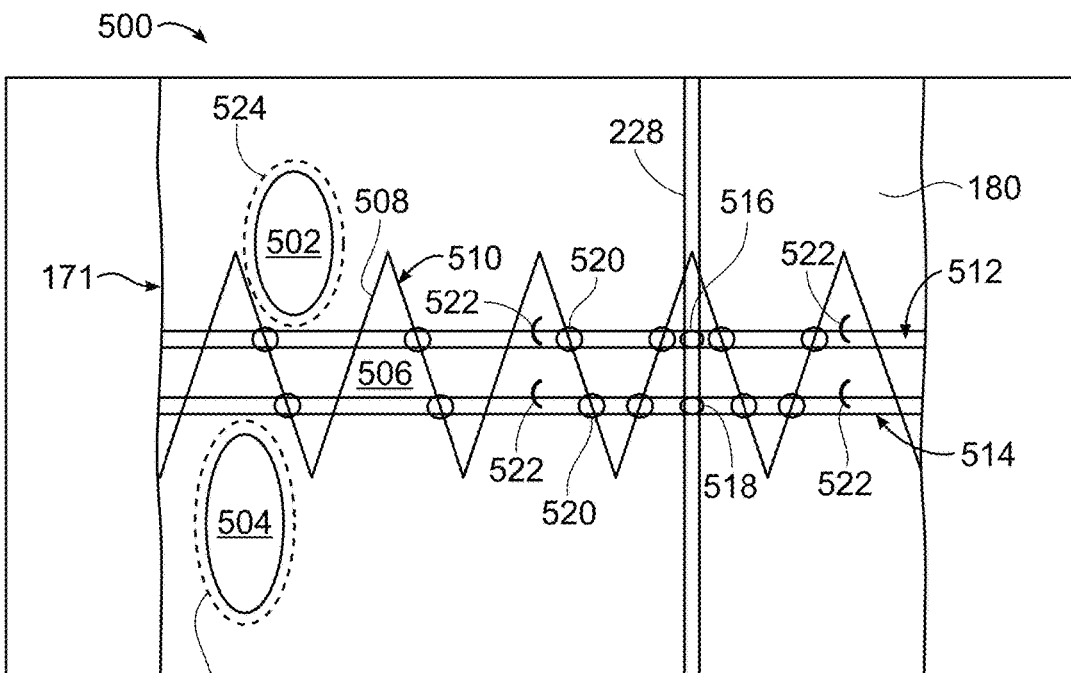
FIG. 23 is another embodiment of the aortic prosthesis system of the invention, wherein fenestrations defined by a graft component of a stent graft of the aortic prosthesis system are partially nested between struts on proximal and distal sides of a stent component of the stent graft, and wherein ligatures are collapsed hoops that are linked by a wire to thereby constrain the stent graft and at least partially collapse the fenestrations.

FIG. 23 is another embodiment, aortic prosthesis system 500, of the invention, wherein fenestrations 502, 504 are defined by graft component 180 of a stent graft 171 of aortic prosthesis system 500. Fenestrations 502, 504 are partially nested between struts 508 of stent component 510 of the stent graft, and wherein ligatures 512, 514 are collapsed hoops that define ends 516, 518, respectively, that extend through loops 520 fixed to struts 508 and are linked by wire 228 to thereby radially constrain the stent graft and at least partially collapse fenestrations 502, 504. Fenestrations 502, 504 are on proximal and distal sides, respectively, of stent 510, and ligatures 512, 514 extend around the stent graft without obstructing fenestrations 502, 504. Anchor stitches 522 in graft material 506 extend through the collapsed loops of ligatures 512, 514, and are intended to secure ligatures 512, 514 to the stent graft once wire 228 has been withdrawn, thereby releasing ends 516, 518 of ligatures 512, 514.

Figure 24:
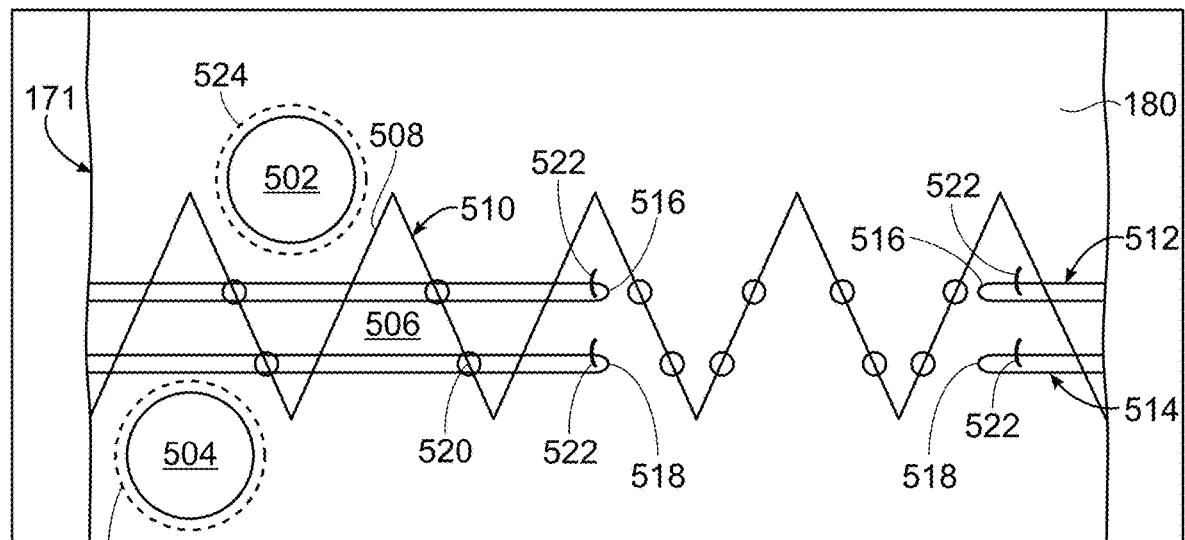
FIG. 24 is the embodiment shown in FIG. 23 following removal of wire linking ends of ligatures.

FIG. 24 is the embodiment shown in FIG. 23 following removal of wire 228 linking ends 516, 518 of ligatures 512, 514. As can be seen, following removal of wire 228, fenestrations 502, 504, which are supported by Nitinol hoops 524 about the periphery of fenestrations 502, 504, and are fixed to graft component 180 of the stent graft by suitable means, such as by stitching or a suitable adhesive, expand to their fully-open shape. Anchor stitches 522 extending through ends 516, 518 retain ligatures 512, 514 in close proximity to stent graft 171 after implantation is complete.

Figure 25:
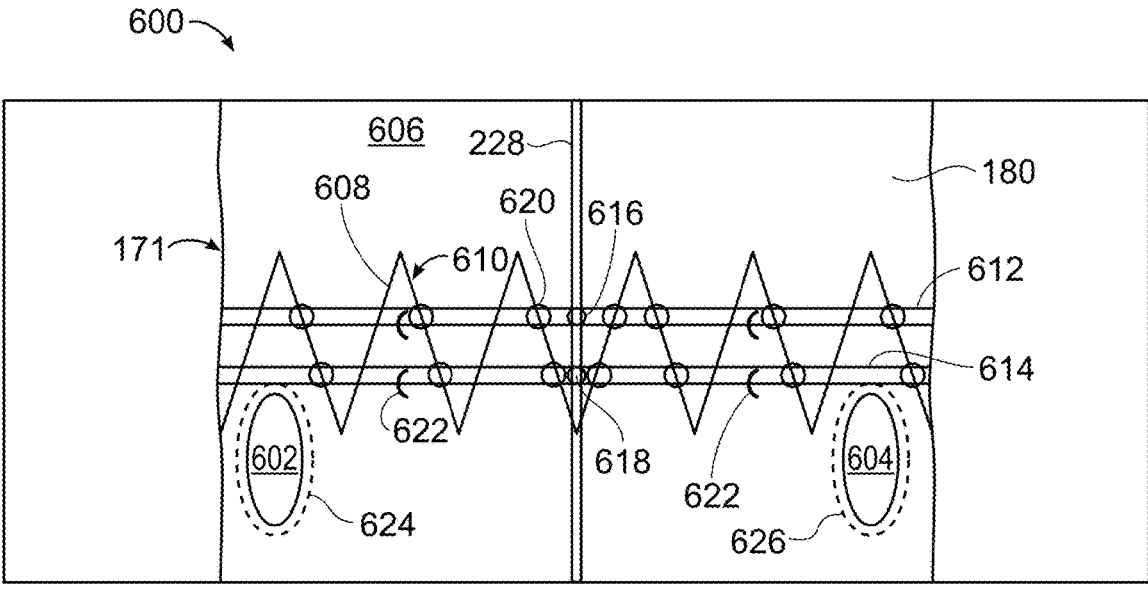
FIG. 25 is another embodiment of the aortic prosthesis of the invention, wherein fenestrations defined by a graft component of a stent graft of the aortic prosthesis system are both partially nested between struts on a distal side of a stent component of the stent graft, and wherein ligatures are collapsed hoops that are linked by a wire to thereby constrain the stent graft and at least partially collapse the fenestrations.

FIG. 25 is another embodiment, aortic prosthesis system 600, of the invention, wherein fenestrations 602, 604 are defined by graft component 180 of a stent graft of aortic prosthesis system 600. Fenestrations 602, 604 are partially nested between struts 608 on one sided. In this case, the distal side of stent component 610 of the stent graft, and wherein ligatures 612, 614 are collapsed hoops that define ends 616, 618, respectively, that extend through loops 620 fixed to struts 608 and are linked by wire 228 to thereby radially constrain the stent graft and at least partially collapse fenestrations 602, 604. Ligatures 612, 614 extend around the stent graft without obstructing fenestrations 602, 604. Anchor stitches 622 in graft material 606 extend through the collapsed loops of ligatures 612, 614, and are intended to secure ligatures 612, 614 to the stent graft once wire 228 has been withdrawn, thereby releasing ends 616, 618 of ligatures 612, 614.

Figure 26:
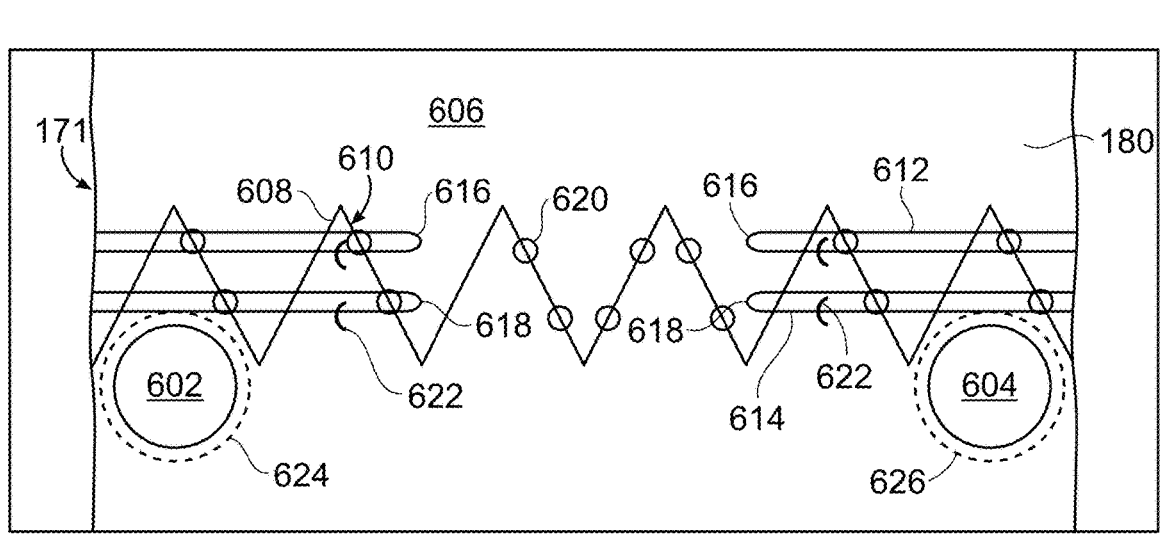
FIG. 26 is the embodiment shown in FIG. 25 following removal of wire linking ends of ligatures.

FIG. 26 is the embodiment shown in FIG. 25 following removal of wire 228 linking ends 616, 618 of ligatures 612, 614. As can be seen, following removal of wire 228, fenestrations 602, 604, which are supported by Nitinol hoops 624,626 about the periphery of fenestrations 602, 604, respectively, and are fixed to graft component 180 of the stent graft by suitable means, such as by stitching or a suitable adhesive, expand to their fully-open shape. Anchor stitches 622 extending through ends 616, 618 retain ligatures 612, 614 in close proximity to stent graft 180 after implantation is complete.

It is to be noted that, generally, at least three millimeters is to be maintained between fenestrations, between fenestrations and struts of stents, and longitudinally between stents along a stent graft, although, in some instances, no distance is required or maintained. Other, optional features of the delivery system can include, for example:

Main Body Stent Graft: Summary of Features and Inclusion/Exclusion Criteria

| TREO Fenestrated Graft Features | Options |
| --- | --- |
| Delivery System FR Size | 19 Fr |
| Available Graft Lengths | 80 mm, 100 mm, 120 mm and 140 mm |
| Available Graft Diameters | 24 mm, 26 mm, 28 mm, 30 mm, 33 mm and 36 mm |
| Number of Fenestrations | 1 to 5 |
| Fenestration Sizes | 6 mm, 7 mm, 8 mm and 9 mm |
| Re-enforced Fenestrations | Fenestration openings re-enforced with Nitinol Rings |
| Fenestration Marker Bands | Placed on the Rings |
| | 3 at 12 o'clock |
| | 1 at 3 o'clock |
| | 1 at 6 o'clock |
| AP Markers | At Proximal End of Graft |
| | 2 Cylindrical Markers Anterior |
| | 1 Cylindrical Marker Posterior in-line with Anterior |
| | 1 Cylindrical Marker Left Lateral |

Methods suitable for delivery and cannulation of the embodiments shown in FIGS. 11-26 are the same as those described above, such as the method described above with reference to FIGS. 10A-10E.

Figure 27:
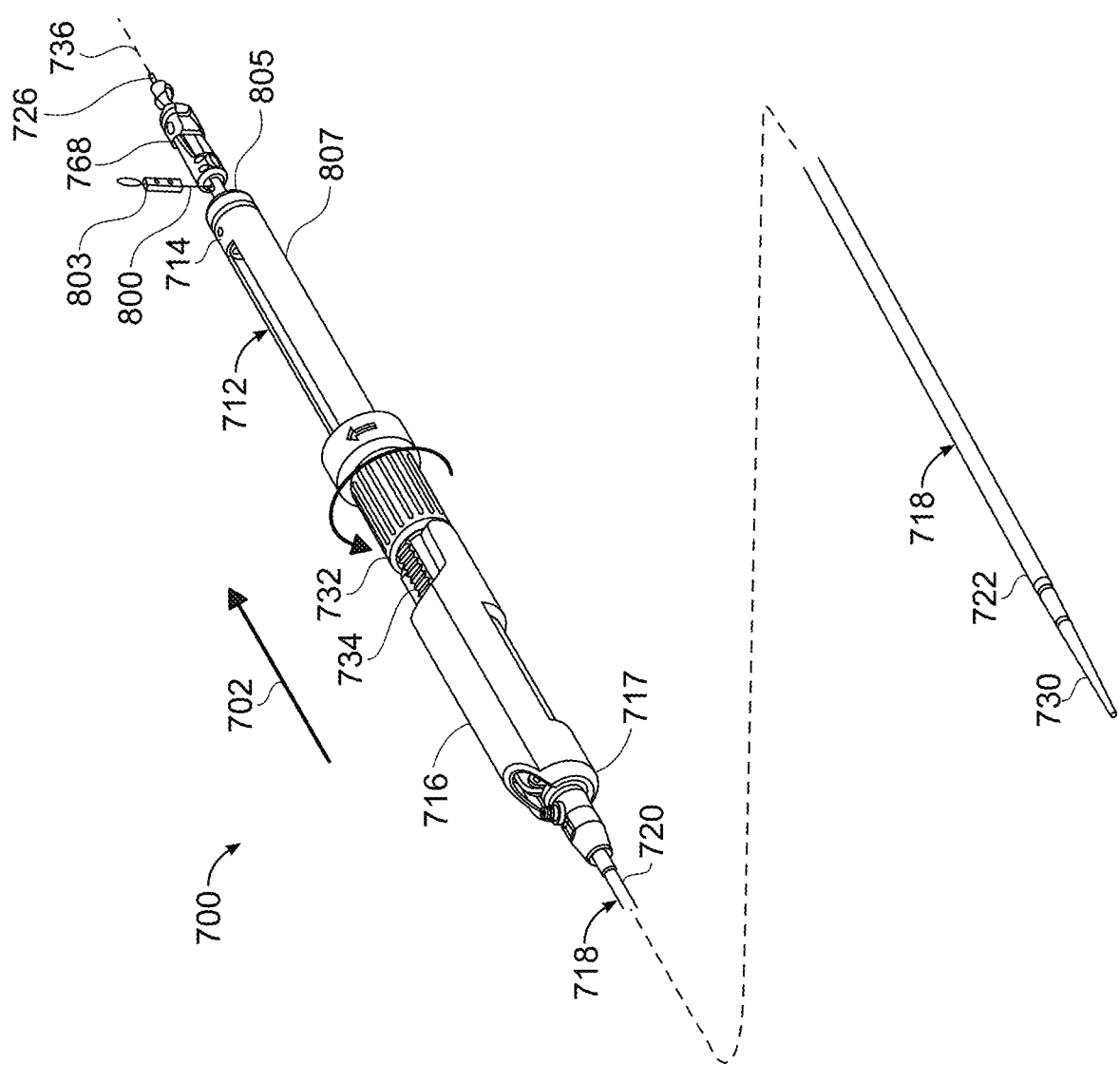
FIG. 27 is a perspective view of one embodiment of a delivery system of the invention for implanting an arterial stent graft.

Another embodiment of a delivery system of the invention for implanting a stent graft prosthesis is shown in FIG. 27. As shown therein, delivery system 700 includes longitudinal body 712 having proximal handle 714 and distal handle 716 at distal end 717 of longitudinal body 712. Introducer sheath 718 (an introducer sheath is an embodiment of a radial constraint) extends distally from distal handle 716, and includes proximal end 720 and distal end 722. Guidewire catheter 724 (FIG. 29) includes proximal end 726 and distal end 728 (FIG. 28), and extends from distal end 716 of longitudinal body 712. Guidewire catheter 724 extends within introducer sheath 718 and through longitudinal body 712. Proximal end 726 (FIG. 28) of guidewire catheter 724 extends proximally from proximal handle 714 of longitudinal body 712.

Nose cone 730 is fixed to distal end 728 (FIG. 28) of guidewire catheter 724. Guidewire catheter 724 and nose cone 730 define a luminal channel through which a guidewire (not shown) can extend. Introducer sheath 718 is movable along longitudinal axis 736 of delivery system 700 in a proximal direction 702 relative to a surgeon operating delivery system 700, by retracting introducer sheath 718 relative to distal handle 16 of longitudinal body 712. Wire handle 803 is attached to proximal end of wire 800. Proximal clasp assembly 768 is proximal to proximal handle 714, and controls release of proximal apices of bare stent 756 at proximal end 740 of stent graft 738 according to an embodiment of the invention.

Figure 27A:
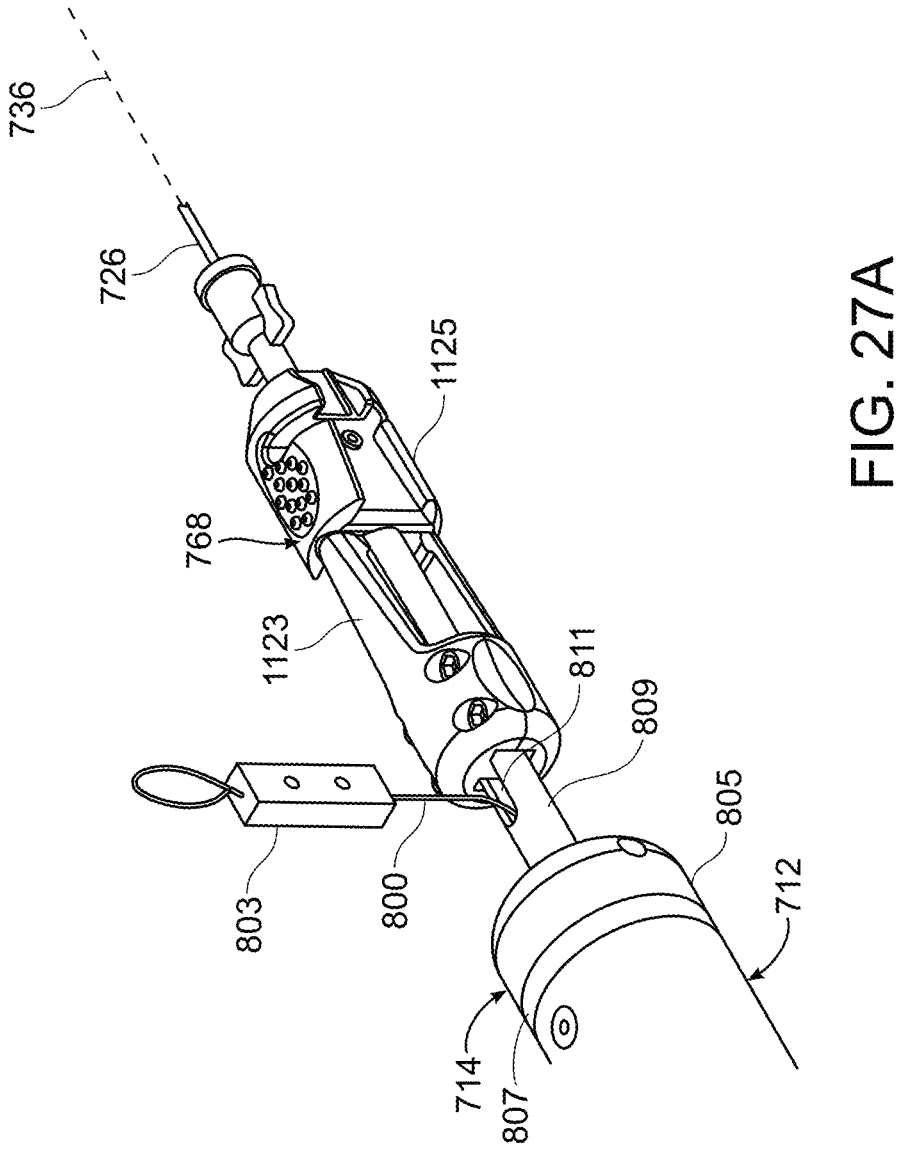
FIG. 27A is a perspective view of a proximal end of one embodiment of a delivery device of the invention.

FIG. 27A is a detail of proximal handle 714 and proximal clasp assembly 768. As shown therein, proximal handle 714 is fixed to the proximal end of longitudinal body 712 and includes proximal handle end cap 805 and proximal handle body 807. Proximal stem 809 extends proximally from proximal handle end cap 805 and defines slot 811. Wire 800 extends through slot 811 and is fixed to wire handle 803 at the proximal end of wire 800. Outer coupling 1123 and fixed component 1125 are in mating relation to each other at a proximal end of proximal stem 809. A proximal end of outer control tube 1126 (seen in FIG. 27C) is fixed to outer coupling 1123, and a proximal end 726 of guidewire catheter 724 is fixed to fixed component 1125. A proximal end of proximal stem 809 is also fixed to fixed component 1125. Guidewire catheter 724 extends through longitudinal body 712, proximal handle 714, outer coupling 1123, and fixed component 1125. It is to be understood that the detail of FIG. 27A is the same as that shown in FIGS. 77A, 77B, and 77C.

Figures 27B, 27C:
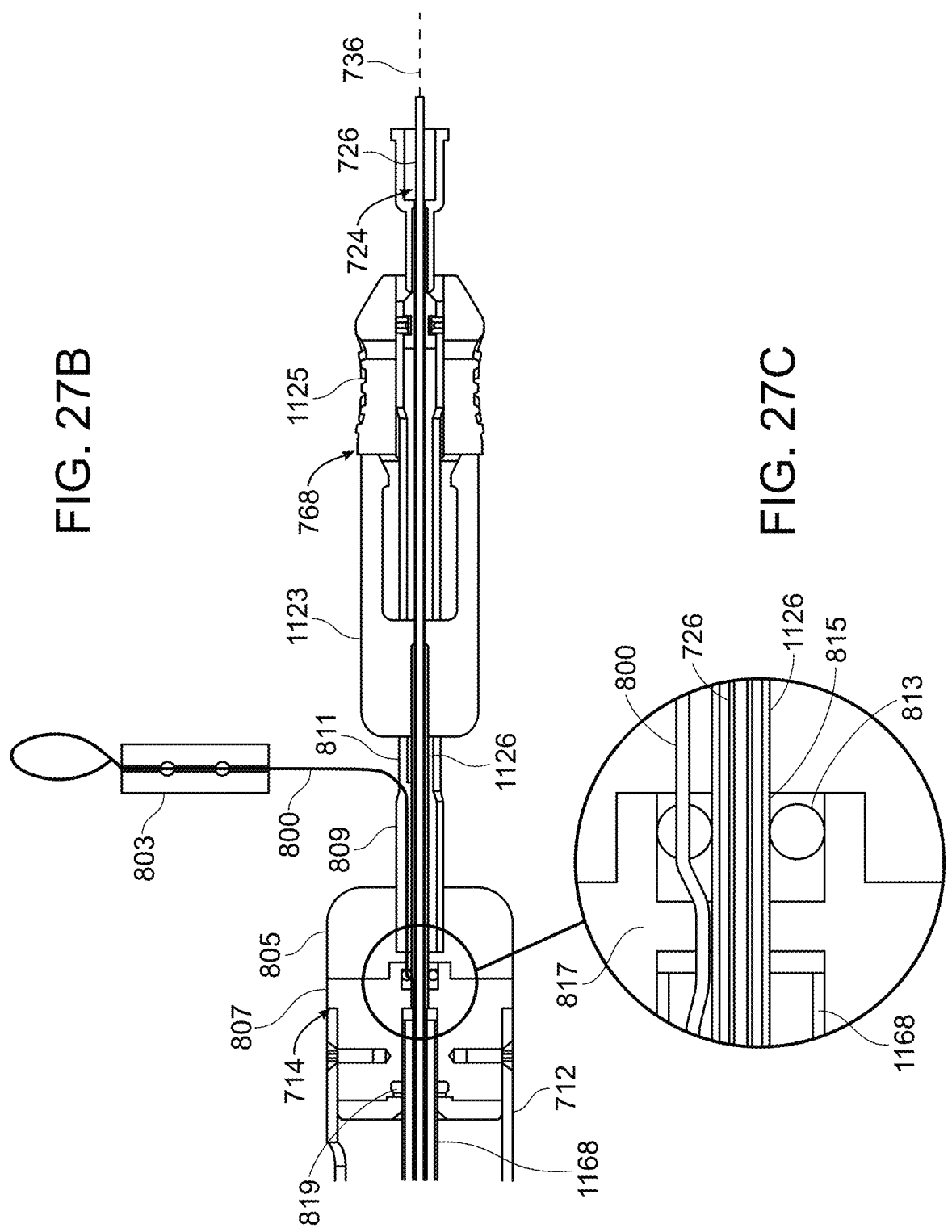
FIG. 27B is a cross-sectional view of the proximal end of the delivery device shown in FIG. 27A.
FIG. 27C is a detail of the cross-sectional view shown in FIG. 27B.
Figures 27D, 27E, 27F, 27G:
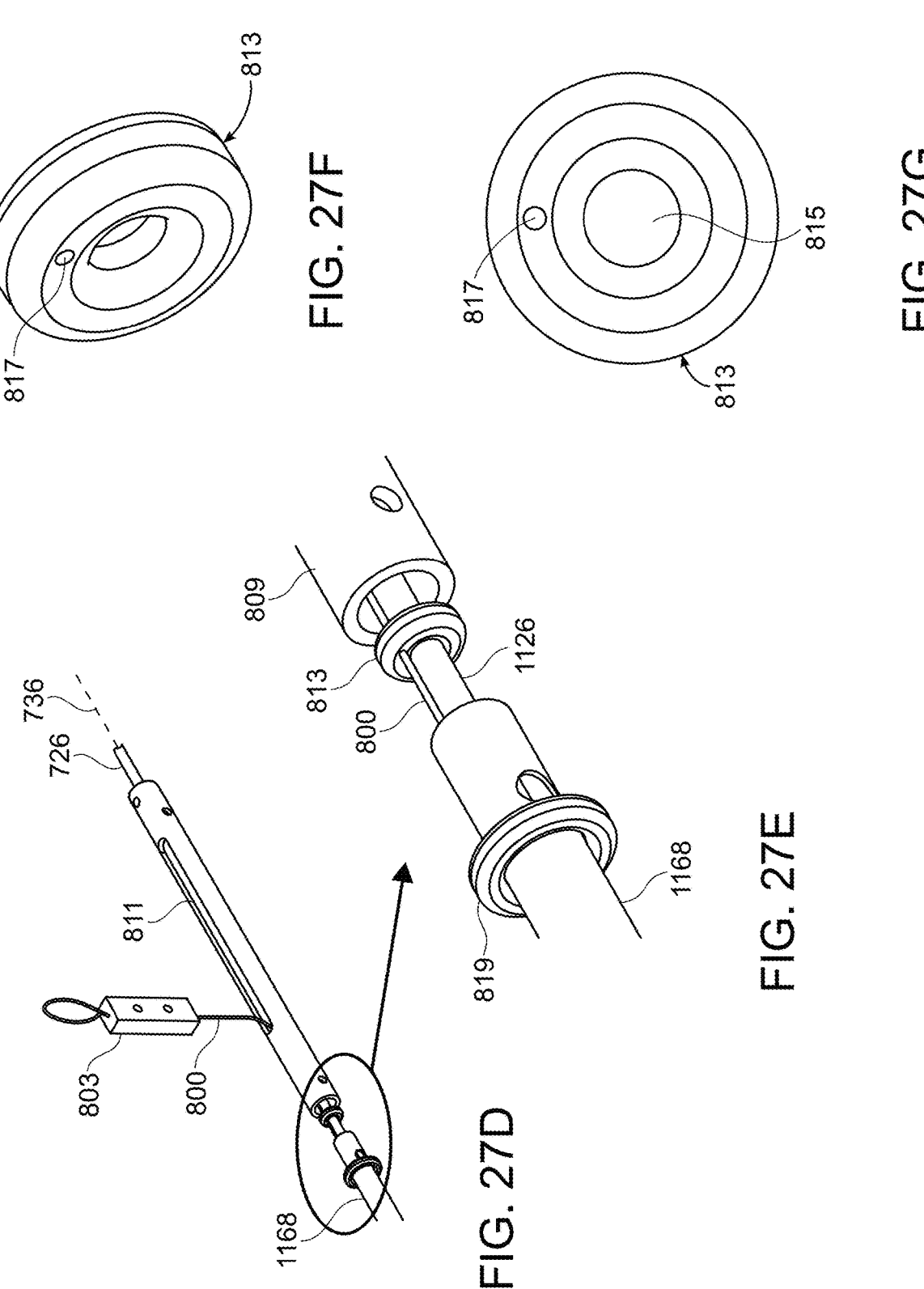
FIG. 27D is a perspective view of a portion of the proximal end of the delivery device shown in FIG. 27A.
FIG. 27E is a detail of a portion of the perspective view shown in FIG. 27D.
FIG. 27F is a perspective view of a proximal gasket shown in FIGS. 27A through 27E.
FIG. 27G. is an end view of the proximal gasket shown in FIG. 27F.

FIG. 27B is a cross section of the detail shown in FIG. 27A, and FIG. 27C is a detail of FIG. 27B. As can be seen in FIGS. 27B and 27C, proximal handle 714 is fixed to a proximal end of pushrod 774. Outer control tube 1126 and proximal end 724 of guidewire catheter 724 extend through proximal handle 714 and pushrod 774. Wire 800 runs parallel to, and outside of outer control tube 1126. As can be seen in FIGS. 27B, 27D, and 27E, distal gasket 819 extends about a proximal end of pushrod 774 and, as shown in FIG. 27B, distal gasket 819 seals a juncture between pushrod 774 and proximal handle body 807. As can be seen in FIGS. 27F and 27G, proximal gasket 813 includes major opening 815 and minor opening 817. As can be seen in FIGS. 27C and 27E, outer control tube 1126 extends through major opening 815 of proximal gasket 813, and wire 800 extends through minor opening 817. As shown in FIG. 27C, major opening 815 seals the juncture between outer control tube 1126 and proximal handle body 807, while minor opening 817 seals the junction between wire 800 and proximal handle body 807. Proximal gasket 813 prevents leakage of blood from delivery system 700. It is to be understood that proximal gasket can be employed as a component of all embodiments of the delivery device of the invention that include a wire extending parallel to a guidewire catheter or outer control tube of the invention.

Figure 28:
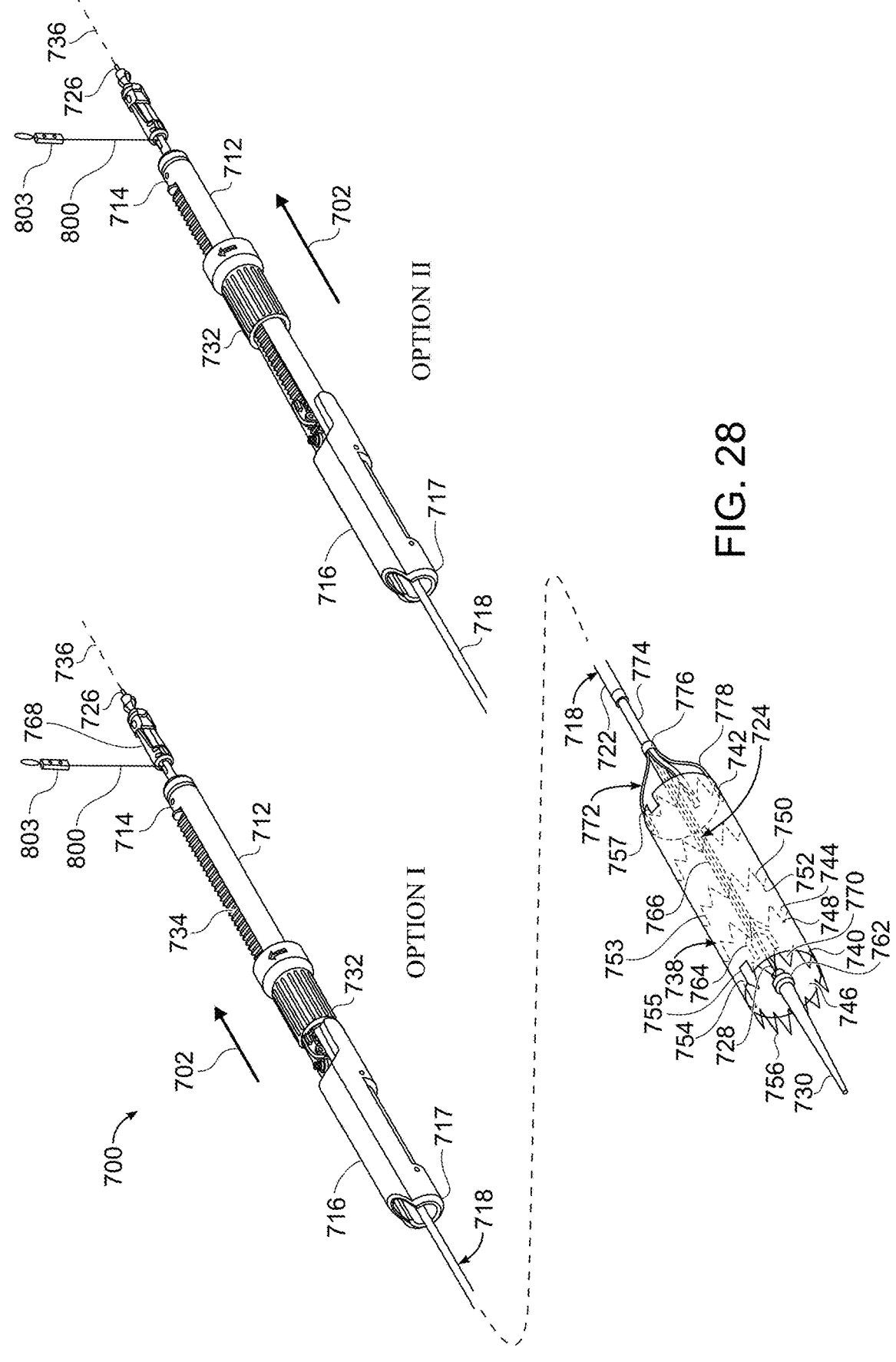
FIG. 28 is a perspective view of the delivery system of FIG. 27 showing two options for retracting an introducer sheath from about the arterial stent graft.

In one embodiment, for example, as shown in FIG. 28, introducer sheath 718 can be retracted by rotation of lead screw nut 732 that is threaded in mating configuration with track 734 to which introducer sheath 18 is fixed, directly or indirectly. Option I of FIG. 28 shows rotation of a lead screw nut 732 causing longitudinal movement of track 734 in direction 702 and, therefore, introducer sheath 718 along longitudinal axis 736 of delivery device 700. Alternatively, lead screw nut 732 can be drawn back directly along longitudinal body 712 in direction 702 without rotation to thereby retract introducer sheath 718, as shown in Option II. As can be seen, in either option, retraction of introducer sheath 718 at least partially exposes stent graft 738, while guidewire catheter 724 and nose cone 730 remain fixed relative to longitudinal body 712.

In an alternative embodiment, as described above, longitudinal body 712 includes a proximal handle component that directs guidewire catheter 724 and, consequently, stent graft 738 distally from within distal end 722 of introducer sheath 718 to thereby release stent graft 738. As with the embodiment represented in FIGS. 27 and 28, once stent graft 738 is released, guidewire catheter 724 and nose cone 30, as well as introducer sheath 718 are all retracted and withdrawn from the subject.

As shown in FIG. 28, stent graft 738 includes proximal end 740 and distal end 742. Luminal graft component 744 of stent graft 738 defines lumen 746. Stents 748 are self-expanding and are formed of struts 750 that are connected to form proximal apices 752 and distal apices 754. In an embodiment, stent graft 738 includes bare stent 756 at proximal end 740. Bare stent 756 is secured to luminal graft component 744 at proximal end 740 of stent graft 738 by distal apices 754 of bare stent 756, for example, with sutures, biocompatible adhesive, or other suitable techniques known to those skilled in the art. Luminal graft component 744 defines a lumen extending from proximal end 740 to distal end 742. In certain embodiments, luminal graft component 744 can include scalloped portions 755, 757, at proximal end 740 and distal end 742, respectively. Luminal graft component 744 is formed of a suitable material, such as are known to those skilled in the art, including, for example, expanded polytetrafluoroethylene (PTFE), such as ePTFE, and polyethylene terephthalate (PET), such as woven polyester. Stents 748 and bare stent 756 are formed of a suitable material, such as shape memory alloys (Nitinol) or stainless steel.

Figure 29:
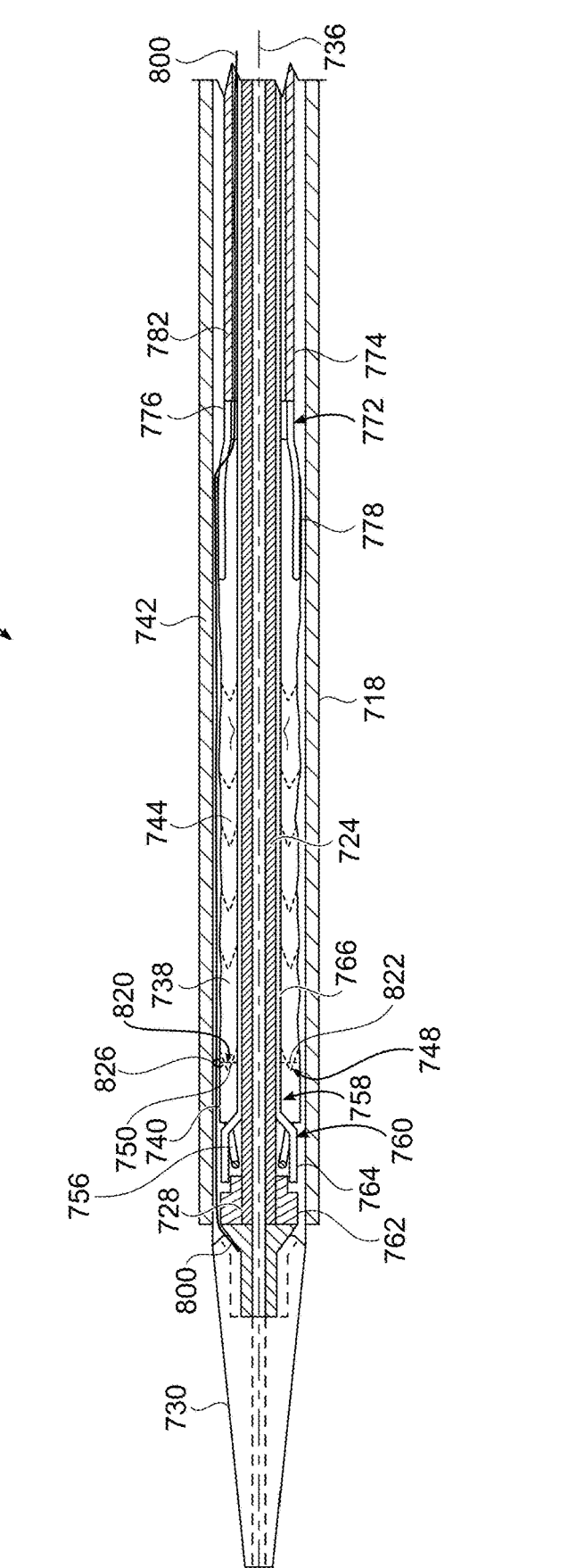
FIG. 29 is a cross-sectional view of the delivery system shown in FIG. 27 before deployment of the stent graft that is radially constrained by one embodiment of a method and system of the invention.

FIG. 29 is a cross-sectional view of a distal portion of delivery device 700 prior to deployment of stent graft 738 from within introducer sheath 718. In one specific embodiment, bare stent 756 is in a first, captured state, in which proximal apices of bare stent 756 are fixed to apex capture assembly 758 of delivery device 710. In one embodiment, apex capture assembly 758 includes proximal capture component 760 and distal capture component 762. Proximal capture component 760 includes tines 764 that extend distally from apex capture catheter 766, which surrounds guidewire catheter 724 and is fixed to guidewire catheter 724 by proximal clasp assembly 768, shown in FIG. 28, at proximal end 726 of guidewire catheter 724. When in a captured state, shown in FIG. 29, tines 764 extend through openings 770 (FIG. 28) defined by bare stent 756 at luminal graft component 744 of stent graft 738, thereby preventing radial expansion of bare stent 756 at proximal end 740 of stent graft 738. Release of apex capture catheter 766 from guidewire catheter 724 at proximal clasp assembly 768 enables proximal movement of apex capture catheter 766 and proximal capture component 760 from distal capture component 762 to thereby release bare stent 756 from tines 764, thereby releasing bare stent 756 from the captured state to a released state.

Torque component 772, includes pushrod 774, hub 776, and at least two arms 778. Pushrod 774 has proximal end (not shown) and distal end 782, and extends about guidewire catheter 724 and distally from proximal handle 714 (FIG. 28). Although not shown, proximal end of pushrod 774 is fixed to proximal handle 714 of longitudinal body 712. Proximal handle 714 is rotatable about longitudinal body 712 to thereby cause pushrod 774 to rotate about guidewire catheter 724. Optionally, proximal handle 714 can be locked with guidewire catheter 724, and apex capture catheter 766, whereby rotation of proximal handle 714 causes axial rotation of guidewire catheter 724 and apex capture catheter 766. Hub 776 defines lumen 788 (FIG. 30) and is fixed to distal end 782 of pushrod 774. At least two arms 778 extend distally from hub 776 and are distributed radially about apex capture catheter 766.

Figure 30:
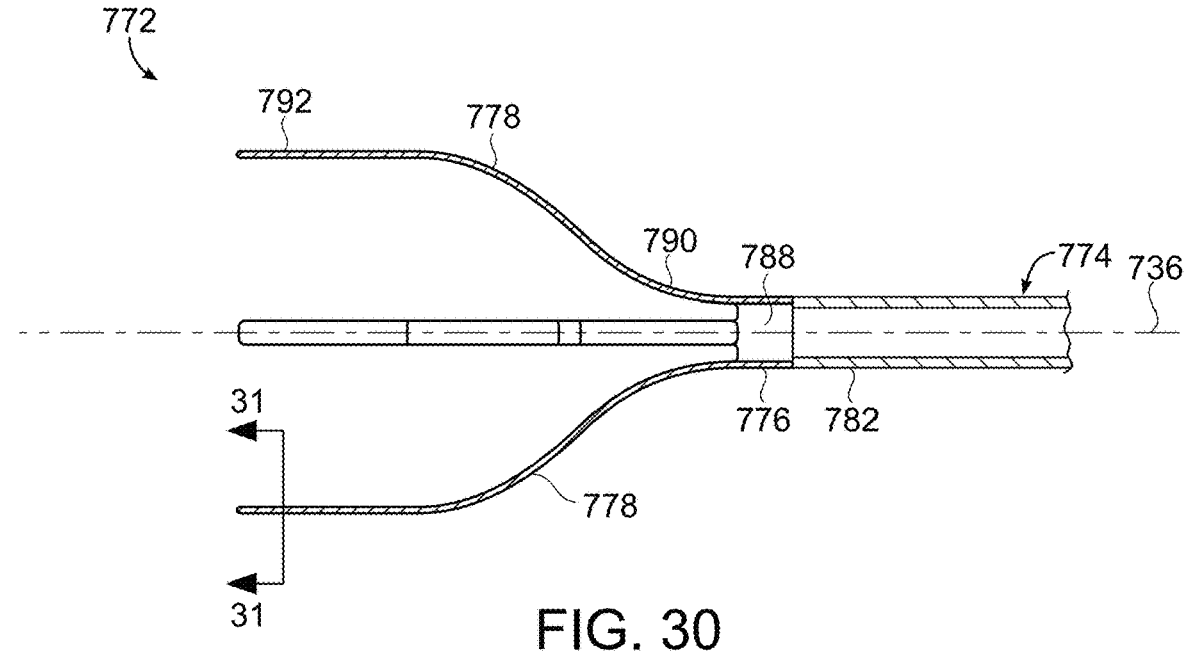
FIG. 30 is a cross-sectional view of one embodiment of a distal end of a torque component of the delivery system that is suitable for delivering an arterial prosthesis radially constrained by a method and system of the invention.

Each arm 778 is expandable from a constricted state, shown in FIG. 29, to an expanded state, shown in FIG. 30, by release of arms 778 from the constricted state of FIG. 29. In one embodiment, arms 778 are self-expanding from the constricted state to the expanded state. Arms 778 are fixed to hub 776 of torque component 772 which, in turn, is fixed to pushrod 774 of torque component 772.

Figure 31:
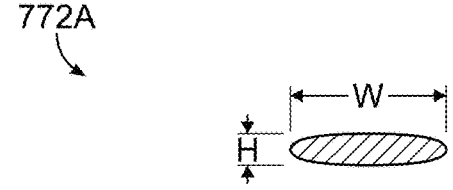
FIG. 31 is a cross-sectional representation of an arm of the torque component shown in FIG. 30 taken along line A-A.

As can be seen in FIG. 31, width (W) of arm 778 is greater than height (H) of arm 778. When viewed at an angle normal to longitudinal axis of hub, as shown in FIG. 30, arms have a curvilinear shape in the expanded state. In various embodiments, torque component 772 can include two, three, or four arms. Arms 778 each have proximal end 790 and distal end 792. Optionally, proximal ends 790 of arms 778 are evenly spaced about longitudinal axis 736 at the circumference of hub 776. In one embodiment, each of arms 778 independently has a length in a range of between about 1 inch and about 5 inches. Hub 776 and arms 778 are formed of a suitable material, such as Nitinol, or other suitable shape-memory alloy, stainless steel, titanium or a plastic.

Figure 32:
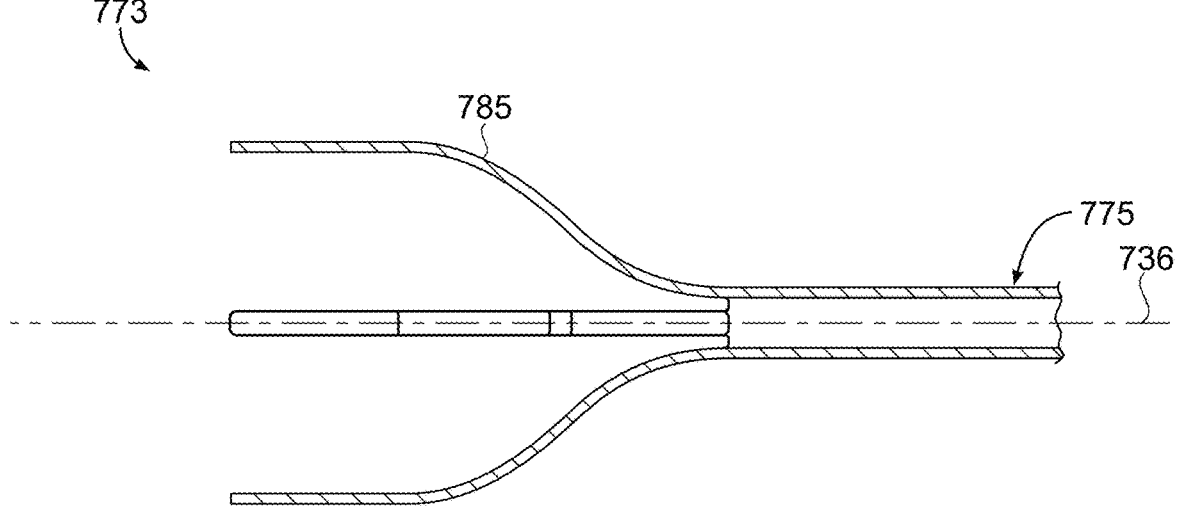
FIG. 32 is a cross-sectional view of another embodiment of a distal end of a torque component of the delivery system suitable for delivering an arterial prosthesis radially constrained by a method and system of the invention.
Figure 33:
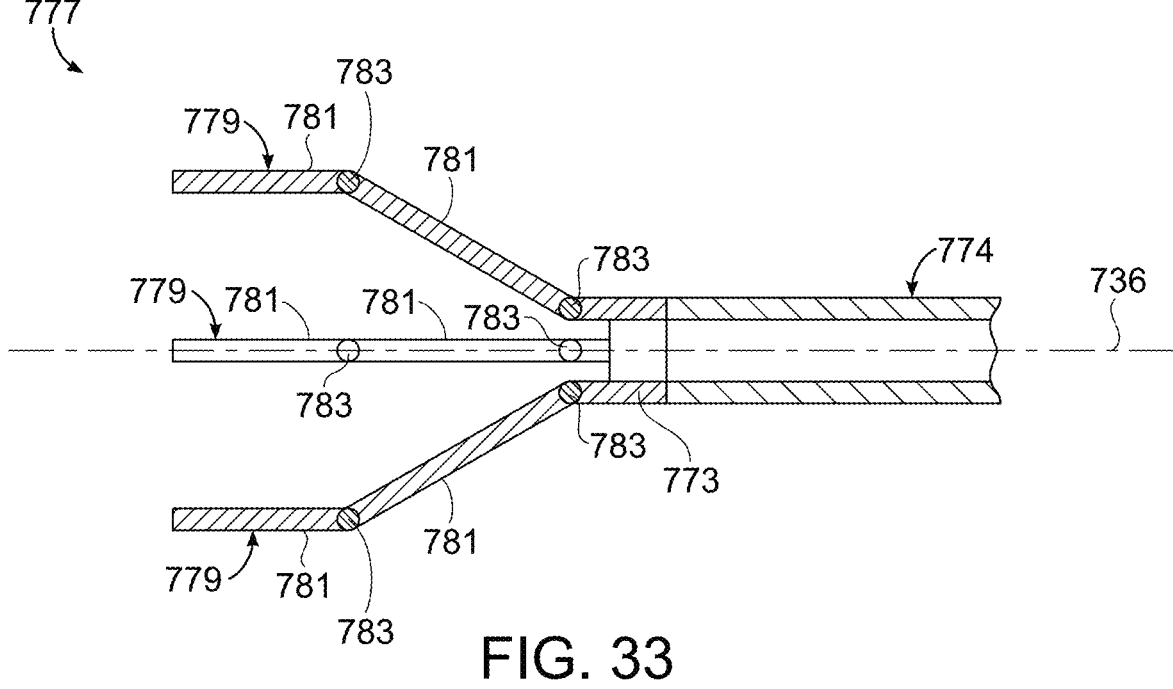
FIG. 33 is a side view of an alternative prior art embodiment of a distal end of torque component suitable for delivering an arterial prosthesis radially constrained by a method and system of the invention wherein arms of the torque component are articulated.

FIG. 32 is a cross-sectional view of another embodiment of the torque component of FIG. 30, but wherein the torque component lacks a hub component. As shown therein, torque component 773 includes arms 785 connected to pushrod 775, or extensions of pushrod 775. Alternatively, torque component 777 includes arms that are articulated members 779, as shown in FIG. 33. In this embodiment, members 779 include segments 781 joined to each other and to pushrod 775 by hinges 783. Members 779 are formed of a suitable material, such as Nitinol or some other shape-memory alloy, stainless steel, titanium, or a plastic.

Figure 34:
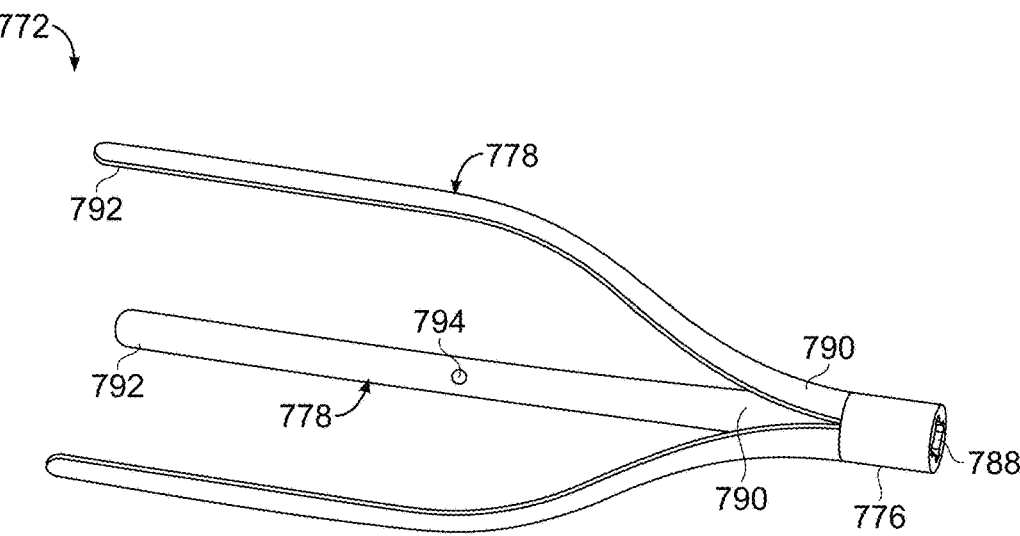
FIG. 34 is a perspective view of another prior art embodiment of a torque component suitable for use with an embodiment of the invention, wherein an arm of the torque component defines an opening.
Figure 35:
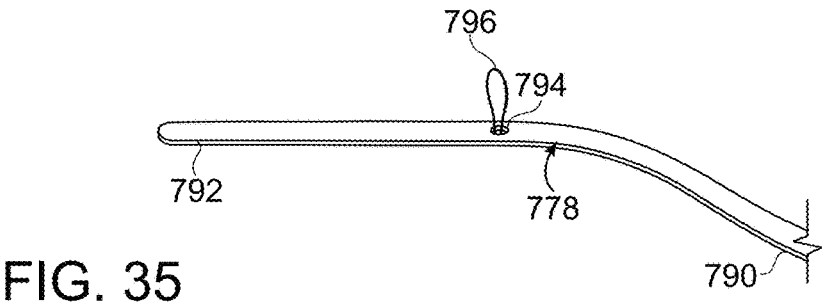
FIG. 35 is a perspective view of an arm of the torque component shown in FIG. 32, wherein a suture ring extends from the opening.
Figure 36:
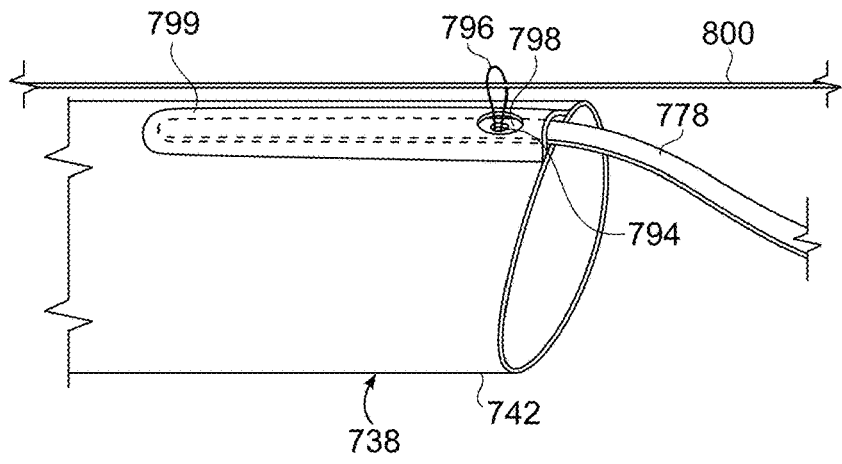
FIG. 36 is a side view of another view of the embodiment of the arm and suture ring shown in FIG. 35, wherein the arm extends into a pocket at the distal end of the stent graft, and the suture ring, which is secured to a prong of torque component, extends from the prong and through an opening defined by the pocket at the distal end of the stent graft, and a release wire extends through the suture ring, according to one embodiment of the invention.
Figure 41:
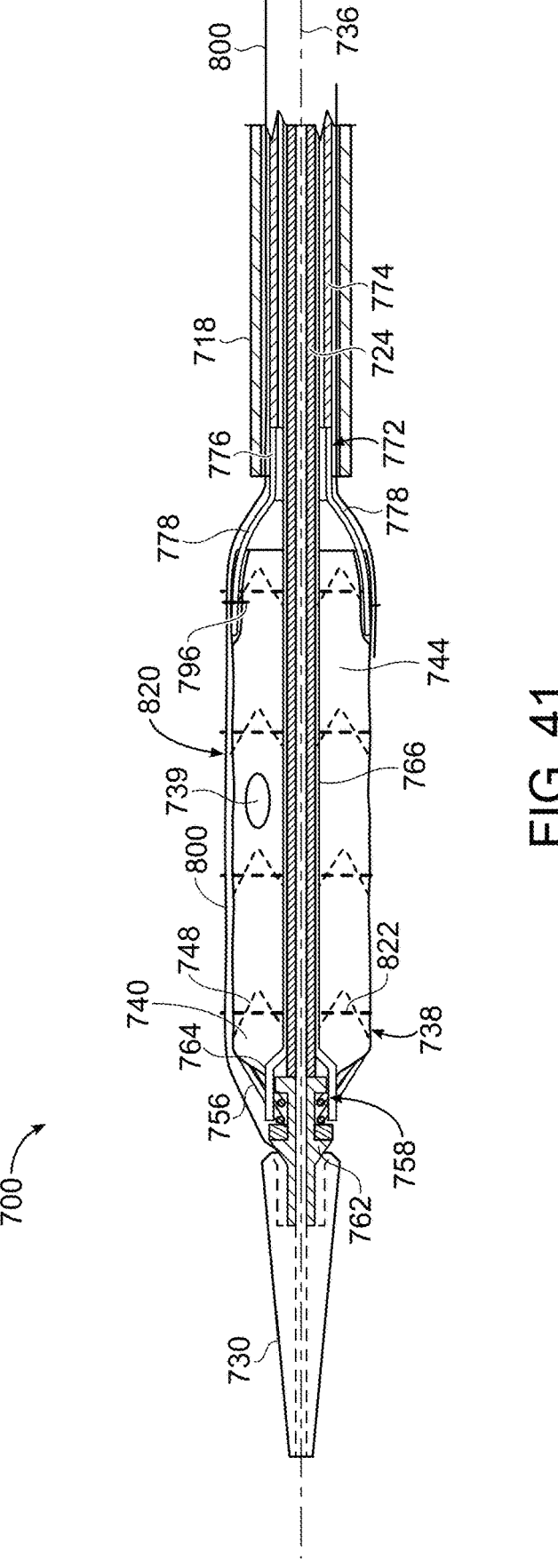
FIG. 41 is a cross-section of an embodiment of the delivery system shown in FIG. 40, wherein the introducer sheath has been fully retracted from the stent graft and also from arms of the torque component of the delivery system of the invention.
Figure 42:
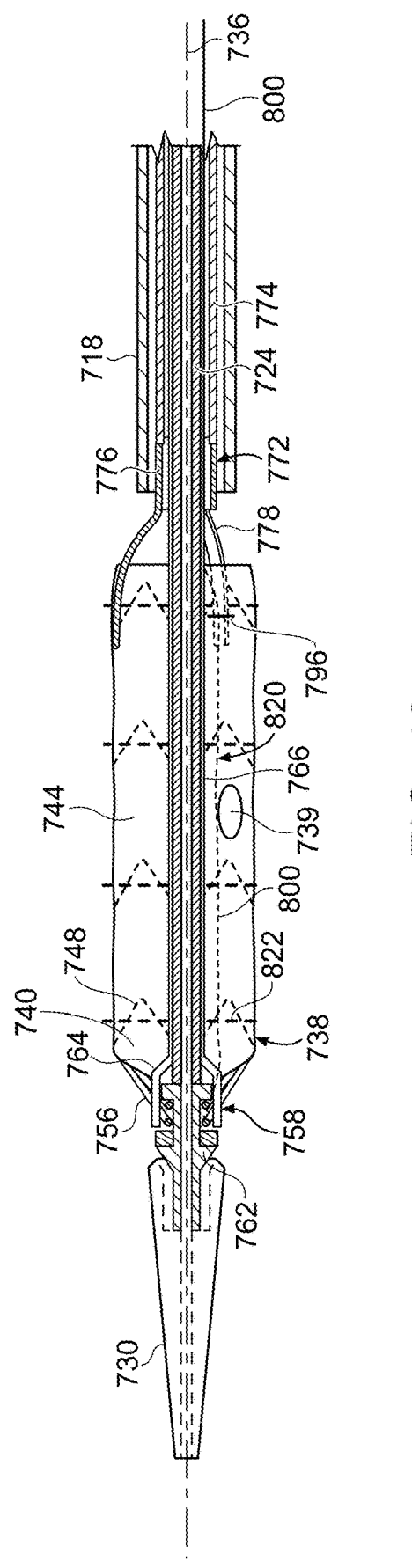
FIG. 42 is a cross-sectional view of the delivery system of the invention shown in FIG. 41, wherein the stent graft has been rotated about the guidewire catheter.

In another embodiment, shown in FIGS. 34-36, torque component 772 includes at least one arm 778 defines opening 794 through which suture ring 796 extends and to which suture ring 796 is fixed. Suture ring 796 also extends through opening 798 defined by stent graft 738. Release wire 800 extends longitudinally along delivery device 700 is tucked into, or under, nose cone 730, as shown in FIG. 29, and through suture ring 796 extends, as shown in FIG. 36, thereby securing distal end 742 of stent graft 738 to arm 778. An advantage of wire 800 (FIG. 36) extending through suture loop 796 is gained when guidewire catheter 724 and apex capture assembly 758, to which stent graft 738 is held in a captured state, has been exposed by retraction of introducer sheath 718 and, as shown in FIG. 41, is moved longitudinally within artery along longitudinal axis 736 in order to properly position stent graft 738. Referring back to FIGS. 34-36, suture 796 is held in place at opening 798, which is defined by pocket, or sleeve, 799 of stent graft 738, by wire 800 extending through suture 796, thereby preventing longitudinal collapse of stent graft 738 that would otherwise occur by friction between stent graft 738 and an arterial wall during longitudinal positioning that includes proximal movement (toward the clinician) of guidewire catheter 724 and apex capture assembly 758 (FIG. 41).

Figure 37:
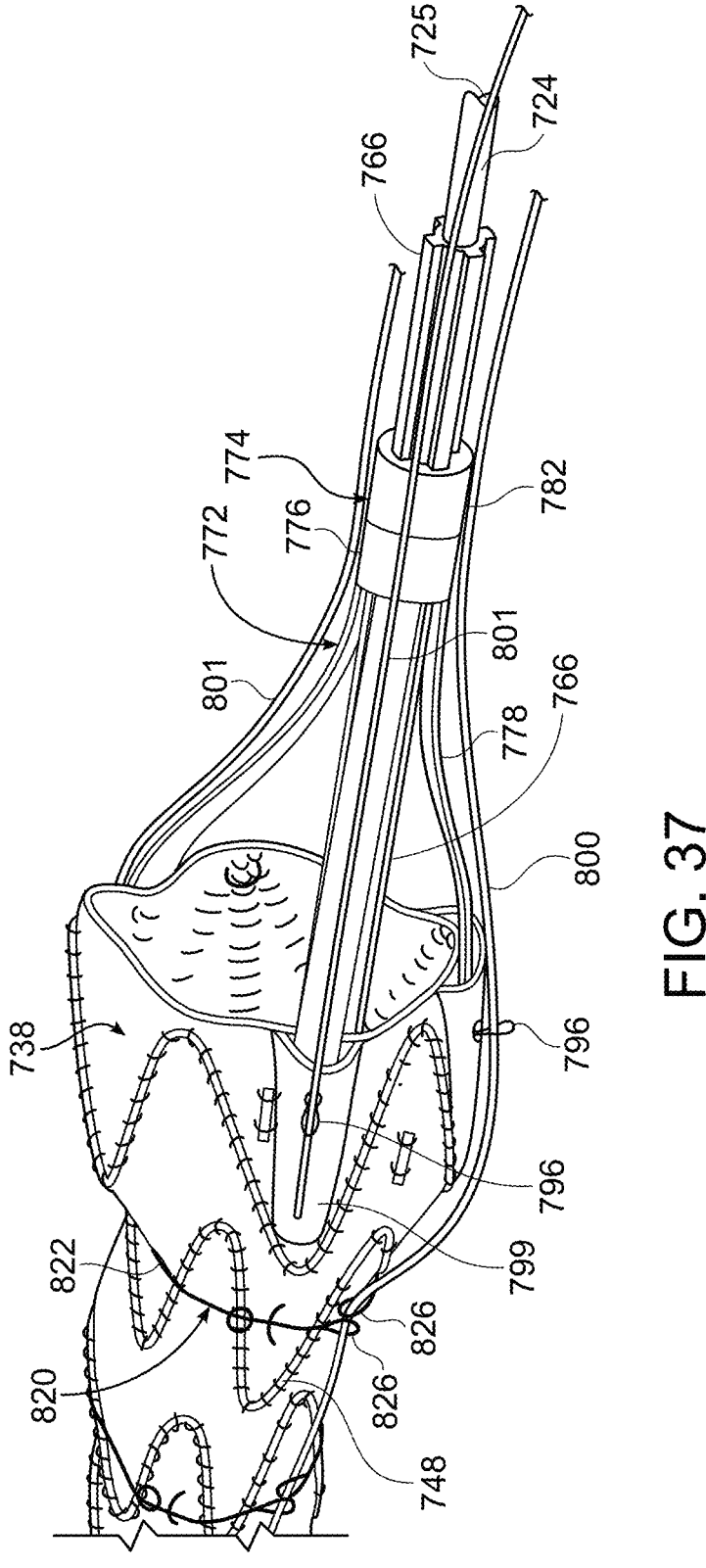
FIG. 37 is a three-dimensional representation of the torque component shown in FIG. 34 in combination with the distal end of a stent graft, wherein the stent graft is radially constrained according to an embodiment of the system of the invention.

As can be seen in FIG. 37, radial constraint 820 radially constrains stent graft 738. In one embodiment, radial constraint 820 includes ligatures 822, or threads, that span each of stents 748 of stent graft 738. Wire 800, extends through a loop 826 of each ligature 822, whereby retraction of wire 800 from ligatures 822 releases stent graft 738 from radial constraint 820. Pushrod 774 defines keyed outer extrusion portion, through which apex capture catheter 766 and guidewire catheter 724 extend. As can be seen in FIG. 37, apex capture catheter 766 defines inner extrusion component that is keyed to and is longitudinally moveable relative to outer extrusion portion of pushrod 774. Guidewire catheter 724 defines guidewire lumen 725 and extends through and is longitudinally moveable relative to apex capture catheter 766. Wires 801 extend through suture rings 796 at sleeve 799. Wire 800 also extends through suture rings 796, as shown in FIGS. 35-37, 41-43, and 54-57, but also is a trigger wire extending through loops 826, and releases loops 826 upon withdrawal of wire 800 for release of the stent graft from a radially constricted position.

Figure 38:
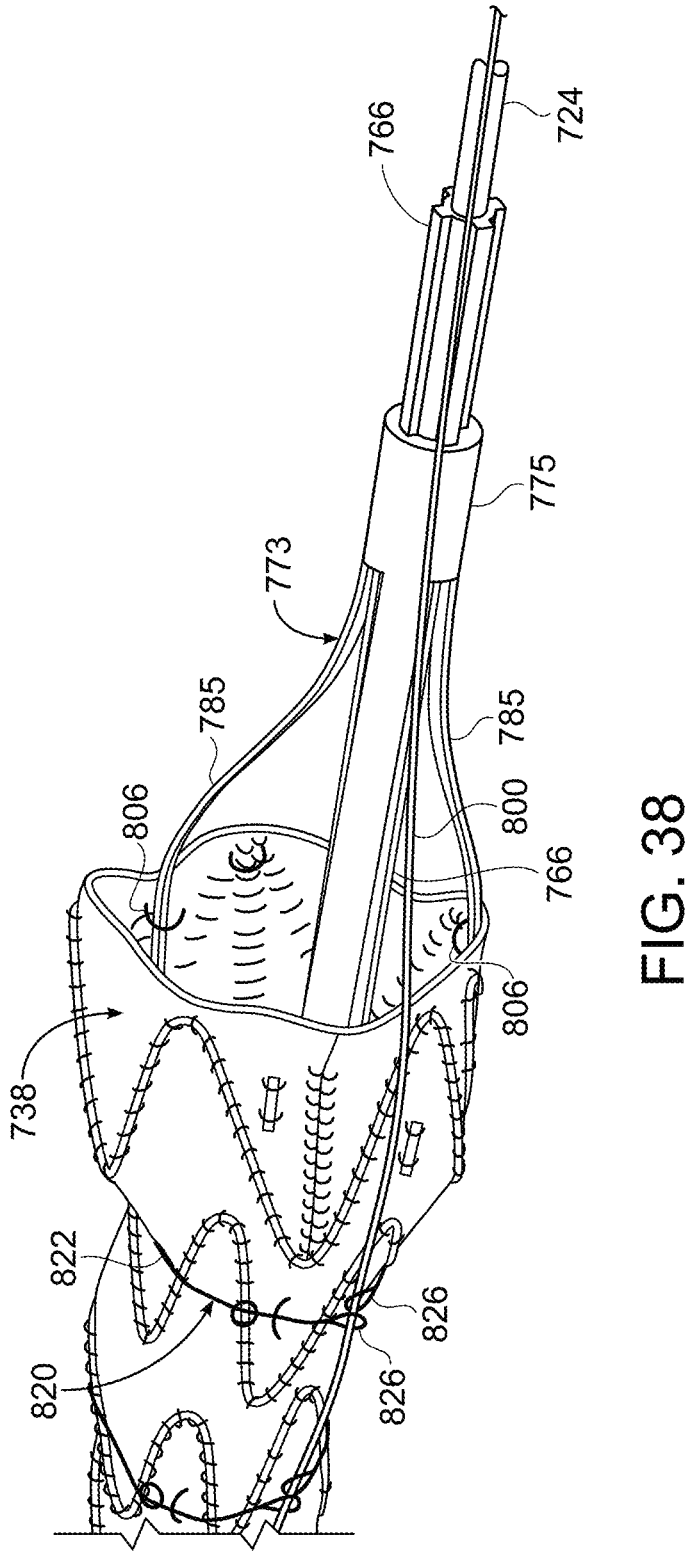
FIG. 38 is a three-dimensional representation of the torque component shown in FIG. 34, in combination with a distal end of a stent graft that radially constrained according to another embodiment of the system of the invention.

In an alternative embodiment, shown in FIG. 38, torque component 772 does not include hub 776. In this embodiment, arms 778 can be fixed directly to distal end 782 of pushrod 774 or can be fabricated by selective machining or cutting of a distal end of a rod to form arms 785 and pushrod 775. In still another embodiment (not shown), wire 800 is located on the interior of stent graft 738 and extends through suture 806 that extends through an opening of each arm to the interior of the stent graft. As indicated from FIG. 36, in one embodiment, retraction of wire 800 will also release stent graft 738 from arms 785 of torque component 772.

Figure 39:
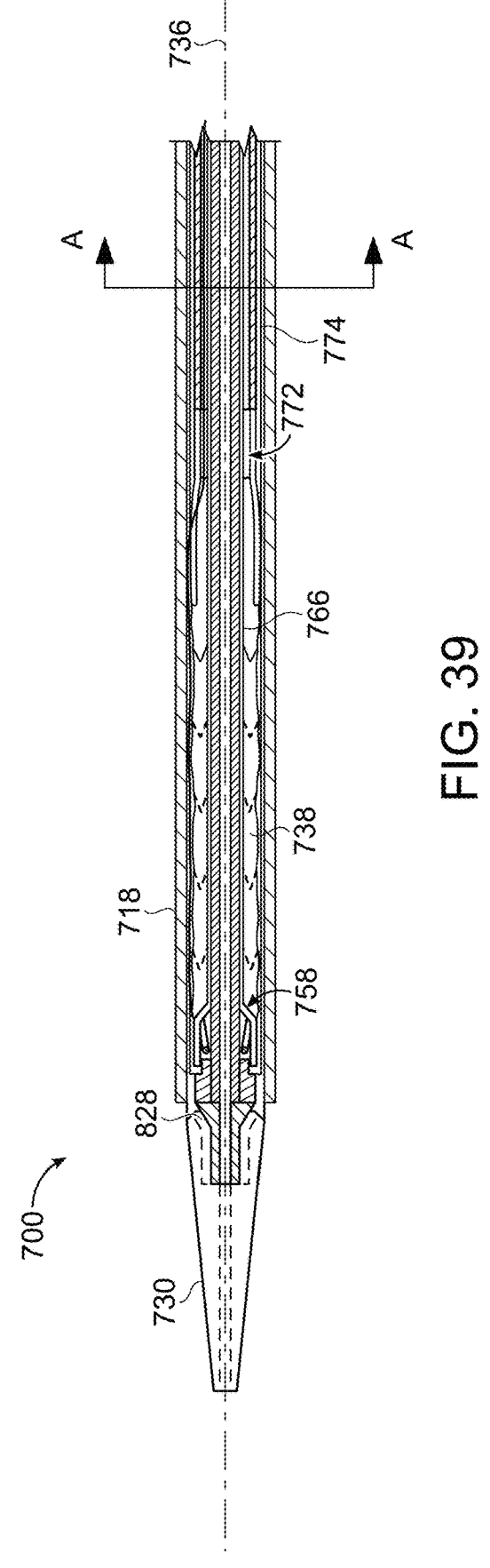
FIG. 39 is a cross-sectional representation of a delivery system of the invention, including a flexible sheath extending about the stent graft and within an introducer sheath.
Figure 39A:
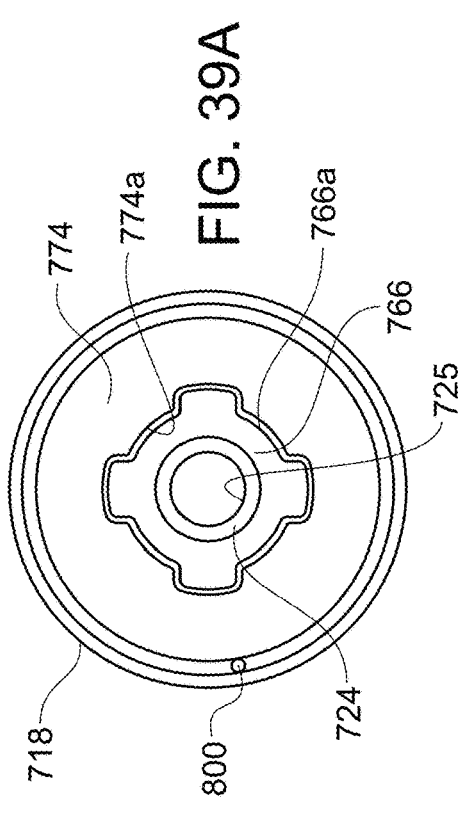
FIG. 39A is cross-section of the embodiment shown in FIG. 39 taken along line AA, showing the configuration of keyed inner and outer extrusion components of the torque component.

Alternatively, the radial constraint is flexible sheath 828 that extends between stent graft 738, and introducer sheath 718, and is tucked into, or under, nose cone 730, as shown in FIG. 39. FIG. 39A is a cross-section taken along line A-A of FIG. 39. As can be seen in FIG. 39A, introducer sheath 718 longitudinally surrounds pushrod 774. Pushrod 774 defines an outer keyed extrusion 774a. Apex capture catheter 766 is within pushrod 774 and defines an inner keyed extrusion 766a. Apex capture catheter 766 also defines a lumen through which guidewire catheter 724 extends and is longitudinally moveable. Wire 800 extends between introducer sheath 718 and pushrod 774. Guidewire catheter 724 defines guidewire lumen 725 through which a guidewire (not shown), can extend.

In one embodiment of a method of the invention, stent graft 738, which is in the first constrained state, as shown in FIG. 38, is directed to an aneurysm site of a subject. Introducer sheath 718 is then retracted by rotation of lead screw nut 732 about track 734 of handle body 712, as shown in FIG. 28, Option I, whereby abutment of lead screw nut 732 against distal handle 716 causes track 734 and introducer sheath 718, to which track 734 is attached, to move in proximal direction 702 relative to the surgeon. Alternatively, or subsequently, lead screw nut 732 can be pulled in proximal direction 702 by the surgeon, as shown in Option II of FIG. 28, to retract introducer sheath 718 in proximal direction 702 relative to guidewire catheter 724 and stent graft 738.

Figure 40:
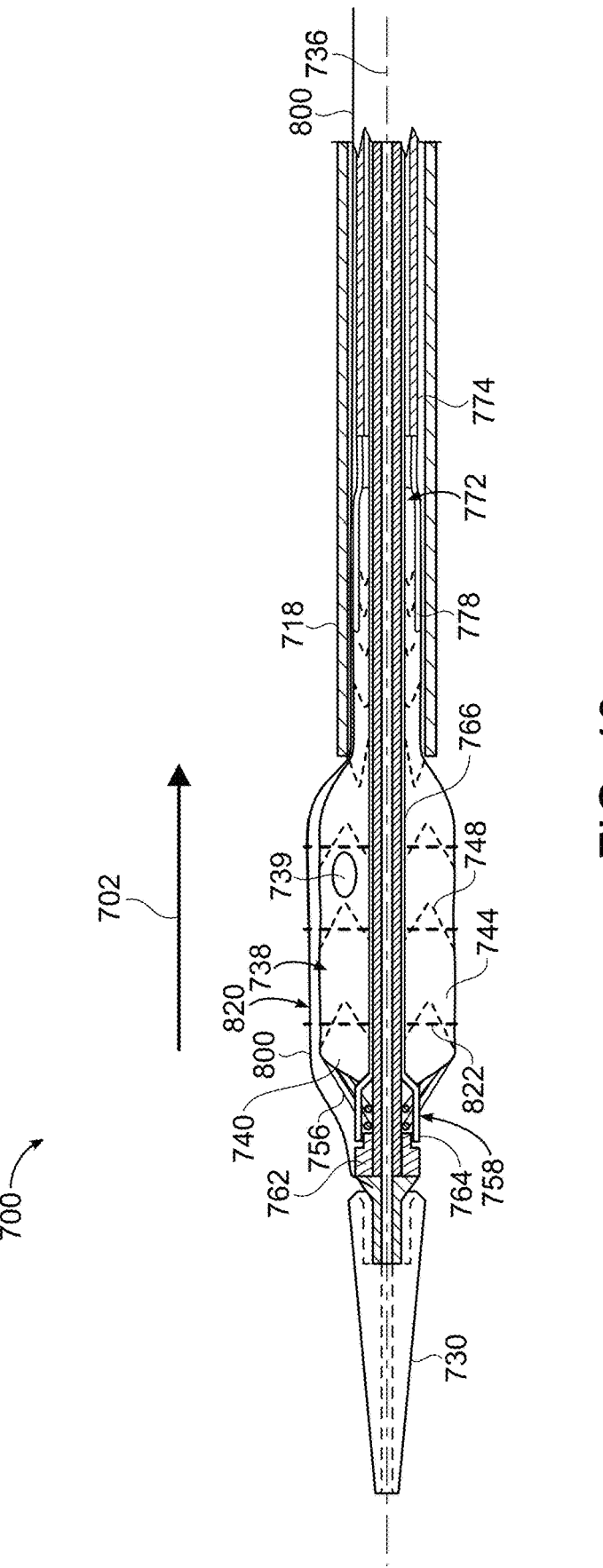
FIG. 40 is a cross-sectional view of the delivery system of the invention shown in FIG. 39, wherein the introducer sheath has been partially retracted from the stent graft.

As can be seen from FIG. 40, at least partial retraction of introducer sheath 718 in proximal direction 702 causes proximal end 740 of stent graft 738 to shift from a first constrained position, represented in FIG. 39 to a second constrained position, which is maintained by radial constraint 820. As shown in FIG. 41, fully retracting introducer sheath 718 from stent graft 738 and from torque component 772 causes stent graft 738 to assume the second constrained position along its entire length. The second constrained position is maintained by radial constraint 820. Also, shifting from the first constrained position to the second constrained position causes torque component 772 to radially expand from a first constrained position, shown in FIG. 39, to a second constrained position, is also referred to as an intermediate radially-expanded position, shown in FIG. 41. Application of torque force to torque component 772, while the introducer sheath 718 is at least partially retracted, causes stent graft 738 to rotate about longitudinal axis 736.

For example, when stent graft 738 is in the second constrained position, shown in FIG. 41, torque component 772 can be rotated about guidewire catheter 724 by rotating proximal handle 714 (FIG. 28), which rotates pushrod 774 (FIG. 42), to which it is connected. This rotation of torque component 772 enables rotational alignment of at least one fenestration 739 of stent graft 738, as shown in the transition from FIG. 41 to FIG. 42. Stent graft 738 can also be moved longitudinally along longitudinal axis 736 (also referred to as axial movement) to properly position stent graft 738 at an aneurysm site. As noted above, suture 796, extending through arm 778, luminal graft component 744, and through which wire 800 extends, fixes distal end 742 of stent graft 738 to delivery system 710, thereby substantially preventing longitudinal collapse of stent graft 738 by friction between distal end 742 of stent graft 738 and an arterial wall during proximal movement (toward the clinician) of apex capture assembly 758, to which proximal end 740 is held in the captured state shown in FIG. 42.

Figure 43:
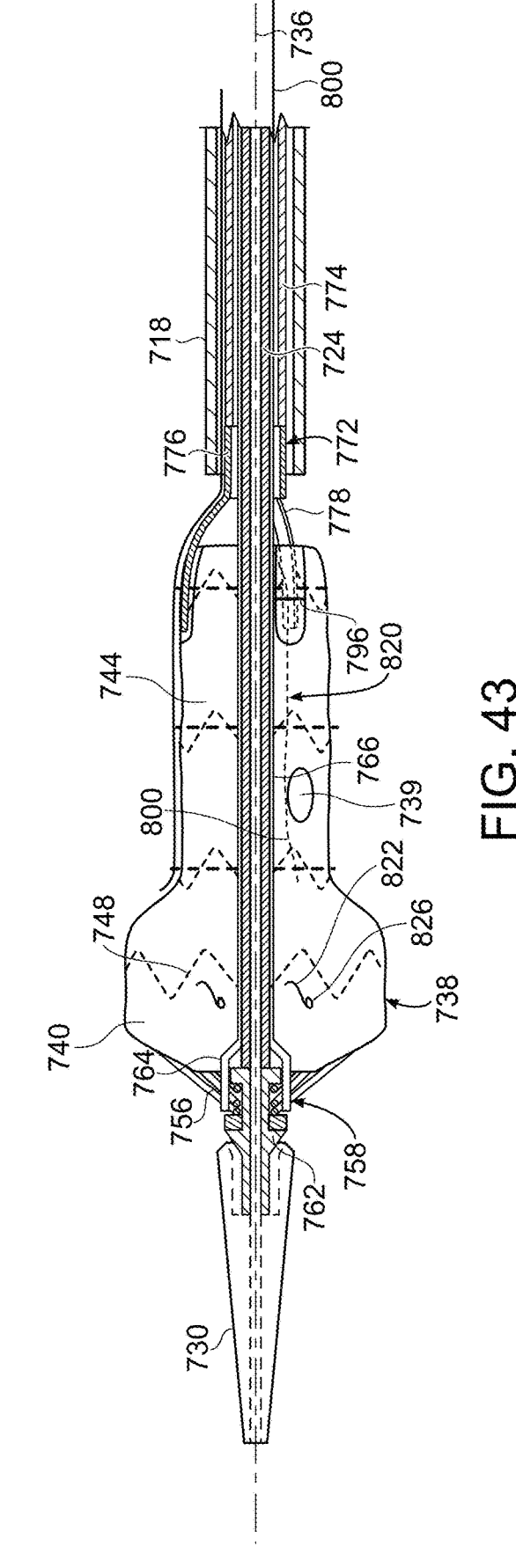
FIG. 43 is a cross-sectional view of the delivery system of the invention shown in FIG. 42, wherein a wire extending through a suture and radially constraining a stent graft has been partially retracted from the sutures to partially release the stent graft.
Figure 44:
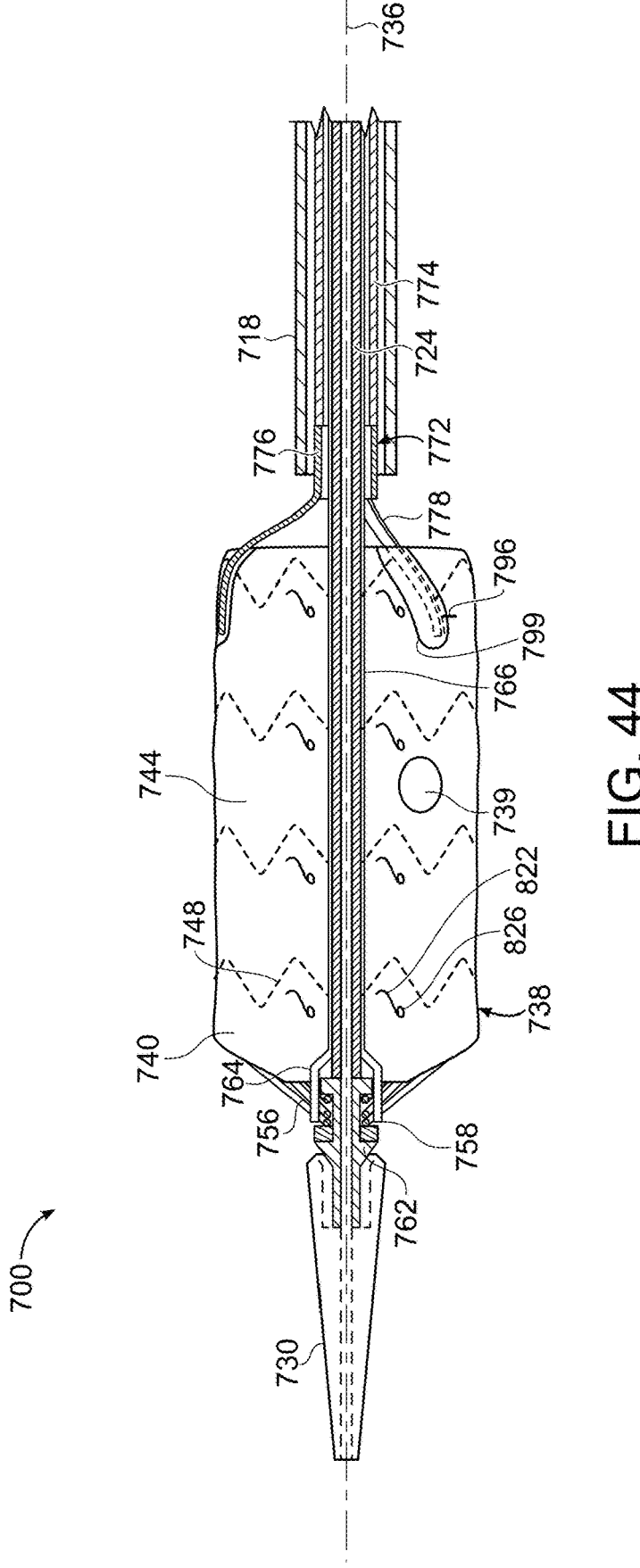
FIG. 44 is a cross-sectional view of the delivery system of the invention and stent graft shown in FIG. 43, wherein the wire radially constraining the stent graft has been completely retracted from the sutures, thereby fully releasing the stent graft.
Figure 45:
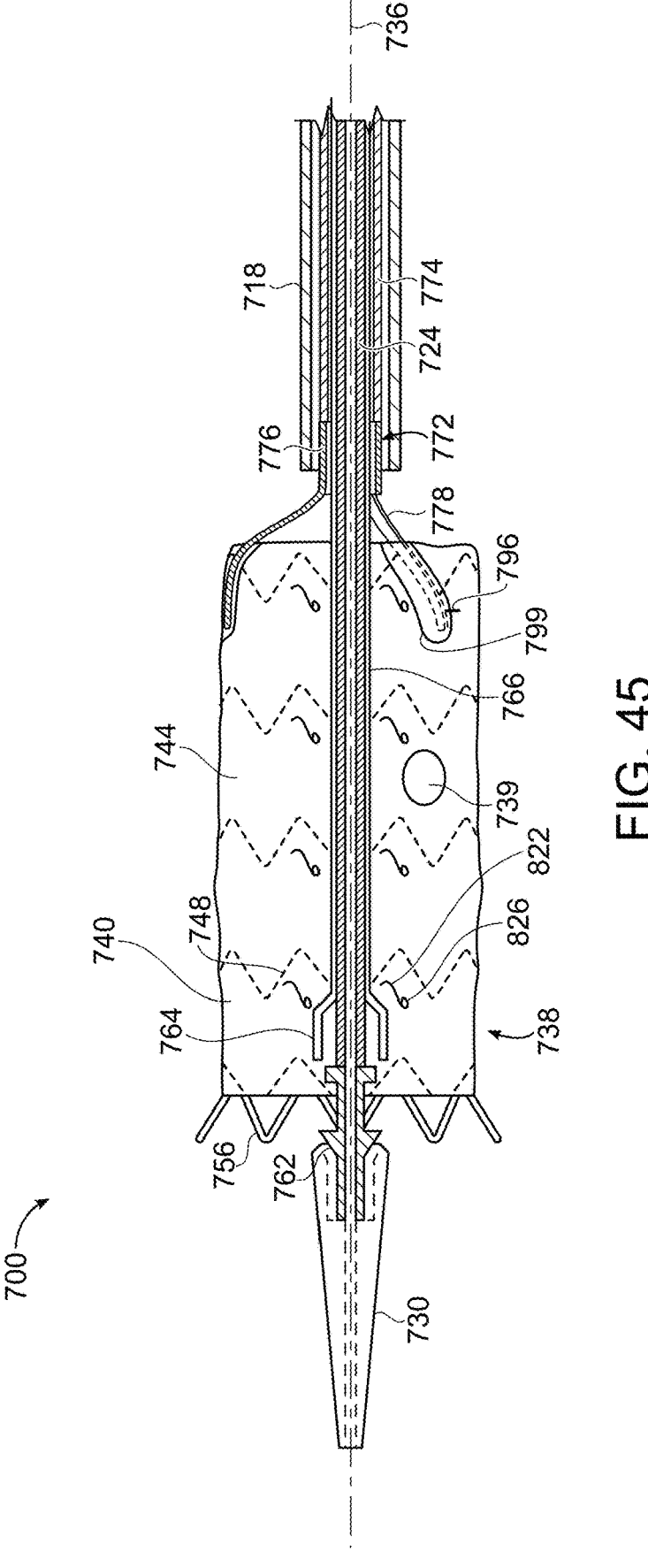
FIG. 45 is a cross-sectional view of the delivery system of the invention of the stent graft shown in FIG. 44, wherein an apex clasp component of the delivery system has been opened to release proximal apices of a proximal bare stent of the stent graft.
Figure 46:
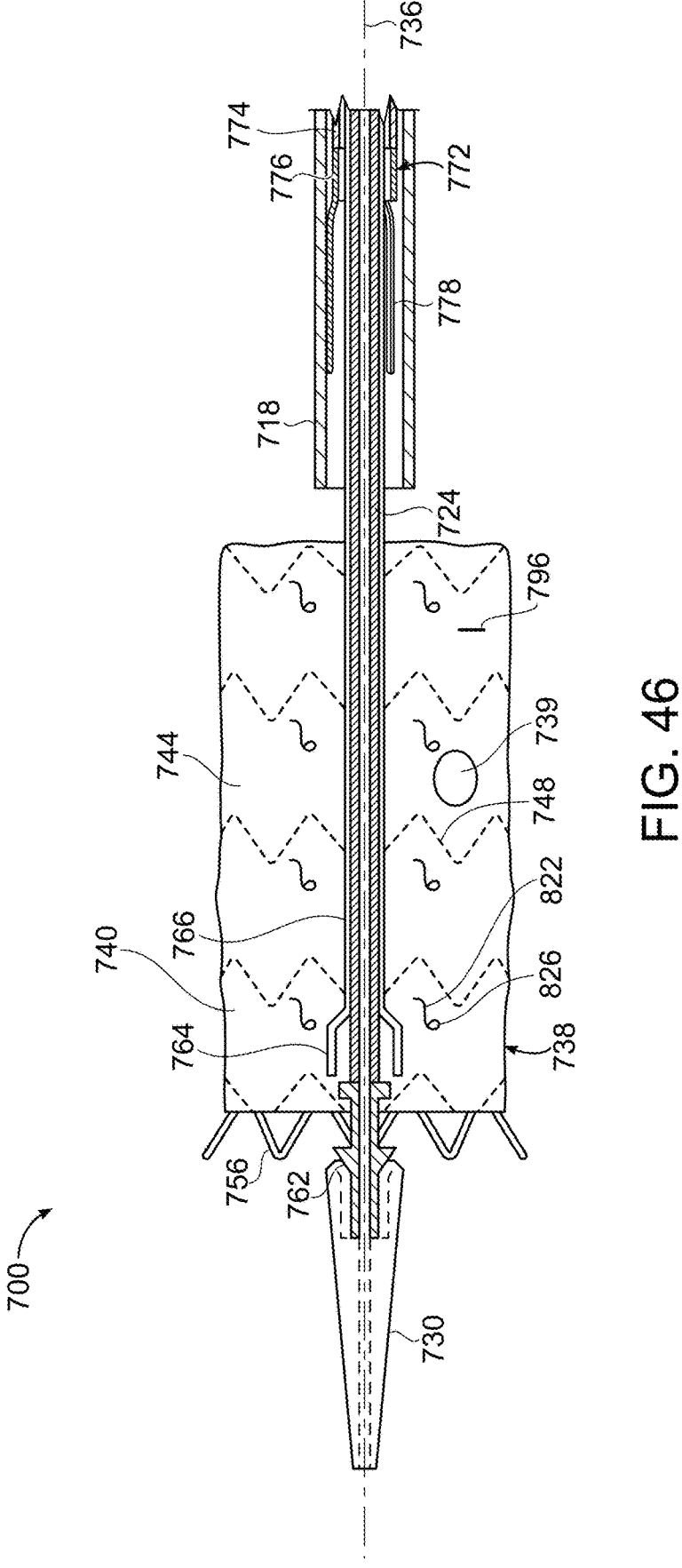
FIG. 46 is a cross-sectional view of the delivery system of the invention of the stent graft shown in FIG. 45, wherein the distal torque component has been retracted from the partially deployed stent graft and into an introducer sheath of the delivery system, thereby fully deploying the stent graft.
Figure 47:
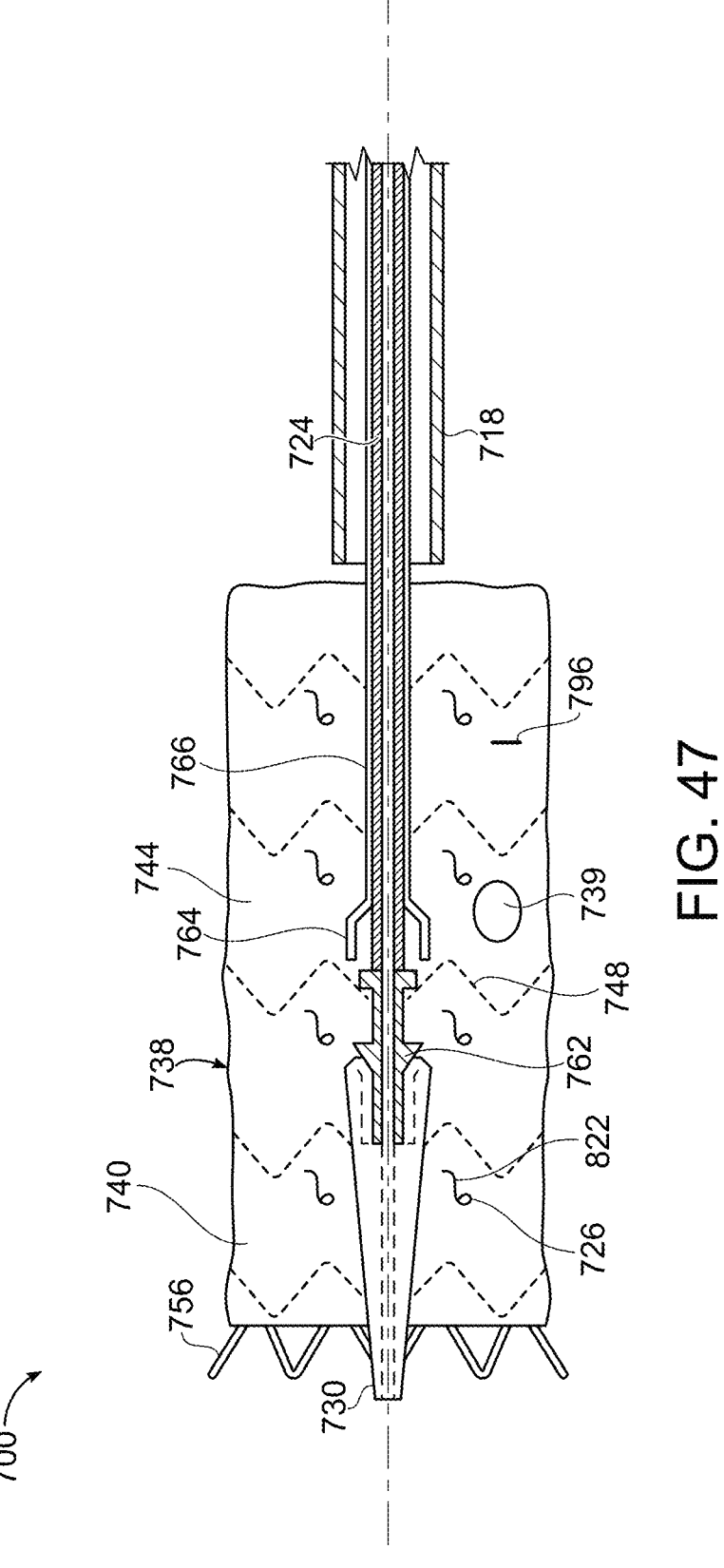
FIG. 47 is a cross-sectional view of the delivery system of FIG. 46, wherein the delivery system has been partially retracted from the fully deployed stent graft.

In the embodiment shown in FIG. 43, wire 800 of radial constraint 820 is retracted from ligatures 822, thereby releasing ligatures 822 of radial constraint 820 and allowing the remainder of stents 738 to fully expand in a radial direction, as shown in FIG. 44. This allows stents 738 to land at their proper locations within an aorta and without distortion of stent graft 738 or damage to the surgical site. Thereafter, apex capture assembly 758 is actuated by releasing apex capture catheter 766 from guidewire catheter 724 at proximal clasp assembly 768 (FIGS. 27 and 28), and retracting proximal apex capture component 764 and apex capture catheter 766, as shown in FIG. 45, to which proximal apex capture component 764 is fixed, thereby releasing bare stent 756 from its captured state, shown in FIG. 44, to a released state, shown in FIG. 45. As a consequence of release, proximal end 740 of stent graft 738 will land at its designated location at the surgical site Torque component 772 is then retracted from distal end 742 of stent graft 738, as shown in the transition from FIG. 45 to FIG. 46, thereby fully releasing and deploying stent graft 738. As shown in FIG. 47, guidewire catheter 724 and apex capture catheter 766 can then be retracted from stent graft 738, and delivery device 710 can be removed from the subject, thereby completing the procedure. As stated above, the introducer sheath and hemostasis valve can be left in place in order to facilitate additional prosthetic components, such as a branch stent graft through fenestration 739 into a branch blood vessel.

It is to be understood that other delivery devices can be deployed to conduct the method of the invention. For example, stent graft 738 can be directed to an aneurysm site without the aid of an introducer sheath 718. In one such embodiment, stent graft 738 is implanted in a subject while being constrained only by radial constraint 820, without constraint by introducer sheath 718. In another embodiment, the method includes first directing stent graft 738, while it is in a first constrained state and within introducer sheath 718, to a position distal to an aneurysm site, followed by advancement of the stent graft from the distal end 722 of the introducer sheath 718 to the aneurysm site.

Figures 48, 49A, 49B, 49C:
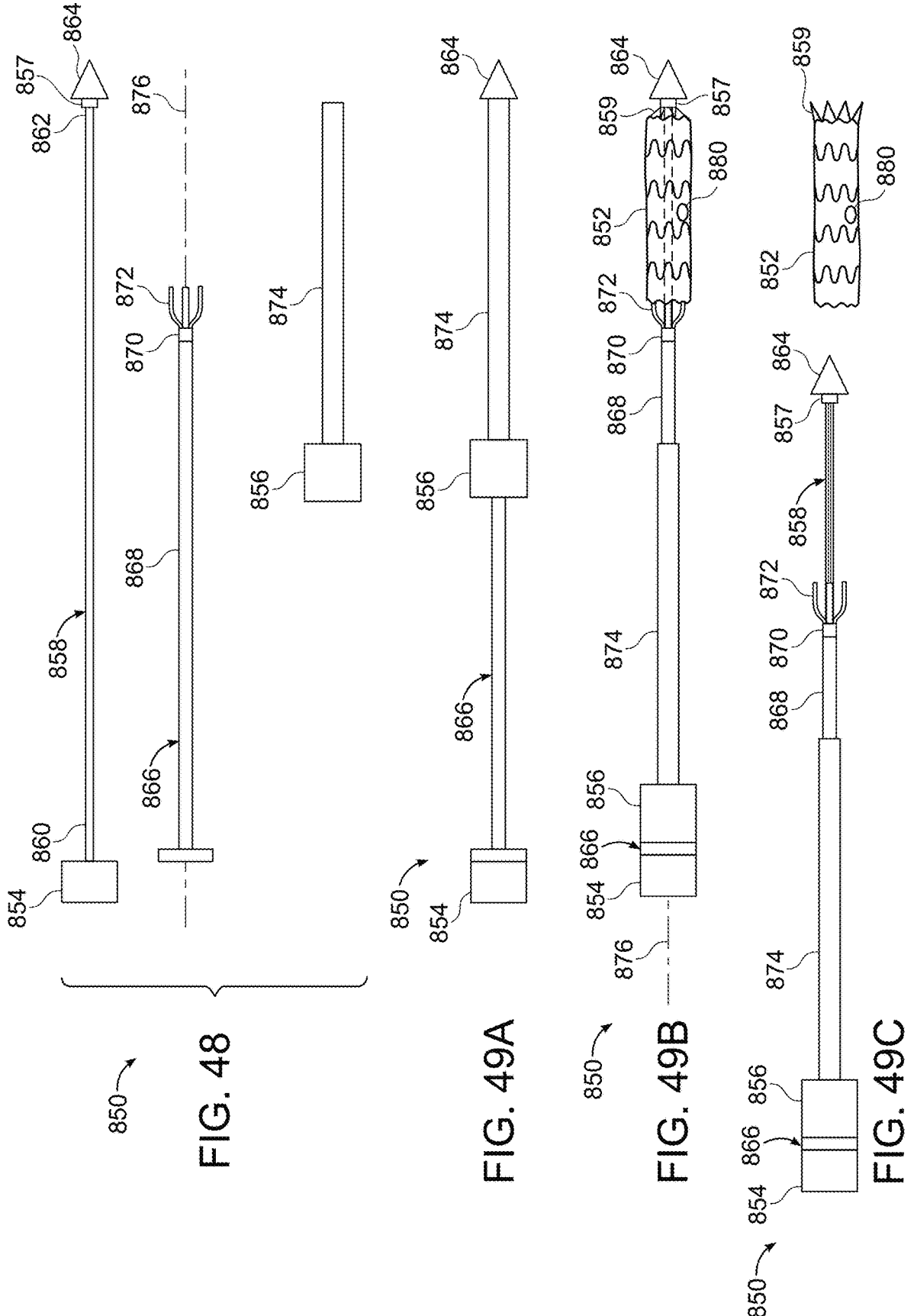
FIG. 48 is an exploded view of another embodiment of a delivery system of the invention.
FIG. 49A is a side view of the embodiment of the delivery system shown in FIG. 48, in an assembled state, prior to deployment of a radially-constrained stent graft.
FIG. 49B is a side view of the delivery system of FIGS. 48 and 47A, following retraction of radial constraint from the stent graft.
FIG. 49C is a side view of the delivery system of FIGS. 48, 49A, and 49B, following release of a torque component from a distal end of the stent graft, and removal of the delivery system from the stent graft, thereby implanting the stent graft.

In another embodiment, the radial constraint is the introducer sheath. For example, as shown in FIG. 48 as an exploded view, delivery system 850 of the invention for implanting a stent graft 852 (FIGS. 49A-49C) includes proximal handle 854 and distal handle 856. Guidewire catheter 858 includes a proximal end 860 and distal end 862, and extends distally from distal handle 854. Nose cone 864 and apex capture device 857 are fixed at distal end 862 of guidewire catheter 858. Torque component 866 includes pushrod 868, and at least two arms 872, which can be self-expanding, extending from pushrod. Optionally, hub 870 is included as a link between pushrod 868 and arms 872. Hub 870 defines a lumen about longitudinal axis 876 and is fixed to pushrod 868. Arms 872 are disposed radially about hub 870 and extend distally from hub 870. The radial constraint, in this embodiment, is introducer sheath 874, which extends distally from distal handle 856.

FIG. 49A is an assembled view of delivery system 850 shown in FIG. 48. As can be seen in FIGS. 49A through 49C, each arm 872 is movable from a constrained state to an expanded state. In one embodiment, arms 872 of torque component 866 exhibit radial self-expansion away from longitudinal axis 876. Introducer sheath 874 extends longitudinally between distal handle 856 and distal end 862 of guidewire catheter 858 and radially constrains stent graft 852 extending distally from torque component 866 and about guidewire catheter 858. Application of torque force to arms 872 by rotation of torque component 866 about longitudinal axis 876 causes fenestration 880 of stent graft 852 to rotate about longitudinal axis 876 until it is rotationally aligned a branch blood vessel at the aneurysm site. In a method of the invention, advancement of the stent graft 852 within introducer sheath 874 to an aneurysm site is followed by rotational alignment of at least one fenestration 880. Rotation of introducer sheath 874 can be independent of any rotation of guidewire catheter 858 or proximal handle 854. Alternatively, introducer sheath 874 can be in conjunction with rotation of guidewire catheter 858, such as by locking torque component 866 to proximal handle 854. As shown in FIG. 49B, stent graft 852 is releasably secured to distal end 862 of guidewire catheter 858 at bare stent 859 by a suitable apex capture device 857, such as is known in the art. Bare stent 859 is released from guidewire catheter 858 by actuation of the apex capture device 857. Retraction of radial constraint 866 from stent graft 852 causes radial expansion of self-expanding arms 872 and self-expansion of stent graft 852 to thereby release stent graft 852, and the remainder of delivery system 850 not implanted at the aneurysm is then retracted from stent graft 852 and from the aneurysm site as shown in FIG. 49C.

Figures 50A, 50B, 50C:
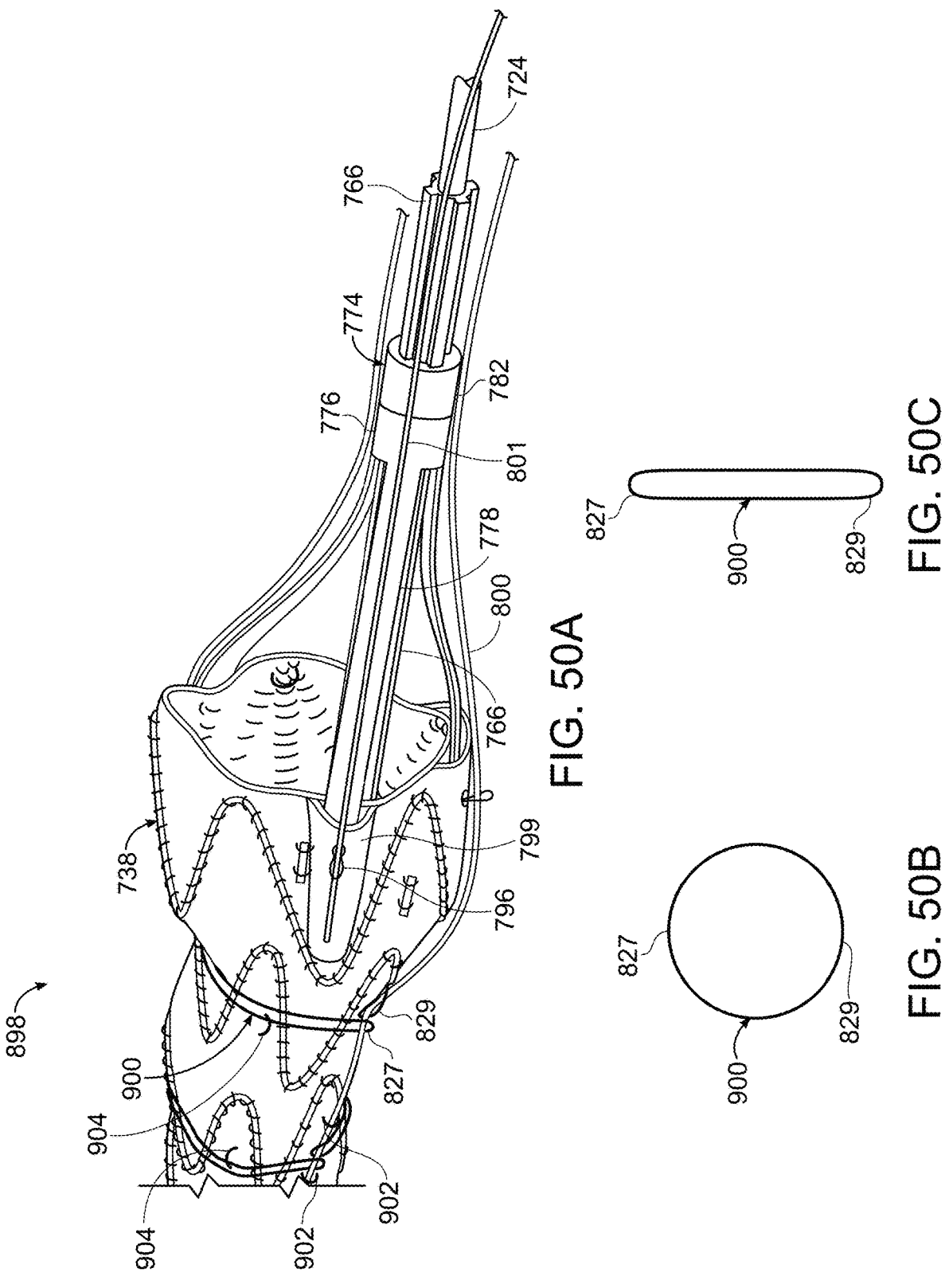
FIG. 50A is a perspective view of another embodiment of the invention, wherein a wire links opposite ends of a collapsed suture wrap, or circular ligature, and the suture wrap passes through loops at struts of stents of a stent graft according to an embodiment of the invention.
FIG. 50B is a detail of the circular ligature shown in FIG. 50A.
FIG. 50C is a detail of the circular ligature of FIGS. 50A and 50B when diametrically opposed ends of the circular ligature are arranged to be linked by a wire to secure the circular ligature and thereby radially-constrain the stent graft.

In another embodiment, shown in FIG. 50A, stent graft delivery system 898, which is an alternate embodiment from that shown in FIG. 37, includes circular ligatures 900 extending about the periphery of stent graft 738 to form diametrically opposed ends 827,829 of circular ligatures 900 that are linked by wire 800. Wire 800 is stabilized by anchor loops 902. Upon retraction of wire 800, circular ligature is secured to luminal graft component by sutures 904. Wire 801 is stabilized at prong 778 by suture loop 796 extending from prong 778 through sleeve 799 of stent graft 738. FIG. 50B is a detail of the circular ligature 900 shown in FIG. 50A, configured as a circle when not wrapped about stent graft 728. FIG. 50C is a detail of circular ligature 900 when configured to be wrapped about stent graft 728. As can be seen from FIGS. 50A-50C, diametrically opposed ends 827,829 of circular ligature 900 secure circular ligature 900 about stent graft 728 when they are linked by wire 800.

Figures 51, 52A, 52B, 52C, 52D, 52E:
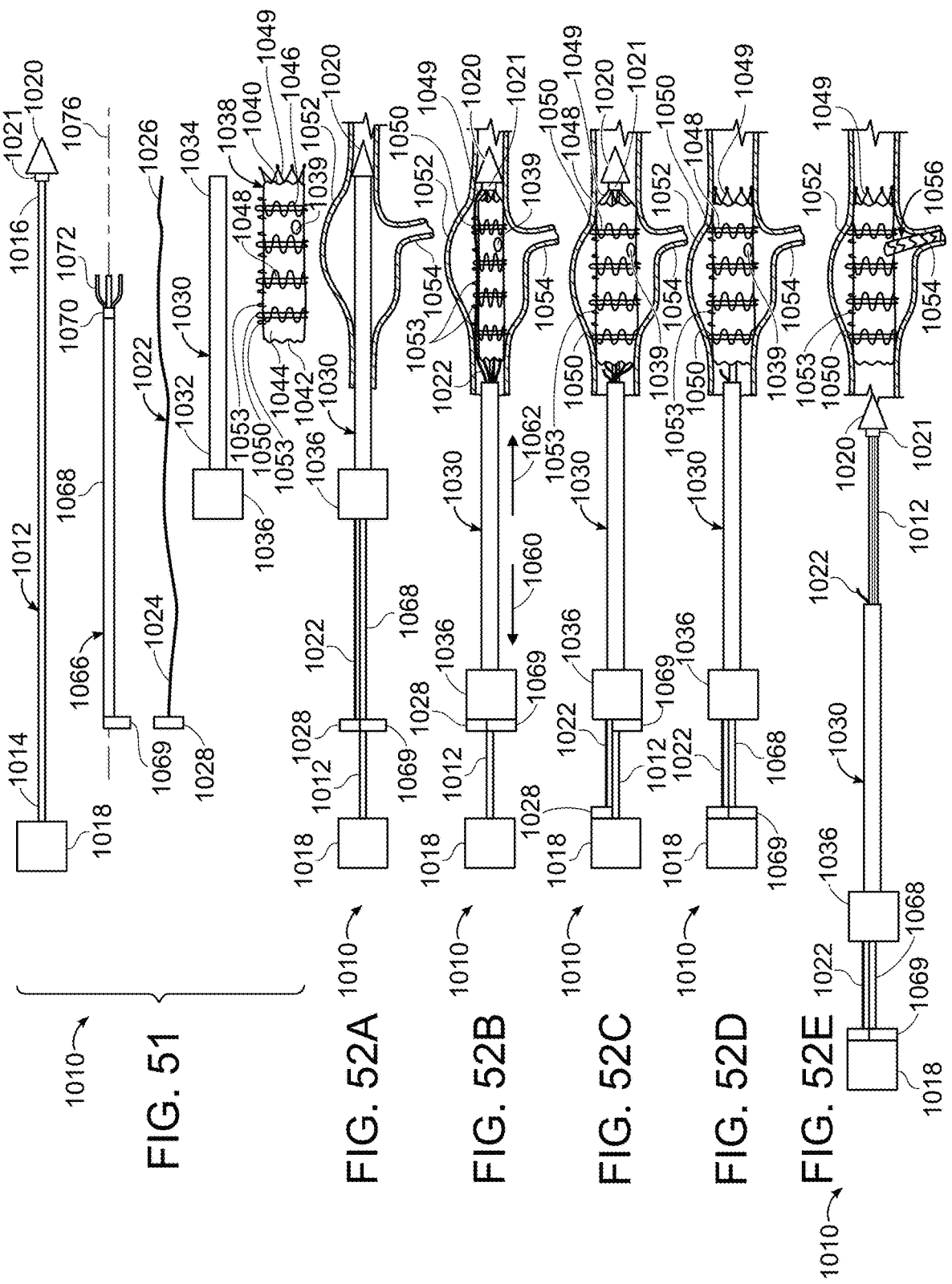
FIG. 51 is an exploded view of another embodiment of a stent graft delivery system of the invention, including, in addition to a torque component, circular ligature radial constraints about a stent graft, the diametrically opposed ends of collapsed ligatures are linked by a wire, wherein the collapsed ligatures wrap around the stent graft, and wherein the stent graft includes loops on struts of stents through which the collapse ligatures can extend, and includes a proximal bare stent that can be releasably fixed to an apex capture device at a nose cone of the stent graft delivery system.
FIG. 52A is an assembled side view of the stent graft delivery system shown in FIG. 51, following direction of an introducer sheath of the stent graft delivery system to an aneurysm spanning an arterial branch of the subject.
FIG. 52B is a side view of the embodiment shown in FIG. 52A, following retraction of the introducer sheath from the stent graft, thereby exposing the stent graft in a constricted position.
FIG. 52C is a side view of the embodiment shown in FIGS. 52A and 52B, following retraction of the wire linking diametrically opposed ends of the circular ligatures extending about the stent graft, thereby radially releasing the stent graft.
FIG. 52D is a side view of the embodiment shown in FIGS. 52A-52C, following release of the bare stent from the apex capture device.
FIG. 52E is a side view of the embodiment shown in FIGS. 52A-52D, following retraction of the torque component from the distal end of the stent graft, and retraction of a remainder of the delivery system not implanted at the aneurysm site from the stent graft, following implantation of a branch prosthesis through a fenestration and into the arterial branch spanned by the aneurysm.

FIG. 51 is an exploded side view of another embodiment of the stent graft delivery system of the invention. As shown therein, stent graft delivery system 1010 includes guidewire catheter 1012 having proximal end 1014 and distal end 1016. Proximal handle 1018 is fixed to proximal end 1014 of guidewire catheter 1012. Nose cone 1020 and apex capture device 1021 are fixed to distal end 1016 of guidewire catheter 1012. Torque component 1066 includes pushrod 1068, and at least two arms 1072, which can be self-expanding, extending from pushrod 1068. Optionally, hub 1070 is included as a link between pushrod 1068 and arms 1072. Hub 1070 defines a lumen about longitudinal axis 1076 and is fixed to pushrod 1068. Arms 1072 are disposed radially about hub 1070 and extend distally from hub 1070. Torque component handle 1069 is at a proximal end of pushrod 1068. Wire 1022 includes proximal end 1024 and distal end 1026. Wire 1022 can be fabricated of a suitable material, such as is known in the art, including, for example, Nitinol or some other shape memory alloy. Wire 1022 is sufficiently flexible not to injure the patient during advancement to an aortic aneurysm of a patient. Wire handle 1028 is fixed at proximal end 1024 of wire 1022. Introducer sheath 1030 includes proximal end 1032 and distal end 1034, and distal handle 1036 is fixed to proximal end 1032 of introducer sheath 1030. Stent graft 1038 includes proximal end 1040, distal end 1042, luminal graft component 1044, stents 1046 distributed along luminal graft component 1044, and ligatures 1048, arranged and configured as discussed above. Bare stent 1049 is fixed to distal end of stent graft 1038.

FIG. 52A is an assembled side view of stent graft delivery system 1010 shown in FIG. 51, wherein stent graft 1038 has been loaded within distal end 1034 of introducer sheath 1030, and radially constricted, at least in part, by wire 1022 threaded through diametrically opposed ends of circular ligatures 1048, as discussed above, and through stabilizing anchor loops 1053. In an embodiment, stent graft 1038 includes fenestration 1039.

In a method of the invention, stent graft delivery system 1010 is advanced to arterial aneurysm 1052 of a patient. In one embodiment, shown in FIG. 52A, introducer sheath 1030 is advanced to aneurysm site 1052 to thereby place stent graft 1038 at aneurysm 1052. As can be seen in FIG. 52B, distal handle 1036 is retracted in a proximal direction indicated by arrow 1060 toward proximal handle 1018, thereby retracting introducer sheath 1030 from stent graft 1038 at aneurysm 1052. As can be seen in FIG. 52B, despite retraction of introducer sheath 1030, stent graft 1038 is maintained in a radially constricted position by wire 1022 extending through ligature loops 1050 of ligatures 1048 traversing struts of stents 1046 distributed longitudinally along stent graft 1038. It is to be understood, however, that in an alternative embodiment, where wire 1022 is sufficiently rigid, stent graft delivery system 1010 can be advanced within an artery to a position distal to arterial aneurysm 1052, wherein stent graft 1038 is directed to arterial aneurysm 1052 by advancement of proximal handle 1018 and wire handle 1028 in a distal direction indicated by arrow 1062 toward distal handle 1036 to thereby direct radially constricted stent graft 1018 from introducer sheath 1030 to arterial aneurysm 1052.

Application of torque force to arms 1072 by rotation of torque component 1066 about longitudinal axis 1076 causes fenestration of stent graft 1038 to rotate about longitudinal axis 1076 until it is rotationally aligned with a branch blood vessel 1054 at aneurysm site 1052. In a method of the invention, advancement of the stent graft 1052 within radial constraint 1066 to aneurysm 1052, is followed by rotational alignment of at least one fenestration 1080.

Following direction of stent graft to a position that spans aneurysm 1052 and at least partial rotational and axial alignment of stent graft 1038 at aneurysm 1052, wire 1022 is retracted from ligature loops 1050 of ligatures 1048 and from anchor loops 1053. Proximal retraction of wire handle 1028 toward proximal handle 1018, in the direction indicated by arrow 1060, withdraws wire 1022 from suture loops 1050 of ligatures 1048 and anchor loops 1053, thereby enabling stent graft 1038 to fully expand from its radially constricted state, shown in FIG. 52B, to a radially expanded state, shown in FIG. 52C. As shown in FIG. 52D, stent graft 1052 is releasably secured to distal end 1062 of guidewire catheter 1058 at bare stent 1059 by a suitable apex capture device 1057, such as is known in the art. Bare stent 1059 is released from guidewire catheter 1058 by actuation of the apex capture device 1021. A torque component, as described above, is then retracted from distal end 1042 of stent graft 1038, whereby stent graft 1038 is fully implanted within aneurysm, and the remainder of stent graft delivery device 1010 is retracted from stent graft 1038 and the patient, and, separately, branch stent graft 1056 is directed through fenestration 1039 of 1038 into branch blood vessel 1054, by suitable means, such as is known in the art, as shown in FIG. 52E, thereby completing treatment of aneurysm 1052 of the patient by the method of the invention.

Figure 53:
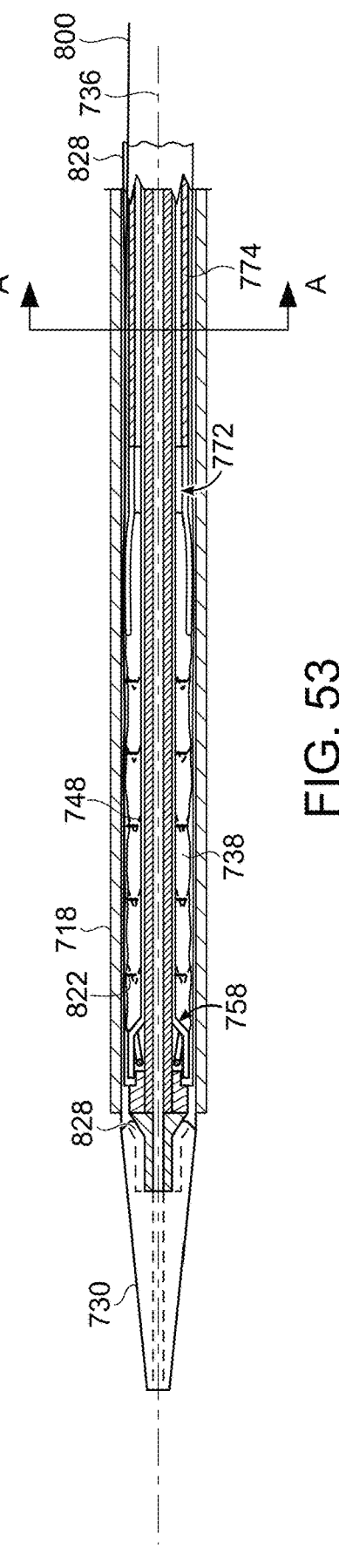
FIG. 53 is a cross-sectional view of the embodiment of the invention shown in FIGS. 50A and 50B, wherein a stent graft is radially constricted by a two-stage radial release component that includes a flexible sheath and a wire linking ends of radially constricting sutures.
Figure 54:
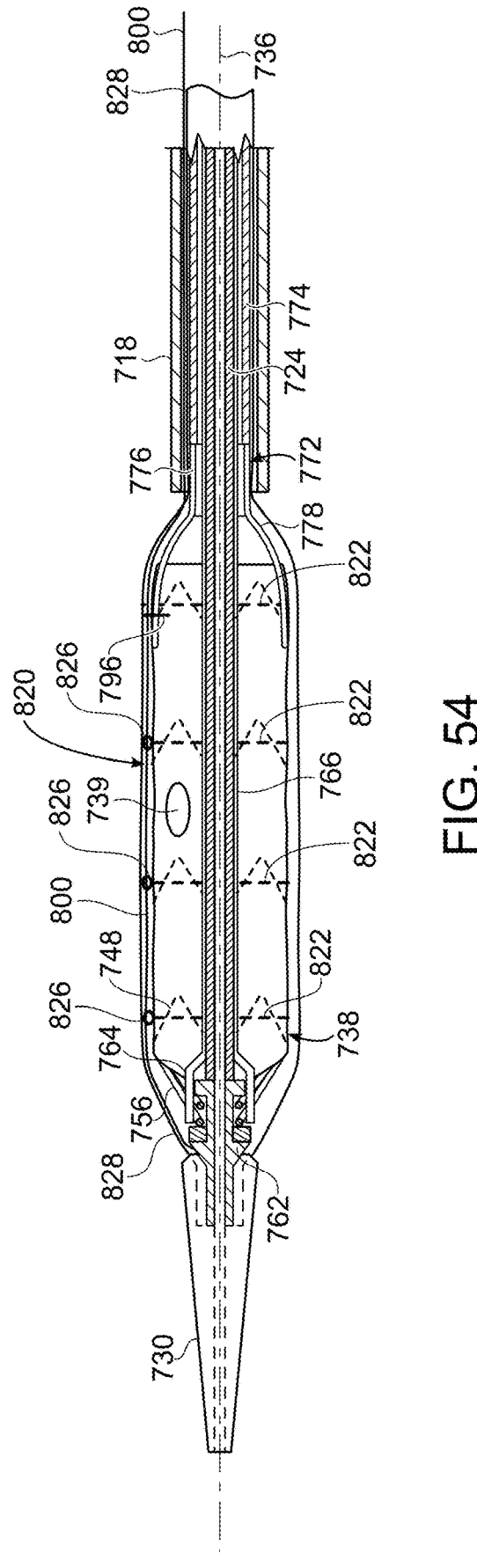
FIG. 54. is a cross-section of the embodiment shown in FIG. 53 following proximal retraction of an introducer sheath, wherein the stent graft is in a first intermediate radially expanded position, and before actuation of the two-stage radial release component.

In another embodiment of the stent graft delivery system of the invention, shown in FIGS. 53 and 54, the delivery system is like that shown in FIGS. 39 through 41, described above, but with constricting and wire 800 in addition to flexible sheath 828. In this embodiment, radial constraint 820 includes ligatures 822, wire 800, and flexible sheath 828. Ligatures 822, or threads, span each of stents 748 of stent graft 738. Wire 800 extends through a loop 826 of each Ligature 822 (FIG. 54), whereby retraction of wire 800 from ligature 822 releases stent graft 738. It is to be understood, however, that, in the alternative ligatures 822 can be substituted with ligatures 900, such as are shown in FIG. 50A, that are collapsed to form ends 827, 829 that are linked by wire 800, in which case ligatures 900 can be secured to the remainder of stent graft 738 by stitches 904 to prevent release of ligatures 900 following retraction of wire 800 from ends 827, 829. Flexible sheath 828 extends between stent graft 738, and introducer sheath 718, and is tucked into, or under, nose cone 730.

Figure 53A:
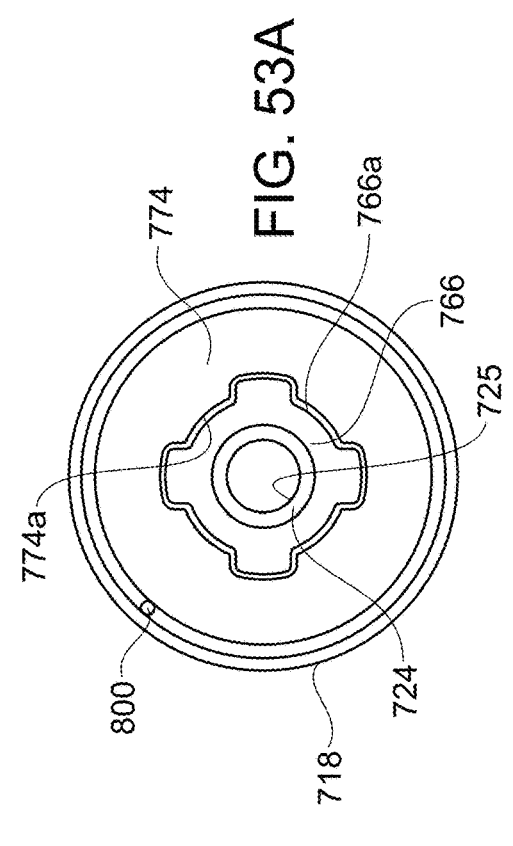
FIG. 53A is cross-sectional view of the embodiment shown in FIG. 53 taken along line A-A.
Figure 55:
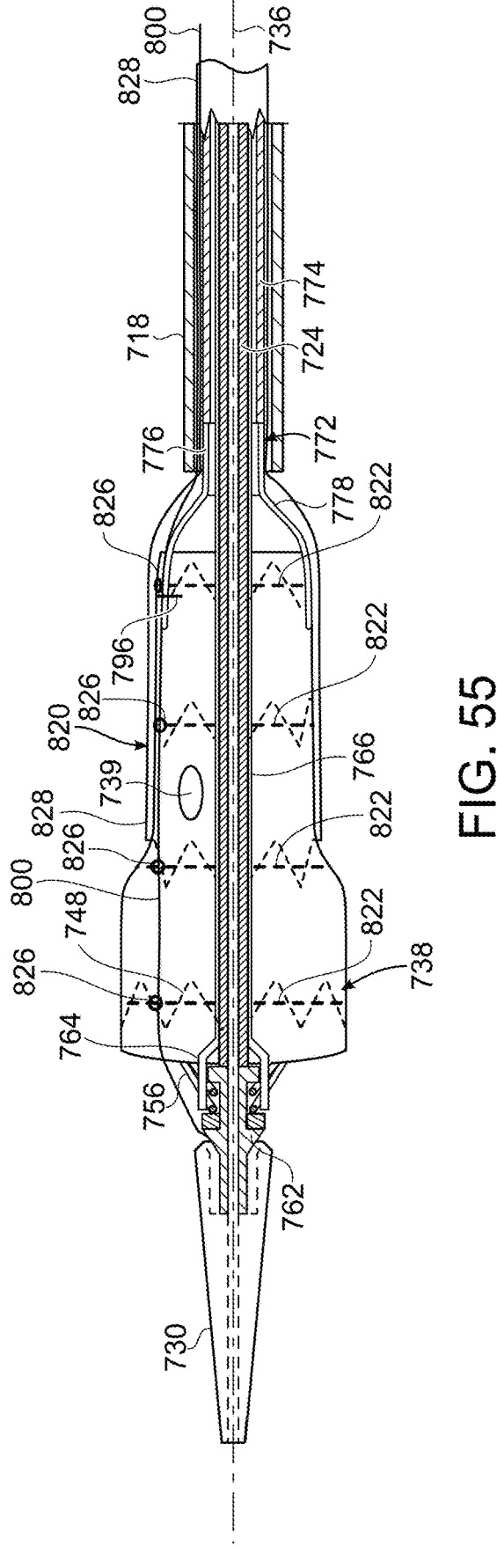
FIG. 55 is a cross-section of the embodiment shown in FIG. 54 following partial retraction of a flexible sheath that is located between the stent graft and the introducer sheath when in an undeployed state, but exposed upon retraction
Figure 56:
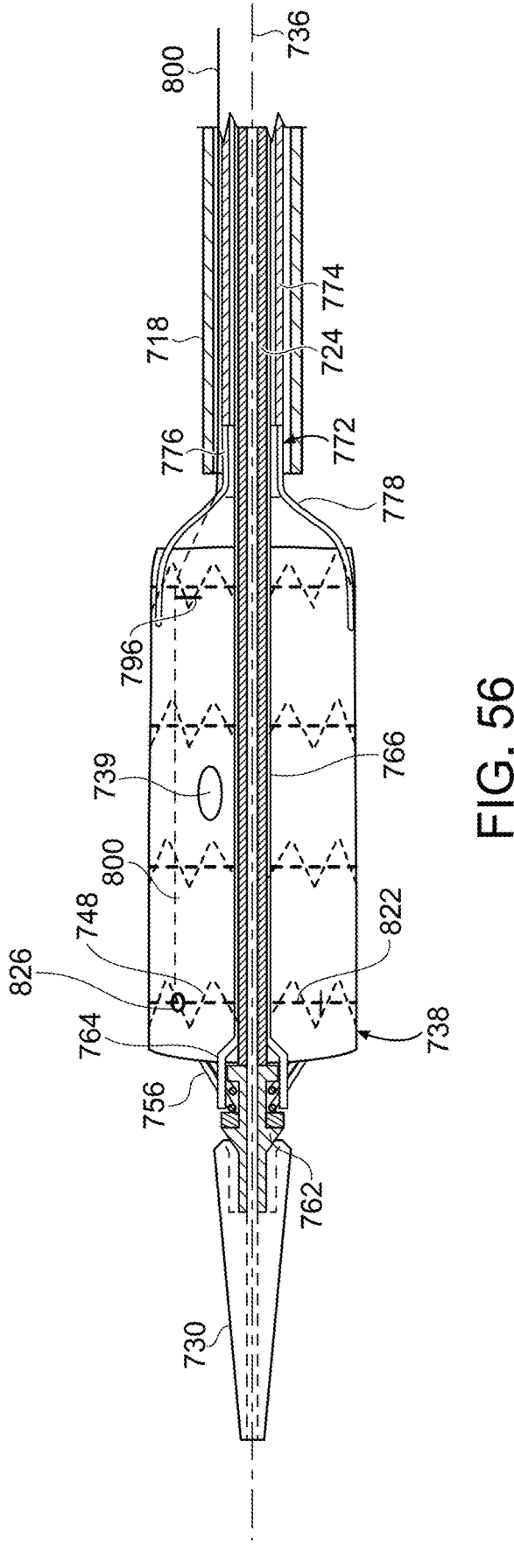
FIG. 56 is a cross-section of the embodiment of FIGS. 54 and 55, following complete retraction of the flexible sheath, leaving the stent graft in a second intermediate radially expanded position.
Figure 57:
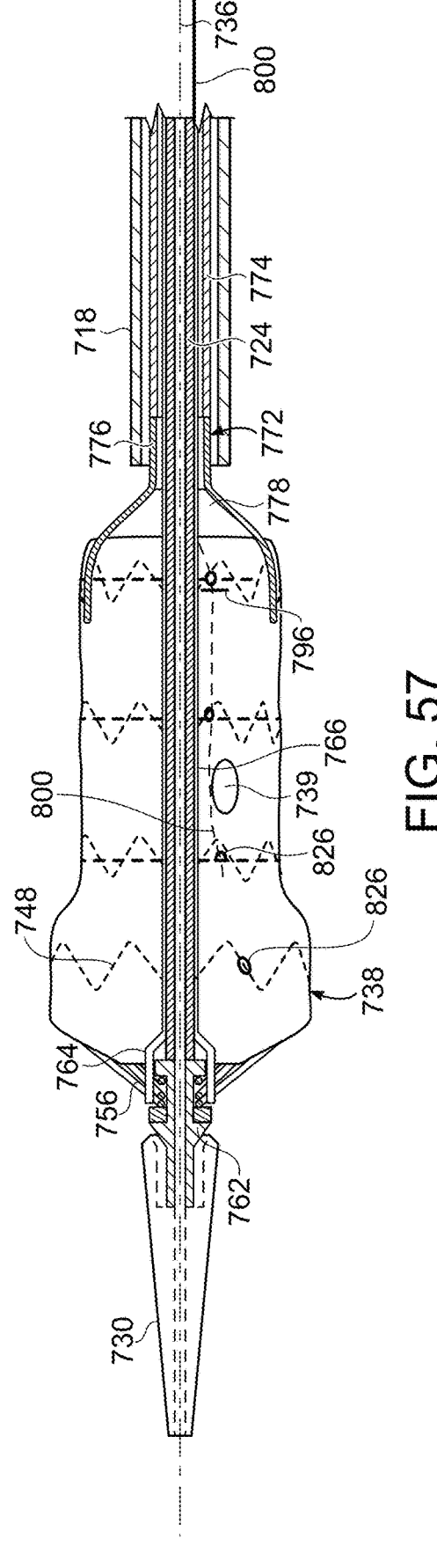
FIG. 57 is a cross-section of the embodiment of FIGS. 54, 55, and 56, following partial retraction of a wire linking ends of ligatures radially constraining the stent graft.
Figure 58:
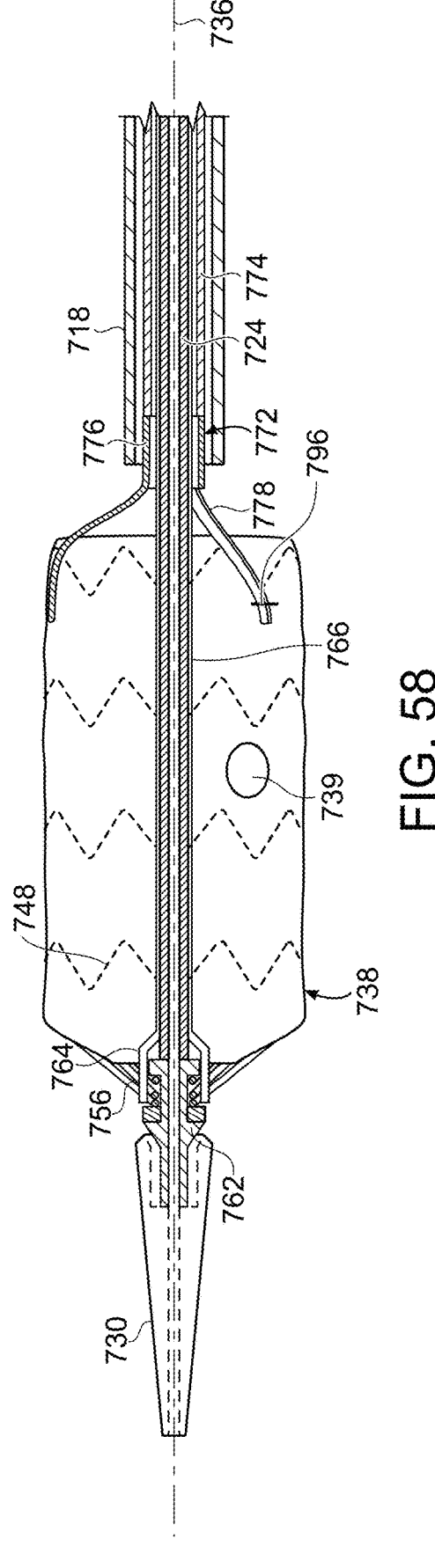
Figure 59:
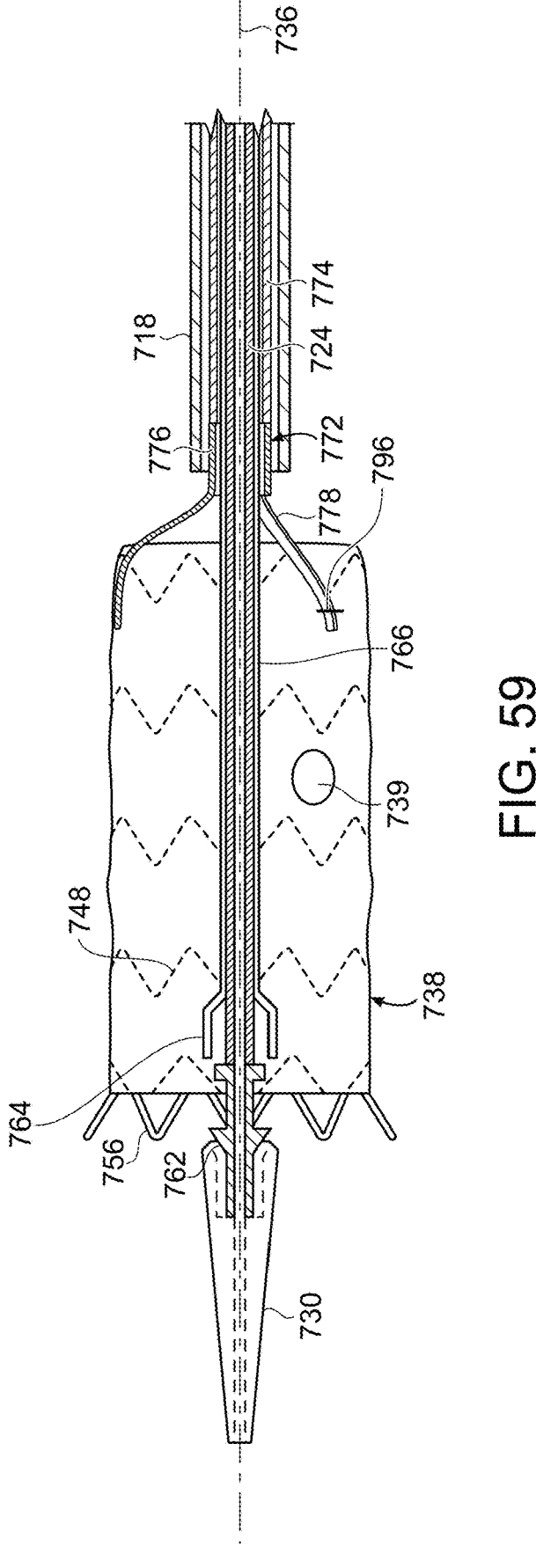
Figure 60:
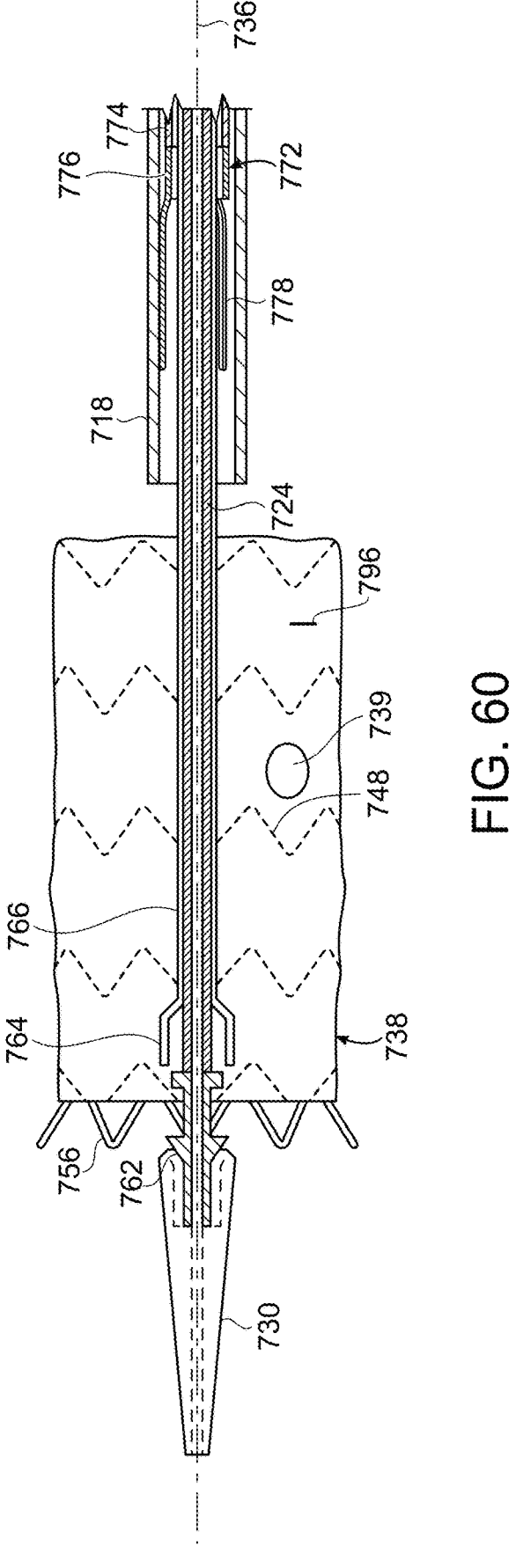
Figure 61:
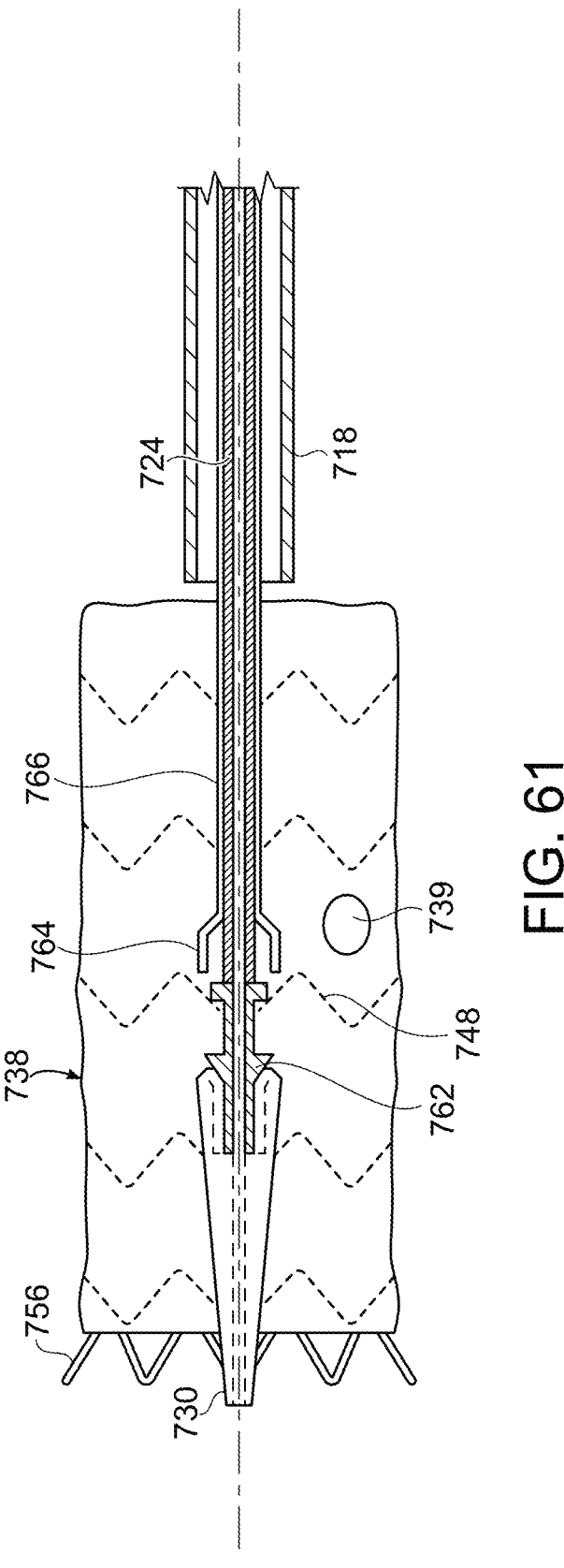

FIG. 53A, which is a cross-section of FIG. 53, taken along lines A-A of FIG. 53, shows that wire 800 extends between introducer sheath 718 and pushrod 774. FIG. 54 shows the stent graft delivery system of FIG. 53, but following retraction of introducer sheath 718, thereby causing flexible sheath 828 to radially constrict stent graft 820 in a first intermediate radially-expanded position. A two-stage expansion of stent graft 820 is thereby possible, whereby proximal retraction of introducer sheath 718, resulting in radial constriction of stent graft 838 by flexible sheath 828 in a first intermediate radially-expanded position, as shown in FIG. 54 is a first stage. Retraction of flexible sheath 828 from stent graft 838 and consequent partial radial expansion of stent graft 838 to a second intermediate radially-expanded position, shown in the progression from FIG. 54 to FIG. 55, and from FIG. 55 to FIG. 56, is a second stage. Proximal retraction of wire 800 from ligatures 822 thereafter allows full radial expansion of stent graft 838 (but for release of bare stent 756, and retraction of torque component 772), as can be seen in the progression from FIG. 56 to FIG. 57, and from FIG. 57 to FIG. 58. Proximal apex capture component 764 is retracted and separated from proximal apex capture component 762 to thereby release bare stent 756, as shown in FIG. 60. Thereafter, torque component 772 is retracted from stent graft 738, as shown in FIG. 59, thereby fully deploying stent graft 738 at a surgical site. The delivery device can then be removed from the surgical site, as shown in FIG. 61.

Although not shown, it is to be understood that control rods can be employed in the device and method of the invention to independently radially constrict various longitudinal portions of a stent graft, such as proximal and distal portions of a stent graft. It is also to be understood that a plurality of control rods can be distributed radially about a stent graft, either evenly, evenly in conjunction with a fenestration in the stent graft, or in another pattern or unevenly. It is also to be understood that the stent graft delivery system of the invention can include a plurality of control rods that each separately and independently control radial expansion of the same portion of stents, in particular a proximal portion of stents. The plurality of control rods are laterally and longitudinally arranged relative to each other about a circumference of the outside or inside surface of the luminal graft component (not shown).

In another embodiment, the invention is a combination of a leg stop, a leg clasp, and an introducer sheath. In an embodiment, shown in FIG. 62, the invention is a stent graft delivery device 1100 that includes leg clasp 1102 which, in combination with introducer sheath 1104, captures leg 1106 of bifurcated stent graft 1108, and leg stop 1110, that limits proximal travel (toward the surgeon) of introducer sheath 1104, either directly or indirectly, to thereby prevent premature release of distal end 1112 of bifurcated stent graft 1108 during implantation at a surgical site. Stent graft 1108 can include one or more fenestrations 1109.

Figure 63:
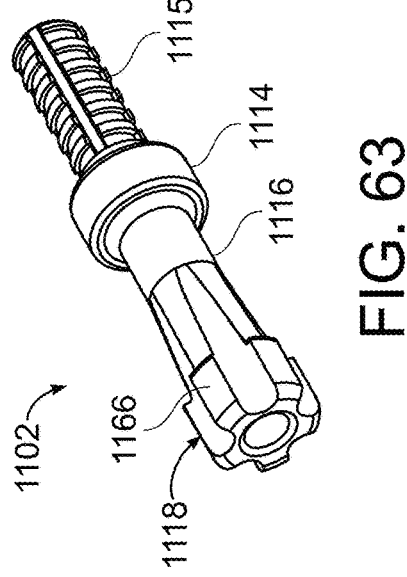

The embodiment of leg clasp 1102 shown in FIG. 63 includes barrel portion 1114, spool portion 1116 extending from barrel portion 1114 along longitudinal axis of barrel portion 1114, and rim portion 1118 at an end of spool portion 1116 opposite that of barrel portion 1114, rim portion 1118 having a radial diameter greater than that of spool portion 1116 but less than that of barrel portion 1114.

Figure 64:
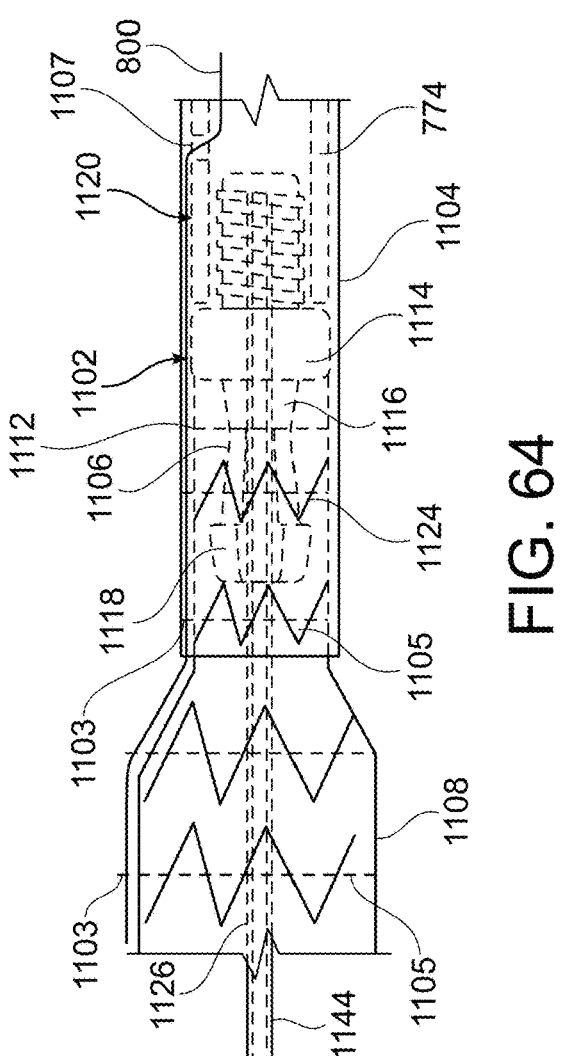
Figure 65:
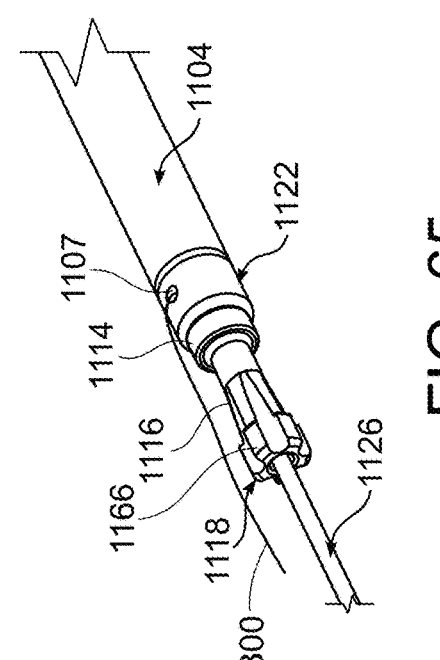

As can be seen in FIGS. 63-65, guidewire 724 extends from apex capture device 1128 through leg clasp 1102. Bifurcated stent graft 1108 extends from apex capture device 1128 to leg clasp 1102, and is secured at each of apex capture device 1128 and at leg clasp 1102.

Rim portion 1118 of leg clasp 1102 of the invention can include radially extending spokes 1166, as shown in FIGS. 63 and 65. Leg clasp 1102 of the invention can be formed, for example, at least in part, of at least one component selected from the group consisting of stainless steel, polyester, polyetheretherketone (PEEK) and acrylonitrile butadiene styrene (ABS).

Leg clasp 1102 captures leg 1106, thereby adding stability to bifurcated stent graft 1108 during the cannulation of leg 1164. As can be seen in FIG. 64, support member 1120, which includes pushrod 774 (or support tube) and hypo-tube 1168 (shown, for example in FIGS. 72, 72A, and 72B) is fixed at pushrod 774 to barrel portion 1114 of leg clasp 1102 and extends from barrel portion 1114 in a direction opposite that of spool portion 1116. In embodiments of the invention that include leg clasp 1102, wire 800 extends through opening 1107 in pushrod 774, as shown in FIG. 64. Introducer sheath 1104 (FIG. 65) has an internal diameter relative to that of barrel portion 1114 sufficient to permit movement between a first position that covers barrel portion 1114, spool portion 1116, and rim portion 1118, and a second position that exposes spool portion 1116 and rim portion 1118.

Wire 800 extends along the outside surface of stent graft 1108 and through loops 1103 of constraints 1105. Wire also extends proximally from stent graft 1108 along an outside surface of leg clasp 1102 and through opening 1107 of push rod 774, and extends proximally through push rod 774 and hypo-tube 1168 (shown, for example, in FIG. 72) until it connects to wire handle 803 (FIG. 27A).

Figure 62:
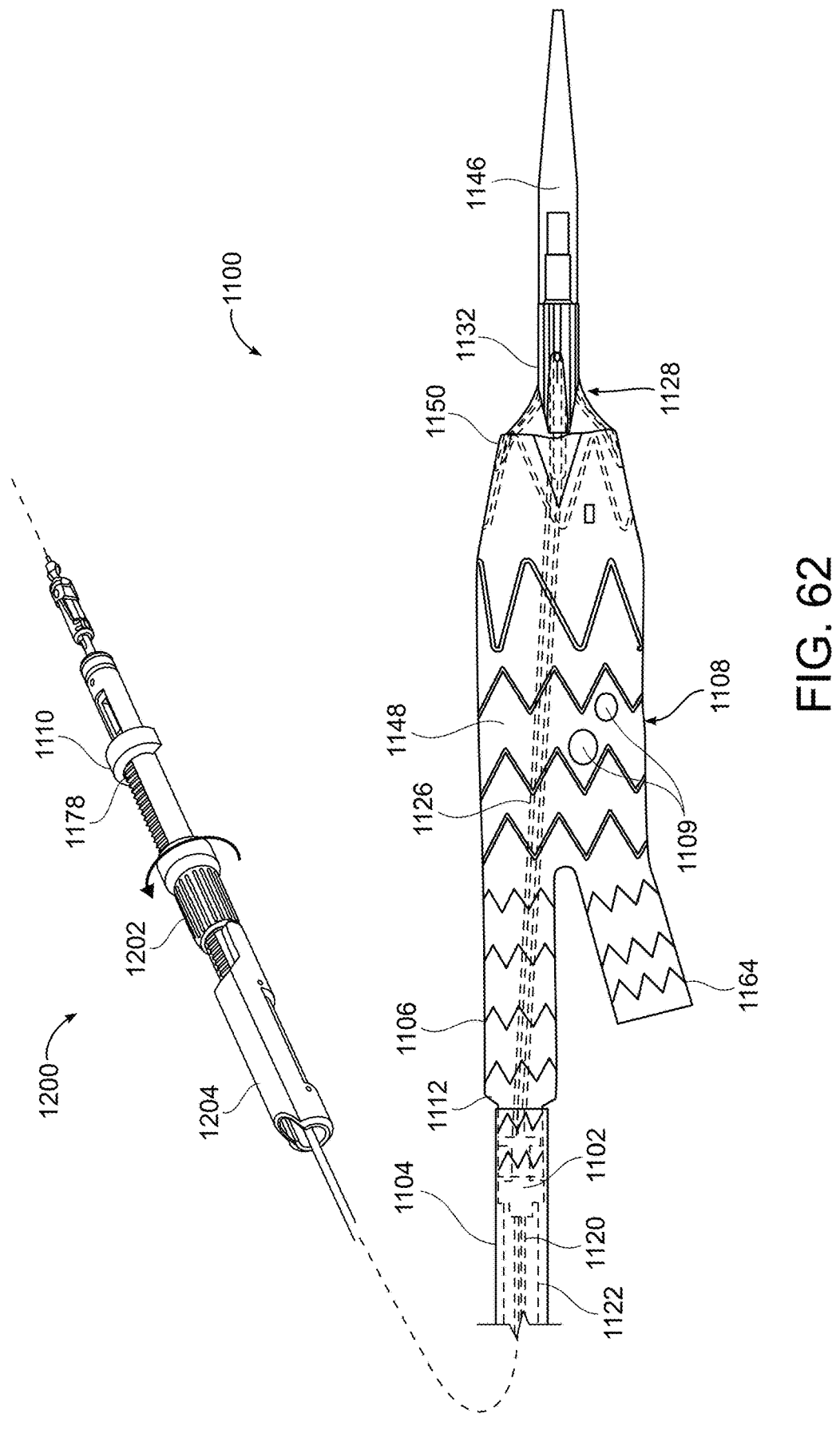
Figure 66:
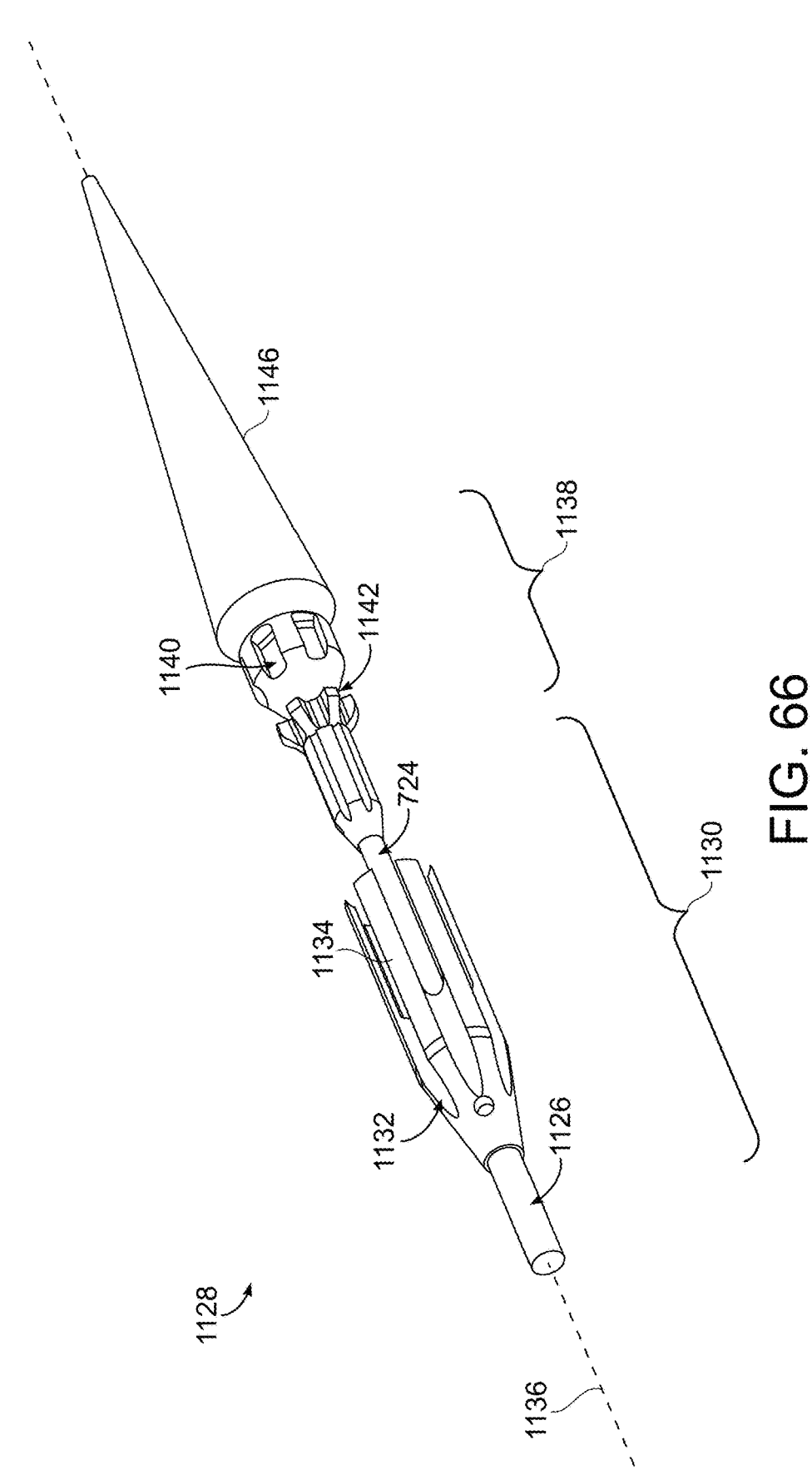
Figure 69:
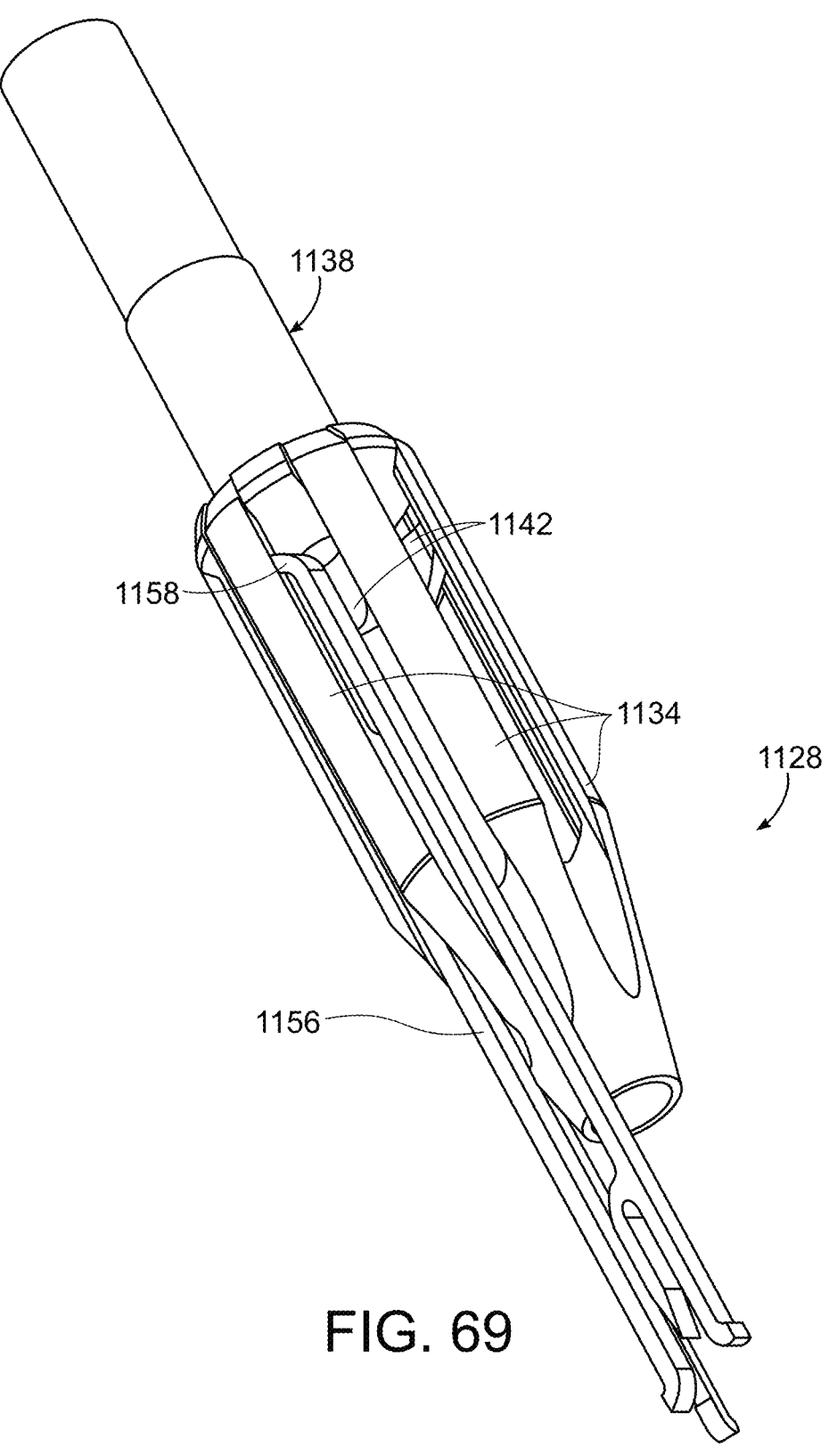

Apex capture device 1128 of the invention can be employed, in an embodiment of the invention, in conjunction with the leg clasp 1102, as shown in FIG. 62. Apex capture device 1128, as shown in FIG. 66, includes proximal apex capture portion 1130, including nose portion 1132 and a plurality of tines 1134 extending distally from nose portion 1132. Tines 1134 are radially distributed about longitudinal axis 1136 of delivery device 1100 (FIG. 62). Distal apex capture portion 1138 defines slots 1140 distributed radially about longitudinal axis 1134 and are mateable with tines 1134 by relative movement of proximal apex capture portion 1130 and distal apex capture portion 1138 along longitudinal axis 1134. A plurality of bosses 1142 extend radially from longitudinal axis 1136 between nose portion 1132 and distal apex capture portion 1138. Bosses 1142 are aligned with slots 1140 along longitudinal axis 1136 and in non-interfering relation with movement of tines 1134 when tines 1134 are in mating relation with slots 1140, as shown in FIG. 69. Guidewire catheter 724, to which distal apex capture portion 1138 is fixed, extends through outer control tube 1126 and proximal apex capture portion 1130. Outer control tube 1126 is fixed to proximal apex capture portion 1130, whereby movement of outer control tube 1126 causes movement of the proximal apex portion 1130 along longitudinal axis 1136 between a first position, in which tines 1134 are mated with slots 1140 and overlie bosses 1142, and a second position, in which tines 1134 are not mated with slots 1140 and do not overlie bosses 1142. Nose cone 1146 extends distally from guidewire catheter 724 and distal apex capture portion 1138.

Figure 67:
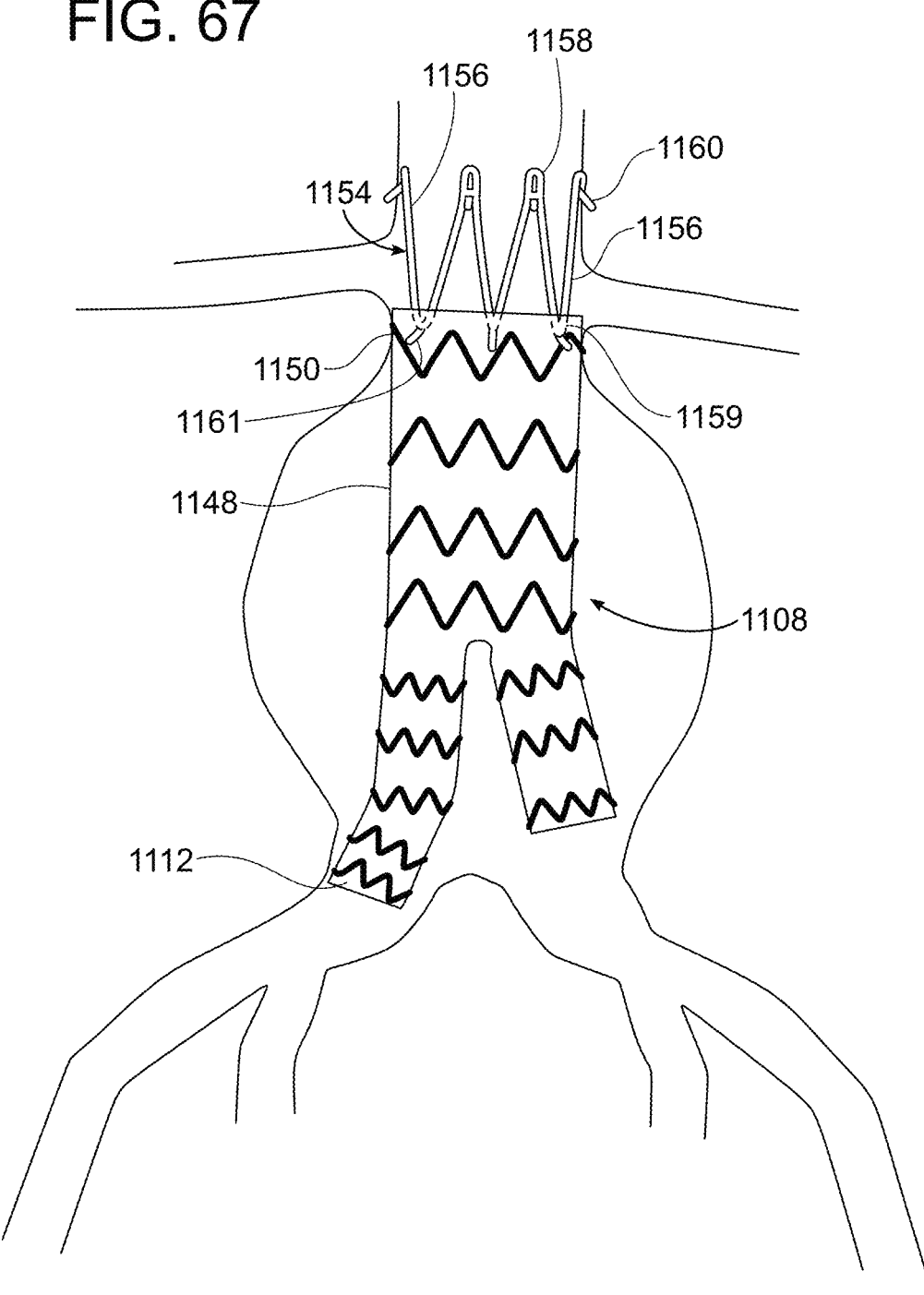

As can be seen in FIGS. 67 and 71, bifurcated stent graft 1108 includes luminal graft component 1148 having: proximal end 1150; distal end 1112; stents 1152 along luminal graft component 1148; and bare stent 1154 at proximal end 1150. A clasping stent, in this case bare stent 1154 includes struts 1156 linked by proximal apices 1158 and distal apices 1159, wherein struts 1156 extend between tines 1134, as can be seen in FIG. 69. Proximal apices 1158 of bare stent 1154 extend proximally from proximal end 1150 of luminal graft component 1148. In the embodiment shown in FIG. 67, which depicts a stent graft 1108 following implantation, suprarenal barbs 1160 extend from proximal apices 1158 of bare stent 1154. Distal apices 1159 of bare stent 1154 include infrarenal barbs 1161. As can be seen in FIGS. 68-71, a portion of proximal apices 1158 extend between bosses 1142 and distal apex capture portion 1138 when tines 1134 are mated to slots 1140. As can be seen in FIG. 68, bosses 1142 can extend into apertures 1141 defined by proximal apices 1158 and bridges 1143 at proximal apices 1158 of bare stent 1154. At least one suprarenal barb 1160 can extend from bare stent 1154 into a radial restraint 1162, or pilot holes, of proximal capture portion 1130, as shown in FIG. 70. Distal apices of bare stent 1154 can be nested between proximal apices of most proximal stent 1163.

In another embodiment, not shown, the proximal apices of clasping stent do not extend proximally from proximal end of luminal graft component 1148, and a crown stent is located between the clasping stent and proximal end 1150 of luminal graft component 1148. Proximal apices 1130 of the clasping stent, in this embodiment, are nevertheless exposed, whereby they can be secured by proximal apex capture portion 1130 and distal apex capture portion 1138 when they are in mating relation.

The stent graft delivery system of the invention can further include, in an embodiment, slider 1172, shown in FIGS. 72, 72A, and 72B. Slider 1172 includes slider body 1174 defining a central orifice through which support member 1120 extends. Support member 1120, as shown in FIG. 72A, includes pushrod 774 and hypo-tube 1168. Flush valve orifice 1176 extends substantially normal to the central orifice. Slider body 1174 is detachably fixable to track 1178 by suitable means, such as, for example, release lever 1180, (shown in FIGS. 73 and 74). Slider cap 1182 is coupled to a distal end of slider body 1174. Slider cap 1182 defines a central orifice that is substantially aligned with the central orifice of slider body 1174 through which support member 1120 extends. Sheath valve knob 1184 is threadably coupled to slider body 1174. Introducer sheath 1104 is fixed to and extends distally from a distal end of slider cap 1182 and defines a lumen that is substantially aligned with the central opening of slider body 1174 through which support member 1120 extends. Wiper valve 1186 at the central opening of slider body 1174 is proximal to flush valve orifice 1176 and forms a seal about support member 1120. X-valve 1188 is at the central opening of slider body 1174 proximal to wiper valve 1186 and forms a seal about support member 1120. Sheath valve 1190 is at the central opening of slider body 1174 and proximal to x-valve 1188. Sheath valve 1190 is operable by activation of knob 1184 to seal the central opening.

In an embodiment, support tube 1122 (or push rod) is a component of support member 1120, shown in FIGS. 72 and 72A. Hypo-tube 1168 of support member 1120 also includes hypo-tube 1168, also shown in FIG. 72A. In embodiments of the invention that include a torque component, such as those shown, for example, in FIGS. 28 through 60, wire 800 extends proximally along an outside surface of pushrod 774 and passes through opening 1167 at distal end of hypo-tube 1168, and extends proximally within hypo-tube 1168 until it reaches proximal handle 714, as shown, for example in FIGS. 27, 27A, 27B, and 27C. Support member 1120 can be fixed to proximal handle 714 (FIG. 27). As can be seen in FIGS. 82A and 82B, in use, hemostasis valve 1172 can be held stationary while handle body 1200 (along with support member 1120 and the remainder of the delivery system, except hemostasis valve 1172 and introducer sheath 1104) are removed from the surgical site and the patient.

An assembled view of one embodiment of the invention is shown in FIG. 73. A method of the invention, and the function of handle 1200 is illustrated, for example, in the progression of FIGS. 73 to 80. Before lead screw nut 1202 is turned to retract introducer sheath 1104. Introducer sheath 1104 completely covers bifurcated stent graft 1108, which is loaded therein proximal to nose cone 1146, as can be seen in FIG. 73. Threads of lead screw nut 1202 are engaged with track 1178, whereby rotation of lead screw nut 1202, while lead screw nut 1202 abuts the proximal end of distal handle 1204, causes proximal movement of track 1178, slider 1172, and introducer sheath 1104 toward proximal handle, or proximal end 1111 of housing 1210, thereby causing introducer sheath 1104 to retract from bifurcated stent graft 1108, as shown in FIG. 74. Proximal movement of track 1178 can continue until proximal end 1206 of track 1178 abuts leg stop 1110, which is removably fitted within housing 1210, also referred to herein as handle body, of delivery device 1200. Upon contact of track 1178 with leg stop 1110, further rotation of lead screw nut 1202 is prevented, as is retraction of introducer sheath 1104 from bifurcated stent graft 1108. At this point, introducer sheath 1104 still covers leg 1106 of bifurcated stent graft 1108, thereby trapping at least one stent 1124 of bifurcated stent graft 1108 between leg clasp 1102 and introducer sheath 1104, as previously shown in FIG. 64. Bare stent 1154 at proximal end 1150 of bifurcated stent graft 1108 is still secured to apex capture device 1128. By securing proximal end 1150 and distal end 1112 of bifurcated stent graft 1108, the surgeon can better axially and longitudinally orient and place bifurcated stent graft 1108 at the surgical site.

One embodiment of leg stop 1110 is shown in FIGS. 75-76. As can be seen from FIG. 75, leg stop 1110 includes body 1212 and wings 1214 extending laterally from body 1212. Wings 1214 wrap partially around a circumference of handle body 1210 of delivery device 1200 (FIG. 74). Body 1212 fits within slot 1216 (FIG. 73) defined by handle body 1210 and to rest on or partially around support member 1120 extending through handle body 1210 (see, e.g., FIGS. 72 and 73). As can be seen in FIG. 76, body 1212 defines channel 1218 within which support member 1120 fits. Openings 1220 defined by body 1212 are optional. Leg stop 1110 is made of a suitable material, such as is known in the art. Examples of suitable materials include engineering plastics, such as acrylonitrile butadiene styrene (ABS), polyether ether ketone (PEEK), polysulfone, etc.). Leg stop 1110 can be made of an elastic or flexible material, whereby wings 1214 can deform or distend slightly, thereby causing leg stop 1110 to remain secure within slot 1216 of handle body 1210 until it is to be removed by the physician.

Once properly oriented, bare stent 1154 can be released from apex capture device 1128, as shown in FIGS. 77 through 78, by actuation of clasp 1224 at proximal end of support member 1120. Specifically, in one embodiment, shown in FIGS. 77A through 77C, proximal clasp assembly 1224 includes outer coupling 1123 and fixed component 1125 that are in mating relation. Fixed component 1125 is fixed to the proximal end of elongate member guidewire catheter 724, shown in FIG. 72A. Outer coupling 1123 is fixed to outer control tube 1126. Release of bare stent 1154 (FIG. 71) is effected by moving outer coupling 1123 at first distally FIG. 77A, and then rotating fixed component 1125 ninety degrees, as shown in the transition from FIG. 77A to FIG. 77B. Thereafter, outer coupling 1123 is moved proximally, whereby prongs 1127 of outer coupling 1123 are mated with slots 1129 of fixed component, as shown in the transition from FIG. 77B to FIG. 77C. Proximal movement of outer coupling 1123 causes proximal movement of outer control tube 1126 that, in turn, causes proximal movement of proximal apex capture portion 1130 of apex capture device 1128 (FIGS. 66 and 68-71) and tines 1134 of proximal apex capture portion 1130 from between struts 1156 of bare stent 1154, thereby releasing bare stent 1154 from apex capture device 1128, as shown in FIG. 78. Release of bare stent 1154 causes proximal apices to 1158 to land at a blood vessel wall proximal to the surgical site, such as is represented at FIG. 67.

Referring again to FIG. 78, bifurcated stent graft 1108 will continue to be stabilized at the distal end of stent graft 1112 by leg clasp 1102 and introducer sheath 1104 because neither will move relative to each other; track 1178 is abutting leg stop 1110 and lead screw nut 1202 is prevented from rotating in either direction: in one direction by leg stop 1110; and in the other direction by resistance of introducer sheath 1104 to advancing back over the bifurcated stent graft 1108 from which it was retracted. Following release of bare stent 1154, as indicated by the position of clasp 1224, shown in FIG. 78 and in FIGS. 79A through 79C. As shown in the transition from FIGS. 79A to 79B, leg stop 1110 can be removed by the surgeon. Removal of leg stop 1110 enables track 1178 to move proximally toward the surgeon by sliding lead screw nut 1202 in a proximal direction, or by rotating lead screw nut 120, as shown in the transition from FIGS.

79B to 79C, thereby causing retraction of introducer sheath 1104 and release of bifurcated stent graft 1108 from delivery device 1200, as shown in FIG. 80. Delivery device 1200 can then be retracted from the bifurcated stent graft 1108 and the subject, thereby completing implantation.

As can be seen in FIGS. 81A through 81C, following retraction of track 1178, slider 1172, and introducer sheath 1204 from stent graft 1108, indicated in the transition from FIG. 81A to FIG. 81B, and after release of bare stent 1154 and leg 1106, as described above, release lever 1180 is still closed. Release lever 1180 is actuated by lifting, as shown in the transition from FIG. 81B to 81C. The position of lead screw nut 1202 is not significant here, the remaining distance traveled by track 1178 and introducer sheath 1172 to release leg 1106 from leg clasp 1102 being achievable either by direct longitudinal movement of lead screw nut 1202 (FIG. 81B) or by rotation of lead screw nut 1202 (FIG. 81C). In either case, actuation of release lever 1180 enables separation of slider 1172 from handle 1210 of the delivery device by proximal movement of handle 1210, to thereby remove the handle and attached component parts, leaving behind only slider 1172 and introducer sheath 1104, as shown in FIGS. 82A and 82B. Thereafter, slider 1172 can be sealed by rotation of sheath valve knob (FIG. 72) until delivery is made through introducer sheath 1104 of, for example, a stent graft leg extension or a branch stent graft.

A method to treat an abdominal aortic aneurysm can further include the step of cannulating a leg 1164 of bifurcated stent graft 1108 with an extension stent graft (not shown) while leg 1106 is being held at least partially within introducer sheath 1104. The method of treating an abdominal aortic aneurysm can further include the step of opening clasp 1224 at a proximal end of delivery device 1198 to release bare stent 1154 at proximal end 1150 of the bifurcated stent graft 1108. Leg 1106 of bifurcated stent graft 1108 is constrained within introducer sheath 1104 when apex capture device 1128 is opened to release bare stent 1154. Leg 1106 is then released by removing leg stop 1110, which allows further retraction of track 1178 and introducer sheath 1104 to thereby expose and release the captured portion of leg 1106.

In another embodiment, the method of treating an abdominal aortic aneurysm can further include the step of detaching slider 1172 and introducer sheath 1104 from the remainder of delivery device 1200, and then withdrawing the remainder of device 1200 from the patient while leaving the slider 1172 and introducer sheath 1104 substantially in place. Thereafter, an extension stent graft (not shown) can be delivered through introducer sheath 1104 and to the leg 1106, and cannulating leg 1106 with the extension stent graft. Cannulated leg 1106 overlaps the extension stent graft by at least two stents of each of the cannulated leg 1106 and the extension stent graft. The cannulated leg 1108 can include at least one more stent, called a "locking stent," than is required to overlap the extension leg by two stents of each of the cannulated leg 1106 and the extension stent graft. A second stent of cannulated leg 1106 can be located within the graft material of the bifurcated stent graft. The second stent at the distal end of bifurcated stent graft 1108 includes barbs that can extend inwardly and proximally from the stent.

FIG. 83 is an exploded view of one embodiment of a modular fenestrated bifurcated stent graft 1226 that can be delivered by a method of the invention. As can be seen in FIG. 83, cuff 1228 is a stent graft that defines fenestrations 1230. Bifurcated extension 1232 is also a stent graft. FIG. 84 is a view of the fenestrated bifurcated stent graft 1226 once assembled by the method of the invention. A multi-pronged torque component can be employed during delivery of fenestrated cuff 1228 to a treatment site, such as is described in U.S. Ser. No. 16/433,823, filed Jun. 6, 2019, and U.S. Ser. No. 63/111,357, filed Nov. 9, 2020, the relevant teachings of which are incorporated herein by reference in their entirety. Thereafter, a leg clasp 1102, shown in FIG. 63, is employed during delivery of bifurcated extension 1232 by capturing a distal end of one leg of bifurcated extension 1232, as shown in FIG. 64, to assemble modular stent graft 1226, such as by overlapping sections of cuff 1228 and bifurcated extension 1232, before finally releasing modular fenestrated bifurcated stent graft 1226 and retracting the delivery system from the patient.

The methods of the invention have an advantage of repositioning of a graft (e.g., bifurcated graft, second stent graft, third stent graft) if, for example, a clinician determines initial positioning of the graft is less than optimal. The graft can be repositioned at its proximal and distal end and proximally and distally in an aorta or branch of an aorta, such as a common iliac artery. It is to be understood that the various embodiments of the invention described herein can be combined, such as combination of methods of constraining stent grafts with either or both of employment of prongs of a delivery device to control rotation at a distal end of the stent graft and employment of a leg clasp, an introducer sheath, and a leg stop, as discussed above to control implantation of a bifurcated stent graft.

While example embodiments have been particularly shown and described, it will be understood by those skilled in the art that various changes in form and details may be made therein without departing from the scope of the embodiments encompassed by the appended claims. For example, although not shown, the at least one fenestration of the stent grafts employed in the methods or as components of the delivery systems of the invention can include fenestration locks as described in PCT/US2018/019352; moveable fenestrations as described in PCT/US2018/019353; fenestration rings as described in PCT/US2018/019351; and crimped adapters as described in PCT/US2018/019350, the relevant teachings of all of which are hereby incorporated by reference in their entirety. In addition, the relevant teachings of PCT/2017/037157, PCT/US2017/044822, and PCT/US2018/052400 are incorporated by reference in their entirety. Also for example, although not shown, a flexible sheath for use in the delivery systems of the invention can include an arrangement of openings that will cause the flexible sheath to have a luminal configuration having a constricted diameter and a ligature extending through the openings that causes the openings to conform to the arrangement, thereby configuring the flexible sheath to confirm to the constricted radial diameter of the luminal configuration, the ligature being proximally retractable from the openings to thereby release the flexible sheath from the constricted radial diameter, as described in PCT/US2018/019354, the relevant teachings of which are hereby incorporated by reference in their entirety.

Vascular prostheses implanted by the stent graft systems and methods of the invention can be implanted, for example, by transfemoral access. Additional branch prostheses that are directed into the vascular prostheses of the invention can be implanted, for example, by supraaortic vessel access (e.g., through the brachial artery), or by transfemoral access, or access from some other branch or branches of major blood vessels, including peripheral blood vessels.

The teachings of all patents, published applications and references cited herein are incorporated by reference in their entirety. The relevant teachings of all patents, published applications and references cited herein are incorporated by reference in their entirety. The relevant teachings of U.S. Pat. Nos. 8,292,943; 7,763,063; 8,308,790; 8,070,790; 8,740,963; 8,007,605; 9,320,631; 8,062,349; 9,198,786; 8,062,345; 9,561,124; 9,173,755; 8,449,595; 8,636,788; 9,333,104; 9,408,734; 9,408,735; 8,500,792; 9,220,617; 9,364,314; 9,101,506; 8,998,970; 9,554,929; 9,439,751; 9,592,112; 9,655,712, 9,827,123, 9,877,857, 9,907,686; 10,105,248; 10,307,275; 10,524,893; 10,390,932; 10,213,291; 10,646,365; 10,390,932; U.S. patent application Ser. Nos. 14/575,673; 14/272,818; 15/478,424; 15/604,032; 15/672,404; 15/816,772; 16/414,292; 15/478,424; PCT/US2017/025849; Ser. Nos. 15/478,737; 15/604,032; 15/672,404; 16/414,132; 16/379,423; 16/379,490; 16/379,354; 16/391,843; 16/391,995; 16/392,443; 16/414,208; 16/414.132; 16/433,654; and 16/433,823 are also incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A stent graft, comprising:
 a) a luminal graft component having a proximal open end and a distal open end;
 b) a plurality of stents distributed longitudinally along the luminal graft component, at least one of the stents having struts that are joined to define proximal and distal apices;
 c) a plurality of fenestrations, wherein each fenestration is nested between respective struts of adjacent stents;
 d) at least one loop secured to at least one of the struts; and
 e) at least one ligature extending through the at least one loop, each ligature traversing the struts of at least one of the stents and passing around one of the plurality of fenestrations, wherein each ligature includes ends that, when linked, at least partially radially constrict each corresponding stent.

2. An aortic prosthetic system, comprising:
 a) a luminal stent graft component having a proximal end and a distal end;
 b) at least one stent at the luminal graft component, the at least one stent having struts that are joined to define proximal apices and distal apices;
 c) a plurality of fenestrations, wherein each fenestration is nested between respective struts of adjacent stents;
 d) at least one loop secured to at least one of the struts;
 e) a ligature that extends through the loop, traverses a plurality of the struts of the at least one stent to which the loop is attached, and passes around one of the plurality of fenestrations, the ligature defining ends that, when linked, constrain the at least one stent against outward radial expansion to thereby constrict the at least one stent.

3. The aortic prosthesis system of claim 2, further including a wire that extends longitudinally along the luminal graft component and links the ends of the ligature to thereby constrict the at least one stent.

4. The aortic prosthetic system of claim 3, wherein the ligature has a first end and a second end, and extends around a circumference of the luminal graft component, and through at least a portion of the at least one loop, whereby linkage of the first and second ends causes the ligature to traverse the struts at the at least one loop and constricts outward radial expansion of the at least one stent.

5. The aortic prosthetic system of claim 4, wherein the ligature defines a ligature loop at each of the first and the second ends, whereby the first end and the second end can be linked at the ligature loop by the wire.

6. The aortic prosthetic system of claim 5, wherein the ligature is a hoop that is collapsed to thereby define a first end and a second end, and extends through at least a portion of the at least one loop, whereby linkage of the first end and the second end causes the ligature to traverse the struts at the at least one loop and constricts outward radial expansion of the at least one stent.

7. The aortic prosthetic system of claim 6, including a plurality of loops at a plurality of struts of the at least one stent.

8. The aortic prosthetic system of claim 7, wherein the plurality of loops includes at least one pair of loops at a pair of struts that join to form at least one proximal apex or distal apex, whereby constriction of the struts by the ligature causes the at least one pair of loops at the struts to be closer together than the distance between the at least one pair of loops in the absence of constriction of the ligature.

9. The aortic prosthetic system of claim 8, wherein the luminal graft component defines a fenestration between two adjoining struts of the at least one stent, and wherein the at least one pair of loops are at the adjoining struts distal to a distal end of the fenestration or proximal to a proximal end of the fenestration, whereby the ligature constricts the at least one stent without obstructing the fenestration.

10. The aortic prosthetic system of claim 9, further including a second pair of loops at the pair of struts, wherein the second pair of loops span the fenestration, and further including a loop at the luminal graft component between the at least one pair of loops distal to a distal end of the fenestration or proximal to the proximal end of the fenestration, wherein the ligature extends through the at least one pair of loops at the luminal graft component and constricts the fenestration without obstructing the fenestration, and whereby the luminal graft component at the fenestration is supported between the struts to which the at least one pair of loops are fixed.

11. The aortic prosthetic system of claim 10, wherein the ends of the ligature are linked radially apart from the fenestration.

12. The aortic prosthetic system of claim 11, further including loops at adjoining struts that define apices proximal to the distal apex nesting the fenestration, or that define apices distal to the proximal apex nesting the fenestration.

\* \* \* \* \*